(12) United States Patent
Cattaneo et al.

(10) Patent No.: US 8,877,491 B2
(45) Date of Patent: Nov. 4, 2014

(54) POLYNUCLEOTIDES ENCODING HUMANIZED ANTI-NGF ANTIBODIES

(75) Inventors: Antonino Cattaneo, Rome (IT); Doriano Lamba, Rome (IT); Sonia Covaceuszach, Rome (IT)

(73) Assignee: Abbvie Inc., North Chicago, IL (US)

( * ) Notice: Subject to any disclaimer, the term of this patent is extended or adjusted under 35 U.S.C. 154(b) by 24 days.

(21) Appl. No.: 12/838,062

(22) Filed: Jul. 16, 2010

(65) Prior Publication Data

US 2011/0191872 A1 Aug. 4, 2011

Related U.S. Application Data

(62) Division of application No. 10/583,618, filed as application No. PCT/IT2004/000722 on Dec. 23, 2004, now Pat. No. 8,296,079.

(30) Foreign Application Priority Data

Dec. 24, 2003 (IT) ................ RM20030601

(51) Int. Cl.
 *C07K 16/22* (2006.01)
 *C12N 15/85* (2006.01)

(52) U.S. Cl.
 CPC ............... *C07K 16/22* (2013.01); *C12N 15/85* (2013.01)
 USPC ........................................ 435/325; 536/23.53

(58) Field of Classification Search
 CPC .................................. C07K 16/22; C12N 15/85
 See application file for complete search history.

(56) References Cited

U.S. PATENT DOCUMENTS

| | | | |
|---|---|---|---|
| 4,230,691 A | 10/1980 | Young | |
| 5,147,294 A | 9/1992 | Smith et al. | |
| 5,639,641 A | 6/1997 | Pedersen et al. | |
| 5,693,761 A | 12/1997 | Queen et al. | |
| 5,747,060 A | 5/1998 | Sackler et al. | |
| 6,017,878 A | 1/2000 | Saragovi et al. | |
| 6,022,875 A | 2/2000 | Zimmer et al. | |
| 6,548,062 B2 | 4/2003 | Buchkovich et al. | |
| 6,881,719 B2 | 4/2005 | Saragovi et al. | |
| 6,919,426 B2 | 7/2005 | Boone et al. | |
| 7,252,822 B2 | 8/2007 | Shelton et al. | |
| 7,255,860 B2 | 8/2007 | Shelton et al. | |
| 7,371,559 B2 | 5/2008 | Boone et al. | |
| 7,425,329 B2 | 9/2008 | Shelton et al. | |
| 7,449,616 B2 | 11/2008 | Pons et al. | |
| 7,522,822 B2 | 4/2009 | Trujillo et al. | |
| 7,569,364 B2 | 8/2009 | Rosenthal et al. | |
| 7,601,818 B2 | 10/2009 | Wild, Jr. et al. | |
| 7,655,231 B2 | 2/2010 | Shelton et al. | |
| 7,655,232 B2 | 2/2010 | Pons et al. | |
| 7,727,527 B2 | 6/2010 | Shelton | |
| 7,795,413 B2 | 9/2010 | Wild, Jr. et al. | |
| 7,988,967 B2 | 8/2011 | MacDonald et al. | |
| 8,007,800 B2 | 8/2011 | Shelton et al. | |
| 2001/0046959 A1 | 11/2001 | Buchkovich et al. | |
| 2003/0087804 A1 | 5/2003 | Hempstead et al. | |
| 2004/0071701 A1 | 4/2004 | Delafoy et al. | |
| 2004/0131515 A1 | 7/2004 | Alexanian et al. | |
| 2004/0131615 A1 | 7/2004 | Shelton et al. | |
| 2004/0228862 A1 | 11/2004 | Shelton et al. | |
| 2004/0237124 A1 | 11/2004 | Pons et al. | |
| 2006/0147450 A1 | 7/2006 | Shelton | |
| 2007/0264195 A1 | 11/2007 | Nykiaer et al. | |
| 2008/0081040 A1 | 4/2008 | Shelton et al. | |
| 2008/0107658 A1 | 5/2008 | Franks et al. | |
| 2008/0213282 A1 | 9/2008 | Jacob et al. | |
| 2009/0155274 A1 | 6/2009 | Wild, Jr. et al. | |
| 2009/0300780 A1 | 12/2009 | Cattaneo et al. | |
| 2010/0034818 A1 | 2/2010 | Wild, Jr. et al. | |
| 2010/0055097 A1 | 3/2010 | Kaisheva et al. | |
| 2010/0111970 A1 | 5/2010 | Pons et al. | |
| 2010/0143355 A1 | 6/2010 | Shelton et al. | |
| 2010/0240582 A1 | 9/2010 | Boone et al. | |
| 2010/0260775 A1 | 10/2010 | Mills et al. | |
| 2010/0267934 A1 | 10/2010 | Van De Winkel et al. | |
| 2011/0014208 A1 | 1/2011 | MacDonald et al. | |
| 2011/0033447 A1 | 2/2011 | Rosenthal et al. | |
| 2011/0091476 A1 | 4/2011 | Wild, Jr. et al. | |
| 2011/0191872 A1 | 8/2011 | Cattaneo et al. | |
| 2011/0243961 A1 | 10/2011 | Shelton et al. | |
| 2011/0256587 A1 | 10/2011 | Macdonald et al. | |

FOREIGN PATENT DOCUMENTS

| | | | |
|---|---|---|---|
| EP | 0578515 | A3 | 1/1994 |
| EP | 0592106 | B1 | 4/1994 |
| EP | 1255824 | B1 | 11/2002 |
| EP | 1401498 | B1 | 3/2004 |
| EP | 1556083 | B1 | 7/2005 |
| EP | 1575522 | B1 | 9/2005 |
| EP | 1594441 | B1 | 11/2005 |
| EP | 1732949 | B1 | 12/2006 |
| EP | 1891966 | A1 | 2/2008 |

(Continued)

OTHER PUBLICATIONS

Lee, Ramee et al., "Regulation of Cell Survival by Secreted Proneurotrophins," Science, vol. 294(5548):1945-1948 (2001).
Leem, J.W. et al., "Anti-NGF Treatment Suppresses Abnormal Pain Behaviors Induced After Spinal Cord Injury in the Rat," (2000).
Levi-Montalcini, Rita et al., "Nerve growth factor: from neurotrophin to neurokine," Trends Neurosci., vol. 19:514-520 (1996).
Levi-Montalcini Rita, "The Nerve Growth Factor 35 Years Later," Science, vol. 237(4819):1154-1162 (1987).
Levine, Jon D., "New Directions in Pain Research: Molecules to Maladies," Neuron, vol. 20:649-654 (1998).
Lewin, Gary R. et al., "Nerve Growth Factor-induced Hyperalgesia in the Neonatal and Adult Rat," The Journal of Neuroscience, vol. 13(5):2136-2148 (1993).

(Continued)

*Primary Examiner* — Robert C Hayes

(74) *Attorney, Agent, or Firm* — McAndrews, Held & Malloy, Ltd.

(57) ABSTRACT

Method for the humanization of the VH and VL variable regions of an animal antibody of known sequence, humanized animal antibody obtainable according to the method, in particular anti-NGF and anti-TrkA humanized animal antibodies.

6 Claims, 27 Drawing Sheets

(56) References Cited

FOREIGN PATENT DOCUMENTS

| | | |
|---|---|---|
| EP | 2100902 A1 | 9/2009 |
| EP | 2191846 A1 | 6/2010 |
| EP | 2206728 A1 | 7/2010 |
| EP | 2263692 A1 | 12/2010 |
| EP | 2270048 A2 | 1/2011 |
| WO | 90/10644 A1 | 9/1990 |
| WO | 92/08483 A1 | 5/1992 |
| WO | 92/09631 A1 | 6/1992 |
| WO | 92/22653 A1 | 12/1992 |
| WO | 93/06213 A1 | 4/1993 |
| WO | 93/16184 A1 | 8/1993 |
| WO | 00/37103 A2 | 6/2000 |
| WO | 00/73344 A2 | 12/2000 |
| WO | 01/10203 A2 | 2/2001 |
| WO | 01/64247 A2 | 9/2001 |
| WO | 01/70984 A2 | 9/2001 |
| WO | 01/78698 A2 | 10/2001 |
| WO | 02/096356 A2 | 12/2002 |
| WO | 02/096458 A1 | 12/2002 |
| WO | 02/100387 A1 | 12/2002 |
| WO | 2004/026329 A1 | 4/2004 |
| WO | 2004/032852 A2 | 4/2004 |
| WO | 2004/032870 A2 | 4/2004 |
| WO | 2004/056385 A2 | 7/2004 |
| WO | 2004/058184 A2 | 7/2004 |
| WO | 2004/065560 A2 | 8/2004 |
| WO | 2004/073653 A2 | 9/2004 |
| WO | 2004/096122 A2 | 11/2004 |
| WO | 2005/000194 A2 | 1/2005 |
| WO | 2005/019266 A2 | 3/2005 |
| WO | 2005/044293 A2 | 5/2005 |
| WO | 2005/061540 A2 | 7/2005 |
| WO | 2005/105847 A2 | 11/2005 |
| WO | 2005/111077 A2 | 11/2005 |
| WO | 2006/077441 A1 | 7/2006 |
| WO | 2006/110883 A2 | 10/2006 |
| WO | 2006/131951 A2 | 12/2006 |
| WO | 2006/131952 A1 | 12/2006 |
| WO | 2006/137106 A2 | 12/2006 |
| WO | 2008/079290 A2 | 7/2008 |
| WO | 2008/145142 A1 | 12/2008 |
| WO | 2009/023540 A1 | 2/2009 |
| WO | 2009/077993 A2 | 6/2009 |
| WO | 2011/116090 A1 | 9/2011 |

OTHER PUBLICATIONS

Lewin, Gary R. et al., "Peripheral and Central Mechanisms of NGF-induced Hyperalgesia," European Journal of Neuroscience, vol. 6:1903-1912 (1994).
Lowe, E.M. et al., "Increased nerve growth factor levels in the urinary bladder of women with idiopathic sensory urgency and interstitial cystitis," British Journal of Urology, vol. 79:572-577 (1997).
Luger, Nancy M. et al., "Efficacy of systemic morphine suggests a fundamental difference in the mechanisms that generate bone cancer vs. inflammatory pain," Pain, vol. 99:397-406 (2002).
Mach, D.B. et al., "Sensory Nerves that Innervate Bone are Involved in Conveying Skeleton Pain," Society for Neuroscience, vol. 26:1960, Abstract No. 734.1 (2000).
Macpherson, Ross D., "The pharmacological basis of contemporary pain management," Pharmacology & Therapeutics, vol. 88:163-185 (2000).
Mantyh, Patrick W., "A mechanism-based understanding of bone cancer pain," Pathological Pain: From Molecular to Clinical Aspects: Novartis Foundation Symposium 261, vol. 261:194-219 (2004).
Mantyh, Patrick W. et al., "Molecular Mechanisms of Cancer Pain," Nature Reviews Cancer, vol. 2(3):201-209 (2002).
Matsuda, Hiroshi et al., "Role of Nerve Growth Factor in Cutaneous Wound Healing: Accelerating Effects in Normal and Healing-impaired Diabetic Mice," J. Exp. Med., vol. 187(3):297-306 (1998).
McGinty, Ann et al., "Cyclooxygenase-2 Expression Inhibits Trophic Withdrawal Apoptosis in Nerve Growth Factor-differentiated PC12 Cells," The Journal of Biological Chemistry, vol. 275(16):12095-12101 (2000).

McMahon, Stephen B., "NGF as a mediator of inflammatory pain," Phil. Trans. R. Soc. Lond. B, vol. 351:431-440 (1996).
McMahon, Stephen B. et al., "The biological effects of endogenous nerve growth factor on adult sensory neurons revealed by a trkA-IgG fusion molecule," Nature Medicine, vol. 1(8):774-780 (1995).
Millan, Mark J., "The Induction of Pain: An Integrative Review," Progress in Neurobiology, vol. 57:1-164 (1999).
Miller, Lauri J. et al., "Nerve Growth Factor and Chronic Prostatitis/Chronic Pelvic Pain Syndrome," Urology, vol. 59:603-608 (2002).
Molnar, Margherita et al., "A critical period in the sensitivity of basal forebrain cholinergic neurones to NGF deprivation," NeuroReport, vol. 8:575-579 (1997).
Molnar, Margherita et al., "The effects of anti-nerve growth factor monoclonal antibodies on developing basal forebrain neurons are transient and reversible," European Journal of Neuroscience, vol. 10:3127-3140 (1998).
Morisset, Valerie et al., "Possible mechanisms of cannabinoid-induced antinociception in the spinal cord," European Journal of Pharmacology, vol. 429:93-100 (2001).
Mousa, Shaaban A. et al., "Nerve growth factor governs the enhanced ability of opioids to suppress inflammatory pain," Brain, vol. 130:502-513 (2007).
Nakatsuka, Terumasa et al., "Activation of Central Terminal Vanilloid Receptor-1 Receptors and alphabeta-Methylene-ATP-Sensitive P2X Receptors Reveals a Converged Synaptic Activity ont the Deep Dorsal Horn Neurons of the Spinal Cord," The Journal of Neuroscience, vol. 22(4):1228-1237 (2002).
Nanduri, J. et al., "Immunological Determinants of Nerve Growth Factor Involved in p140trk (Trk) Receptor Binding," Journal of Neuroscience Research, vol. 37:433-444 (1994).
Nilsson, Gunnar et al., "Human mast cells express functional TrkA and are a source of nerve growth factor," Eur. J. Immunol., vol. 27:2295-2301 (1997).
Nykjaer, Anders et al., "Sortilin is essential for proNGF-induced neuronal cell death," Nature, vol. 427:843-848 (2004).
Oddiah, Daniela et al., "Rapid increase of NGF, BDNF and NT-3 mRNAs in inflamed bladder," NeuroReport, vol. 9:1455-1458 (1998).
Omote, Keiichi et al., "The Effects of Peripheral Administration of a Novel Selective Antagonist for Prostaglandin E Receptor Subtype EP1, ONO-8711, in a Rat Model of Postoperative Pain," Anesth. Analg., vol. 92:233-238 (2001).
Onttonen, Tiina et al., "The Mechanical Antihyperalgesic Effect of Intrathecally Administered MPV-2426, a Novel alpha2-Adrenoceptor Agonist, in a Rat Model of Postoperative Pain," Anesthesiology, vol. 92:1740-1745 (2000).
Ossipov, Michael H. et al., "Spinal and Supraspinal Mechanisms of Neuropathic Pain," Annals of the New York Academy of Sciences, vol. 909:12-24 (2000).
Owolabi, Joshua B. et al., "Characterization of Antiallodynic Actions of ALE-0540, a Novel Nerve Growth Factor Receptor Antagonist, in the Rat," The Journal of Pharmacology and Experimental Therapeutics, vol. 289(3):1271-1276 (1999).
Pesavento, Emanuele et al., "Blocking the NGF-TrkA Interaction Rescues the Developmental Loss of LTP in the Rat Visual Cortex: Role of the Cholinergic System," Neuron, vol. 25:165-175 (2000).
Peter, Elizabeth A. et al., "Ibuprofen versus acetaminophen with codeine for the relief of perineal pain after childbirth: a randomized controlled trial," CMAJ, vol. 165(9):1203-1209 (2001).
Pogatzki, Esther M. et al., "Characterization of Adelta- and C-Fibers Innervating the Plantar Rat Hindpaw One Day After an Incision," J. Neurophysiol., vol. 87:721-731 (2002).
Pogatzki, Esther M. et al., "Effect of Pretreatment with Intrathecal Excitatory Amino Acid Receptor Antagonists on the Development of Pain Behavior Caused by Plantar Incision," Anesthesiology, vol. 95:489-496 (2000).
Pogatzki-Zahn, Esther M. et al., "Postoperative pain-clinical implications of basic research," Best Practice & Research Clinical Anaesthesiology, vol. 21(1):3-13 (2007).
Pogatzki, Esther M. et al., "Role of the Rostral Medial Medulla in the Development of Primary and Secondary Hyperalgesia after Incision in the Rat," Anesthesiology, vol. 96:1153-1160 (2002).

(56) References Cited

OTHER PUBLICATIONS

Porro, Carlo A. et al., "Spatial and Temporal Aspects of Spinal Cord and Brainstem Activation in the Formalin Pain Model," Progress in Neurobiology, vol. 41:565-607 (1993).
Premkumar, Louis S. et al., "Induction of vanilloid receptor channel activity by protein kinase C," Nature, vol. 408:985-990 (2000).
Przewlocki, Ryszard et al., "Opioids in chronic pain," European Journal of PHarmacology, vol. 429:79-91 (2001).
Queen, Cary et al., "A humanized antibody that binds to the interleukin 2 receptor," Proc. Natl. Acad. Sci. USA, vol. 86:10029-10033 (1989).
Ramer, Matt S. et al., "Adrenergic innervation of rat sensory ganglia following proximal or distal painful sciatic neuropathy: distinct mechanisms revealed by anti-NGF treatment," European Journal of Neuroscience, vol. 11:837-846 (1999).
Ramer, Matt S. et al., "Nerve growth factor induces P2X3 expression in sensory neurons," Journal of Neurochemistry, vol. 77:864-875 (2001).
Ramsland, Paul A. et al., "Crystal structures of human antibodies: a detailed and unfinished tapestry of immunoglobulin gene products," J. Mol. Recognit., vol. 15:248-259 (2002).
Reeh, Peter W. et al., "Nociceptor excitation by thermal sensitization—a hypothesis," Progress in Brain Research, vol. 129:39-50 (2000).
Ro, Long-Sun et al., "Effect of NGF and anti-NGF on neuropathic pain in rats following chronic constriction injury of the sciatic nerve," Pain, vol. 79:265-274 (1999).
Ruberti, Francesca et al., "Cloning and Expression of an Anti-Nerve Growth Factor (NGF) Antibody for Studies Using the Neuroantibody Approach," Cellular and Molecular Neurobiology, vol. 13(5):559-568 (1993).
Ruberti, Francesca et al., "Phenotypic Knockout of Nerve Growth Factor in Adult Transgenic Mice Reveals Severe Deficits in Basal Forebrain Cholinergic Neurons, Cell Death in the Spleen, and Skeletal Muscle Dystrophy," The Journal of Neuroscience, vol. 20(7):2589-2601 (2000).
Ruberti, Frencesca et al., "The use of the RACE method to clone hybridoma cDNA when V region primers fail," Journal of Immunological Methods, vol. 173:33-39 (1994).
Zahn, Peter K. et al., "Primary and Secondary Hyperalgesia in a Rat Model for Human Postoperative Pain," Anesthesiology, vol. 90:863-872 (1999).
Zhu, Zhaowen et al., "Nerve Growth Factor Expression Correlates With Perineural Invasion and Pain in Human Pancreatic Cancer," Journal of Clinical Oncology, vol. 17(8):2419-2428 (1999).
Abram, Stephen E., "Necessity for an Animal Model of Postoperative Pain," Anesthesiology, vol. 86(5):1015-1017 (1997).
Schroeder et al Accession No. C36005 (1996).
Wu et al Accession No. Q9UL72 (2006).
Dean et al Accession No. AAR22755 (2004).
Breton et al Accession No. AAR53345 (2003).
Amann, R. et al., "Inhibition of carrageenan-induced edema by indomethacin or sodium salicylate does not prevent the increase of nerve growth factor in the rat hind paw," Neuroscience Letters, vol. 278:173-176 (2000).
Amann, Rainer et al., "Intraplantar injection of nerve growth factor into the rat hind paw: local edema and effects on thermal nociceptive threshold," Pain, vol. 64:323-329 (1995).
Amico-Roxas, M. et al., "Nerve Growth Factor Inhibits Some Acute Experimental Inflammations," Arch. Int. PHarmacodyn. Ther., vol. 299:269-285 (1989).
Angal, S. et al., "A Single Amino Acid Substitution Abolishes the Heterogeneity of Chimeric Mouse/Human (IgG4) Antibody," Molecular Immunology, vol. 30(1):105-108 (1993).
Averill, S. et al., "Immunocytochemical Localization of trkA Receptors in Chemically Identified Subgroups of Adult Rat Sensory Neurons," European Journal of Neuroscience, vol. 7:1484-1494 (1995).

Banik, R.K. et al., "Anti-NGF Treatment Attenuates Spontaneous Pain and Thermal, But Not Mechanical Hyperalgesia, After Hind Paw Incision in the Rat," Society for Neuroscience, Program No. 909.12 (2003).
Banik, R.K. et al., "Anti-NGF treatment attenuates spontaneous pain and thermal, but not mechanical hyperalgesia, after hind paw incision in the rat," Presentation No. 909-12, Neuroscience (2003).
Banik, Ratan K. et al., "Increased nerve growth factor after rat plantar incision contributes to guarding behavior and heat hyperalgesia," Pain, vol. 117:68-76 (2005).
Beattie, Michael S. et al., "ProNGF Induces p75-Mediates Death of Oligodendrocytes following Spinal Cord Injury," Neuron, vol. 36(3):375-386 (2002).
Bennett, Gary J. et al., "A peripheral mononeuropathy in rat that produces disorders of pain sensation like those seen in man," Pain, vol. 33:87-107 (1988).
Bennett, David L.H. et al., "Endogenous nerve growth factor regulates the sensitivity of nociceptors in the adult rat," European Journal of Neuroscience, vol. 10:1282-1291 (1998).
Berardi, N. et al., "Monoclonal antibodies to nerve growth factor affect the postnatal development of the visual system," Proc. Natl. Acad. Sci. USA, vol. 91:684-688 (1994).
Bolt, Sarah et al., "The generation of a humanized, non-mitogenic CD3 monoclonal antibody which retains in vitro immunosuppressive properties," Eur. J. Immunol., vol. 23:403-411 (1993).
Brennan, Timothy J. et al., "Characterization of a rat model of incisional pain," Pain, vol. 64:493-501 (1996).
Brennan, Timothy J. et al., "Comparison of Pre- versus Post-incision Administration of Intrathecal Bupivacaine and Intrathecal Morphine in a Rat Model of Postoperative Pain," Anesthesiology, vol. 87:1517-1528 (1997).
Brennan, T.J. et al., "Role of Nerve Growth Factor in a Rat Model for Postoperative Pain," Society for Neuroscience, vol. 24:880, Abstract No. 349.4 (1998).
Burnstock, Geoffrey, "Purine-mediated signalling in pain and visceral perception," Trends in Pharmacological Sciences, vol. 22(4):182-188 (2001).
Cahill, Catherine M. et al., "Intrathecal nerve growth factor restores opioid effectiveness in an animal model of neuropathic pain," Neuropharmacology, vol. 45:543-552 (2003).
Cain, Daivd M. et al., "Functional Interations between Tumor and Peripheral Nerve: Changes in Excitability and Morphology of Primary Afferent Fibers in a Murine Model of Cancer Pain," The Journal of Neuroscience, vol. 21 (23):9367-9376 (2001).
Capsoni, Simona et al., "Alzheimer-like neurodegeneration in aged antinerve growth factor transgenic mice," PNAS, vol. 97(12):6826-6831 (2000).
Capsoni, Simona et al., "Muscular Dystrophy in Adult and Aged Anti-NGF Transgenic Mice Resembles an Inclusion Body Myopathy," Journal of Neuroscience Research, vol. 59:553-560 (2000).
Cattaneo, Antonino et al., "Functional Blockade of Tyrosine Kinase A in the Rat Basal Forebrain in a Novel Antagonistic Anti-Receptor Monoclonal Antibody," The Journal of Neuroscience, vol. 19(22):9687-9697 (1999).
Cattaneo, Antonino et al., "Three Distinct Types of Monoclonal Antibodies After Long-Term Immunization of Rats with Mouse Nerve Growth Factor," Journal of Neurochemistry, vol. 50:1003-1010 (1988).
Chuang, Huai-hu et al., "Bradykinin and nerve growth factor release the capsaicin receptor from PtdIns(4,5)P2-mediated inhibition," Nature, vol. 411:957-962 (2001).
Clohisy, Denis R. et al., "Bone Cancer Pain," Cancer, vol. 97(3 Suppl.):866-873 (2003).
Cohen, Stanley et al., "Purification and Properties of a Nerve Growth-promoting Factor Isolated from Mouse Sarcoma 180," Cancer Research, vol. 17(1):15-20 (1957).
Costigan, Michael et al., "Pain: Molecular Mechanisms," The Journal of Pain, vol. 1(3), Suppl. 1:35-44 (2000).
Covaceuszach, Sonia et al., "Dissecting NGF Interactions with TrkA and p75 Receptors by Structural and Functional Studies of an Anti-NGF Neutralizing Antibody," J. Mol. Biol., vol. 381:881-896 (2008).

(56) References Cited

OTHER PUBLICATIONS

Covaceuszach, Sonia et al., "Neutralization of NGF-TrkA Receptor Interaction by the Novel Antagonistic Anti-TrkA Monoclonal Antibody MNAC13: A Structural Insight," Proteins: Structure, Function, and Bioinformatics, vol. 58:717-727 (2005).

Covaceuszach, Sonia et al., "Purification, crystallization, X-ray diffraction analysis and phasing of a Fab fragment of monoclonal neuroantibody alphaD11 against nerve growth factor," Acta Cryst., vol. D60:1323-1327 (2004).

Covaceuszach, Sonia et al., "Purification, crystallization and preliminary X-ray analysis of the Fab fragment from MNAC13, a novel antagonistic anti-tyrosine kinase A receptor monoclonal antibody," Acta Cryst., vol. D57:1307-1309 (2001).

De Craen, Anton J.M. et al., "Analgesic efficacy and safety of paracetamol-codeine combinations versus paracetamol alone: a systematic review," BMJ, vol. 313(7053):321-325 (1996).

Delafoy, Laure et al., "Role of nerve growth factor in the trinitrobenzene sulfonic acid-induced colonic hypersensitivity," Pain, vol. 105:489-497 (2003).

Diamond, Jack et al., "Sensory Nerves in Adult Rats Regenerate and Restore Sensory Function to the Skin Independently of Endogenous NGF," The Journal of Neuroscience, vol. 12(4):1467-1476 (1992).

Dirig, David M. et al., "Characterization of veriables defining hindpaw withdrawal latency evoked by radiant thermal stimuli," Journal of Neuroscience Methods, vol. 76:183-191 (1997).

Djouhri, Laiche et al., "Time Course and Nerve Growth Factor Dependence of Inflammation-Induced Alterations in Electrophysiological Membrane Properties in Nociceptive Primary Afferent Neurons," The Journal of Neuroscience, vol. 21(22):8722-8733 (2001).

Dmitrieva, Natalia et al., "Sensitisation of visceral afferents by nerve growth factor in the adult rat," Pain, vol. 66:87-97 (1996).

Durham, Paul L. et al., "Stimulation of the Calcitonin Gene-Related Peptide Enhancer by Mitogen-Activated Protein Kinases and Repression by an Antimigraine Drug in Trigeminal Ganglia Neurons," The Journal of Neuroscience, vol. 23(3):807-815 (2003).

Dyck, P.J. et al., "Intradermal recombinant human nerve growth factor induces pressure allodynia and lowered heat-pain threshold in humans," Neurology, vol. 48:501-505 (1997).

Fairbanks, Carolyn A. et al., "Spinal Plasticity of Acute Opioid Tolerance," J. Biomed. Sci., vol. 7:200-212 (2000).

Field, Mark J. et al., "Evaluation of Gabapentin and S-(+)-3-Isobutylgaba in a Rat Model of Postoperative Pain," The Journal of Pharmacology and Experimental Therapeutics, vol. 282(3):1242-1246 (1997).

Frade, Jose Maria et al., "Nerve growth factor: two receptors, multiple functions," BioEssays, vol. 20:137-145 (1998).

Friedman, W.J. et al., "Regulation of Beta-Nerve Growth Factor Expression by Inflammatory Mediators in Hippocampal Cultures," Journal of Neuroscience Research, vol. 27:374-382 (1990).

Galfre, G. et al., "Preparation of Monoclonal Antibodies: Strategies and Procedures," Methods in Enzymology, vol. 73:(Pt. B):3-46 (1981).

Garaci, Enrico et al., "Anti-nerve growth factor Ab abrogates macrophage-mediated HIV-1 infection and depletion of CD4+ T lymphocytes in hu-SCID mice," PNAS, vol. 100(15):8927-8932 (2003).

Rudikoff, Stuart et al., "Single amino acid substitution altering antigen-binding specificity," Proc. Natl. Acad. Sci. USA, vol. 79:1979-1983 (1982).

Rueff, Alain et al., "Characteristics of nerve growth factor induced hyperalgesia in adult rats: dependence on enhanced bradykinin-1 receptor activity but not neurokinin-1 receptor activation," Pain, vol. 66:359-372 (1996).

Rueff, Alain et al., "Nerve Growth Factor nad NT-5 Induce Increased Thermal Sensitivity of Cutaneous Nociceptors In Vitro," Journal of Neurophysiology, vol. 76(5):3593-3596 (1996).

Sabino, M.C. et al., "Defining the Cellular and Molecular Mechanisms that Generate and Maintain Bone Cancer Pain," Society for Neuroscience, vol. 27:143, Abstract No. 55.3 (2001).

Sabino, Mary Ann C. et al., "Different Tumors in Bone Each Give Rise to a Distinct Pattern of Skeletal Destruction, Bone Cancer-Related Pain Behaviors and Neurochemical Changes in the Central Nervous System," Int. J. Cancer, vol. 104:550-558 (2003).

Safieh-Garabedian, Bared et al., "Contribution of interleukin-1beta to the inflammation-induced increase in nerve growth factor levels and inflammatory hyperalgesia," British Journal of Pharmacology, vol. 115:1265-1275 (1995).

Safieh-Garabedian, Bared et al., "Involvement of Interleukin-1beta, Nerve Growth Factor, and Prostaglandin-E2 in the Hyperalgesia Induced by Intraplantar Injections of Low Doses of Thymulin," Brain, Behavior, and Immunity, vol. 11:185-200 (1997).

Safieh-Garabedian, B. et al., "The role of cytokines and prostaglandin-E2 in thymulin induced hyperalgesia," Neuropharmacology, vol. 39:1653-1661 (2000).

Sammons, Melanie J. et al., "Carrageenan-induced thermal hyperalgesia in the mouse: role of nerve growth factor and the mitogen-activated protein kinase pathway," Brain Research, vol. 876:48-54 (2000).

Saper, Clifford B. et al., "Neuronal pathology in the nucleus basalis and associated cell groups in senile dementia of the Alzheimer's type: Possible role in cell loss," Neurology, vol. 35:1089-1095 (1985).

Saragovi, H. Uri et al., "Development of pharmacological agents for targeting neurotrophins and their receptors," Trends in Pharmacol. Sci., vol. 21(3):93-98 (2000).

Sarchielli, Paola et al., "Levels of nerve growth factor in cerebrospinal fluid of chronic daily headache patients," Neurology, vol. 57(1):132-134 (2001).

Schwei, Matthew J. et al., "Neurochemical and Cellular Reorganization of the Spinal Cord in a Murine Model of Bone Cancer Pain," The Journal of Neuroscience, vol. 19(24):10886-10897 (1999).

Sedel, Frederic et al., "Nerve growth factor (NGF) induces motoneuron apoptosis in rat embryonic spinal cord in vitro," European Journal of Neuroscience, vol. 11:3904-3912 (1999).

Sevcik, Molly A. et al., "Anti-NGF therapy profoundly reduces bone cancer pain and the accompanying increase in markers of peripheral and central sensitization," Pain, vol. 115:128-141 (2005).

Shelton, David L. et al., "Expression of the beta-nerve growth factor gene correlates with the density of sympathetic innervation in effector organs," Proc. Natl. Acad. Sci. USA, vol. 81:7951-7955 (1984).

Shelton, David L. et al., "Neurotrophins and neurotrophin and antagonists as potential therapeutics," Restorative Neurology and Neuroscience, vol. 8:99-100 (1995).

Shu, Xiaoquan et al., "Nerve growth factor acutely sensitizes the response of adult rat sensory neurons to capsaicin," Neuroscience Letters, vol. 274:159-162 (1999).

Shu, X.-Q. et al., "Neurotrophins and hyperalgesia," Proc. Natl. Acad. Sci. USA, vol. 96:7693-7696 (1999).

Sivilotti, Lucia et al., "GABA Receptor Mechanisms in the Central Nervous System," Progress in Neurobiology, vol. 36:35-92 (1991).

Sorkin, Linda S. et al., "Acute Pain Mechanisms," Surgical Clinics of North America, vol. 79(2):213-229 (1999).

Stein, Christoph et al., "Peripheral mechanisms of opioid analgesia," Current Opinion in Pharmacology, vol. 9:3-8 (2009).

Stubhaug, A. et al., "Mapping of punctuate hyperalgesia around a surgical incision demonstrates that ketamine is a powerful suppressor of central sensitization to pain following surgery," Acta Anaesthesiol. Scand., vol. 41:1124-1132 (1997).

Svensson, Peter et al., "Injection of nerve growth factor into human masseter muscle evokes long-lasting mechanical allodynia and hyperalgesia," Pain, vol. 104:241-247 (2003).

Taglialatela, G. et al., "Nerve Growth Factor Modulates the Activation of the Hypothalamo—Pituitary—Adrenocortical Axis during the Stress Response," Endocrinology, vol. 129(4):2212-2218 (1991).

Tal, Michael et al., "Local injection of nerve growth factor (NGF) triggers degranulation of mast cells in rat paw," Neuroscience Letters, vol. 221:129-132 (1997).

Tallarida, Ronald J., "An Overview of Drug Combination Analysis with Isobolograms," The Journal of Pharmacology and Experimental Therapeutics, vol. 319(1):1-7 (2006).

Tamura, Midori et al., "Structural Correlates of an Anticarcinoma Antibody: Identification of Specificity-Determining Residues

(56) References Cited

OTHER PUBLICATIONS (SDRs) and Development of a Minimally Immunogenic Antibody Variant by Retention of SDRs Only," The Journal of Immunology, vol. 164:1432-1441 (2000).

Theodosiou, M. et al., "Hyperalgesia due to nerve damage: role of nerve growth factor," Pain, vol. 81:245-255 (1999).

Treede, Rolf-Detlef et al., "Peripheral and Central Mechanisms of Cutaneous Hyperalgesia," Progress in Neurobiology, vol. 38:397-421 (1992).

Tsuda, Makoto et al., "Role of endogenous ATP at the incision area in a rat model of postoperative pain," NeuroReport, vol. 12(8):1701-1704 (2001).

Urch, C.E. et al., "Alterations in dorsal horn neurones in a rat model of cancer-induced bone pain," Pain, vol. 106:347-356 (2003).

Wang, Yong-Xiang et al., "Effects of intrathecal administration of ziconotide, a selective neuronal N-type calcium channel blocker, on mechanical allodynia and heat hyperalgesia in a rat model of postoperative pain," Pain, vol. 84:151-158 (2000).

Wilder-Smith, Oliver H.G., "Pre-emptive analgesia and surgical pain," Progress in Brain Research, vol. 129:505-524 (2000).

Winston, John H. et al., "Acute Pancreatitis Results in Referred Mechanical Hypersensitivity and Neuropeptide Up-Regulation That Can be Suppressed by the Protein Kinase Inhibitor K252a," The Journal of Pain, vol. 4(6):329-337 (2003).

Winston, John et al., "Nerve growth factor regulates VR-1 mRNA levels in cultures of adult dorsal root ganglion neurons," Pain, vol. 89:181-186 (2001).

Woolf, C.J. et al., "Nerve Growth Factor Contributes to the Generation of Inflammatory Sensory Hypersensitivity," Neuroscience, vol. 62(2):327-331 (1994).

Woolf, Clifford J. et al., "Neuronal Plasticity: Increasing the Gain in Pain," Science, vol. 288:1765-1768 (2000).

Woolf, Clifford J. et al., "Peripheral Cell Types Contributing to the Hyperalgesic Action of Nerve Growth Factor in Inflammation," The Journal of Neuroscience, vol. 16(8):2716-2723 (1996).

Woolf, Clifford J., "Phenotype modification of primary sensory neurons: the role of nerve growth factor in the production of persistent pain," Phil. Trans. R. Soc. Lond. B, vol. 351:441-448 (1996).

Woolf, Clifford J. et al., "Preemptive Analgesia—Treating Postoperative Pain by Preventing the Establishment of Central Sensitization," Anesth. Analg., vol. 77(2):362-379 (1993).

Xanthos, Dimitris N. et al., "The roles of nerve growth factor and cholecystokinin in the enhancement of morphine analgesia in a rodent model of central nervous system inflammation," Neuropharmacology, vol. 56:684-691 (2009).

Yamamoto, Tatsuo et al., "Anti-allodynic effects of oral COX-2 selective inhibitor on postoperative pain in the rat," Can. J. Anesth., vol. 47(4):354-360 (2000).

Yamamoto, Tatsuo et al., "Spinal N-acetyl-alpha-linked acidic dipeptidase (NAALADase) inhibition attenuates mechanical allodynia induced by paw carrageenan injection in the rat," Brain Research, vol. 909:138-144 (2001).

Yamdeu, Reine-Solange et al., "p38 Mitogen-activated Protein Kinase Activation by Nerve Growth Factor in Primary Sensory Neurons Upregulates Mu-Opioid Receptors to Enhance Opioid Responsiveness Toward Better Pain Control," Anesthesiology, vol. 114(1):150-161 (2011).

Zahn, Peter K. et al., "Effect of Blockade of Nerve Growth Factor and Tumor Necrosis Factor on Pain Behaviors After Plantar Incision," The Journal of Pain, vol. 5(3):157-163 (2004).

Zahn, Peter K. et al., "Effect of Systemic and Intrathecal Morphine in a Rat Model of Postoperative Pain," Anesthesiology, vol. 86:1066-1077 (1997).

Zahn, Peter K. et al., "Intrathecal non-NMDA excitatory amino acid receptor antagonists inhibit pain behaviors in a rat model of postoperative pain," Pain, vol. 74:213-223 (1998).

Zahn, Peter K. et al., "Lack of Effect of Intrathecally Administered N-methyl-D-aspartate Receptor Antagonists in a Rat Model for Postoperative Pain," Anesthesiology, vol. 88:143-156 (1998).

Zahn, Peter K. et al., "Mechanisms for Pain Caused by Incisions," Regional Anesthesia and Pain Medicine, vol. 27 (5):514-516 (2002).

Ghilardi, J.R. et al., "A Neuropathic Component to Bone Cancer Pain," Society for Neuroscience, Program No. 815.9 (2003).

Goldstein, Frederick J., "Adjuncts to opioid therapy," JAOA, vol. 102(9), Suppl. 3:S15-S20 (2002).

Gonfloni, Stefania, "Recombinant antibodies as structural probes for neurotrophins," ISAS International School for Advanced Studies (1995).

Gonzalez, M. Isabel et al., "Evaluation of PD 154075, a tachykinin NK1 receptor antagonist, in a rat model of postoperative pain," European Journal of Pharmacology, vol. 344:115-120 (1998).

Grabovsky, Yury et al., "Isobolographic Analysis for Combinations of a Full and Partial Agonist: Curved Isoboles," The Journal of Pharmacology and Experimental Therapeutics, vol. 310(3):981-986 (2004).

Grills, Brian L. et al., "Immunohistochemical localization of nerve growth factor in fractured and unfractured rat bone," Acta Orthop Scand, vol. 69(4):415-419 (1998).

Gwak, Young Seob et al., "Attenuation of mechanical hyperalgesia following spinal cord injury by administration of antibodies to nerve growth factor in the rat," Neuroscience Letters, vol. 336:117-120 (2003).

Halliday, Dale A. et al., "Elevated Nerve Growth Factor Levels in the Synovial Fluid of Patients with Inflammatory Joint Disease," Neurochemical Research, vol. 23(6):919-922 (1998).

Halvorson, Kyle G. et al., "A Blocking Antibody to Nerve Growth Factor Attenuates Skeletal Pain Induced by Prostate Tumor Cells Growing in Bone," Cancer Res., vol. 65(20):9426-9435 (2005).

Hamalainen, Minna M. et al., "Acute Effect of an Incision on Mechanosensitive Afferents in the Plantar Rat Hindpaw," J. Neurophysiol., vol. 87:712-720 (2002).

Hanks, G.W., "Opioid-responsive and opioid-non-responsive pain in cancer," British Medical Bulletin, vol. 47 (3):718-731 (1991).

Harpf, Christoph et al., "Receptors for NGF and GDNF are Highly Expressed in Human Peripheral Nerve Neuroma," Muscle & Nerve, vol. 25:612-615 (2002).

Harrington, A.W. et al., "Secreted proNGF is a pathophysiological death-inducing ligand after adult CNS injury," PNAS, vol. 101(16):6226-6230 (2004).

Hasan, Wohaib et al., "Coordinate expression of NGF and alpha-smooth muscle actin mRNA and protein in cutaneous would tissue of developing and adult rats," Cell Tissue Res., vol. 300:97-109 (2000).

Aloe, Luigi et al., "Nerve Growth Factor in the Synovial Fluid of Patients with Chronic Arthritis," Arthritis and Rheumatism, vol. 35(3):351-355 (1992).

Brennan, Timothy J., "Postoperative Models of Nociception," ILAR J., vol. 40(3):129-136 (1999).

Constantinou, Jason et al., "Nerve growth factor levels in developing rat skin: upregulation following skin wounding," NeuroReport, vol. 5:2281-2284 (1994).

Field, Mark John et al., "Enadoline, a selective kappa-opioid receptor agonist shows potent antihyperalgesic and antiallodynic actions in a rat model of surgical pain," Pain, vol. 80:383-389 (1999).

Hefti, Franz F. et al., "Novel class of pain drugs based on antagonism of NGF," Trends in Pharmacological Sciences, vol. 27(2):85-91 (2006).

Hempstead, Barbara L., "The many faces of p75NTR," Current Opinion in Neurobiology, vol. 12:260-267 (2002).

Herzberg, Uri et al., "NGF involvement in pain induced by chronic constriction injury of the rat sciatic nerve," NeuroReport, vol. 8:1613-1618 (1997).

Hill, R.G., "Molecular Basis for the Perception of Pain," Neuroscientist, vol. 7(4):282-292 (2001).

Holtzman, David M. et al., "p140trk mRNA Marks NGF-Responsive Forebrain Neurons: Evidence that trk Gene Expression is Induced by NGF," Neuron, vol. 9:465-478 (1992).

Hongo, Jo-Anne S. et al., "Antibody Binding Regions on Human Nerve Growth Factor Identified by Homolog- and Alanine-Scanning Mutagenesis," Hybridoma, vol. 19(3):215-227 (2000).

Honore, Prisca et al., "Bone Cancer Pain: From Mechanisms to Model to Therapy," Pain Medicine, vol. 1 (4):303-309 (2000).

(56) References Cited

OTHER PUBLICATIONS

Horigome, Kazuhiko et al., "Mediator Release from Mast Cells by Nerve Growth Factor, Neurotrophin Specificity and Receptor Mediation," The Journal of Biological Chemistry, vol. 268(20):14881-14887 (1993).

Hunt, Stephen P. et al., "The Molecular Dynamics of Pain Control," Nature Reviews Neuroscience, vol. 2:83-91 (2001).

Hurley, Robert W. et al., "Sex, Gender, and Pain: An Overview of a Complex Field," Anesthesia & Analgesia, vol. 107(1):309-317 (2008).

Indo, Yasuhiro, "Molecular Basis of Congenital Insensitivity to Pain With Anhidrosis (CIPA): Mutations and Polymorphisms in TRKA (NTRK1) Gene Encoding the Receptor Tyrosine Kinase for Nerve Growth Factor," Human Mutation, vol. 18:462-471 (2001).

Indo, Yasuhiro et al., "Congenital Insensitivity to Pain With Anhidrosis (CIPA): Novel Mutations of the TRKA (NTRK1) Gene, a Putative Uniparental Disomy, and a Linkage of the Mutant TRKA and PKLR Genes in a Family With CIPA and Pyruvate Kinase Deficiency," Human Mutation, vol. 18:308-318 (2001).

Indo, Yasuhiro et al., "Mutations in the TRKA/NGF receptor gene in patients with congenital insensitivity to pain with anhidrosis," Nature Genetics, vol. 13:485-488 (1996).

Ishikawa, Toshizo, "Involvement of Nerve Growth Factor in Development of Hyperalgesia," Jpn. Pharmacol. Ther., vol. 26(6):63-69 (1998).

Jaggar, S.I. et al., "Inflammation of the rat urinary bladder is associated with a referred thermal hyperalgesia which is nerve growth factor dependent," British Journal of Anaesthesia, vol. 83(3):442-448 (1999).

Ji, Ru-Rong et al., "p38 MAPK Activation by NGF in Primary Sensory Neurons after Inflammation Increases TRPV1 Levels and Maintains Heat Hyperalgesia," Neuron, vol. 36:57-68 (2002).

Jongen, J.L.M. et al., "Neurotrophic Factors and Cancer Pain: The Expression of NGF, GDNF and BDNF by the Murine Osteolytic Sarcoma Cell Line 2472 in Vitro and in Vivo and Their Potential Involvement in Bone Cancer Pain," Society for Neuroscience, Abstract No. 52.2 (2002).

Jongen, J.L.M. et al., "Neurotrophic factors and cancer pain: The expression of NGF, GDNF and BDNF by the murine osteolytic sarcoma cell line 2472 in vitro and in vivo and their potential involvement in bone cancer pain," Society for Neuroscience, Abstract No. 52.20 (2002).

Joranson, David E. et al., "Trends in Medical Use and Abuse of Opioid Analgesics," JAMA, vol. 283(13):1710-1714 (2000).

Julius, David et al., "Molecular mechanisms of nociception," Nature, vol. 413:203-210 (2001).

Kaplan, David R., "Studying signal transduction in nduronal cells: The Trk/NGF system," Progress in Brain Research, vol. 117:35-46 (1998).

Kawamoto, Keiko et al., "Nerve Growth Factor Activates Mast Cells Through the Collaborative Interaction with Lysophosphatidylserine Expressed on the Membrane Surface of Activated Platelets," The Journal of Immunology, vol. 168:6412-6419 (2002).

Kehlet, Henrik, "Synergism between Analgesics," Annals of Medicine, vol. 27:259-262 (1995).

Kessler, J.A., "Differential Regulation of Peptide and Catecholamine Characters in Cultured Sympathetic Neurons," Neuroscience, vol. 15(3):827-839 (1985).

Kessler, John A., "Parasympathetic, Sympathetic, and Sensory Interactions in the Iris: Nerve Growth Factor Regulates Cholinergic Ciliary Ganglion Innervation In Vivo," The Journal of Neuroscience, vol. 5(10):2719-2725 (1985).

Khakh, Baljit S., "Molecular Physiology of P2X Receptors and ATP Signalling at Synapses," Nature Reviews Neuroscience, vol. 2:165-174 (2001).

Kidd, B.L. et al., "Mechanisms of inflammatory pain," British Journal of Anaesthesia, vol. 87(1):3-11 (2001).

Knusel, Beat et al., "K-252 Compounds: Modulators of Neurotrophin Signal Transduction," Journal of Neurochemistry, vol. 59(6):1987-1996 (1992).

Koltzenburg, Martin et al., "Neutralization and endogenous NGF prevents the sensitization of nociceptors supplying inflamed skin," European Journal of Neuroscience, vol. 11:1698-1704 (1999).

Kryger, Gil S. et al., "Nerve Growth Factor Inhibition Prevents Traumatic Neuroma Formation in the Rat," The Journal of Hand Surgery, vol. 26A:635-644 (2001).

Labuz, Dominika et al., "Relative contribution of peripheral verus central opioid receptors to antinociception," Brain Research, vol. 1160:30-38 (2007).

Lamb, K. et al., "Nerve growth factor and gastric hyperalgesia in the rat," Neurogastroenterol Motil, vol. 15:355-361 (2003).

FIG. 1A
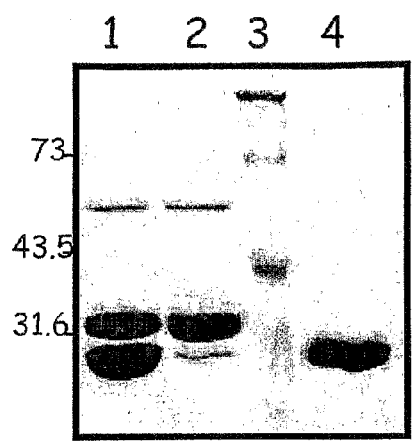
FIG. 1B
FIG. 1C
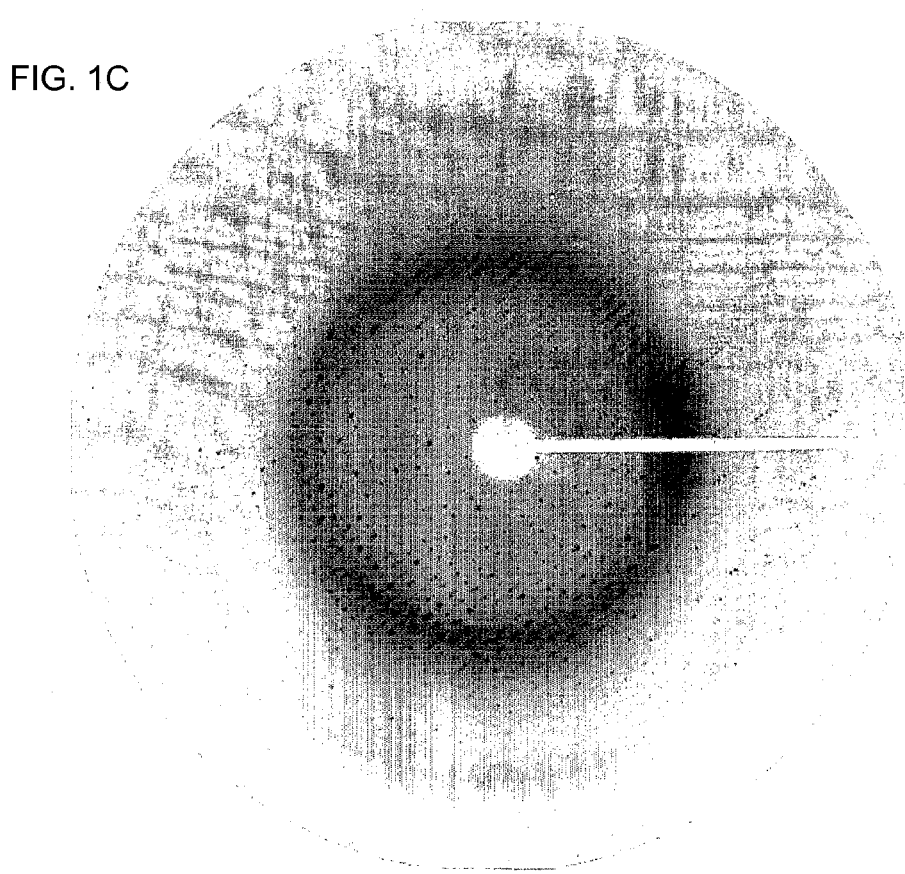

FIG. 5A
*Fv fragment of heavy chain*

```
                              20                      40
MNAC13       EVKLVESGGGLVQPGGSLKLSCAASGFTFSTYTMSWARQTPEKRLEWVAYISKG--
             || | |||||||||||| |||| |||||  | | || | | |||  |
1AD0         EVQLLESGGGLVQPGGSLRLSCATSGFTFTDYYMNWVRQAPGKGLEWLGFIGNKAN
Hum MNAC13   EVQLLESGGGLVQPGGSLRLSCAASGFTFSTYTMSWARQAPGKGLEWVAYISKG--

60                      80                     100
MNAC13       GGSTYYPDTVKGRFTISRDNAKNTLYLQMSSLKSEDTALYYCARGAMFGNDFFFPMD
             |  | |  |||||||||||| | |||||| | || | || || |||  ||   | |
1AD0         GYTTEYSASVKGRFTISRDKSKSTLYLQMNTLQAEDSAIYYCTRDR----GLRFYFD
Hum MNAC13   GGSTYYPDTVKGRFTISRDNSKNTLYLQMNSLRAEDSAVYYCARGAMFGNDFFFPMD

MNAC13       RWGQGTSVTVSSA
             ||||| ||||
1AD0         YWGQGTLVTVSSA
Hum MNAC13   RWGQGTLVTVSSA
```

FIG. 5B
*Fv fragment of light chain*

```
                              20                      40
MNAC13       DIVLTQSPAIMSASLGEEVTLTCSASSSVSYMHWYQQKSGTSPKLLIYTTSNL
             ||||||   | |   ||  || || ||||| |  ||||||  |  || ||||
1AD0         QTVLTQSPSSLSVSVGDRVTITCRASSSVTYIHWYQQKPGLAPKSLIYATSNL
Hum MNAC13   DIVLTQSPSSLSASVGDRVTITCSASSSVSYMHWYQQKPGQAPKLLIYTTSNL 60                      80                     100
MNAC13       ASGVPSRFSGSGSGTFYSLTISSVEAEDAADYYCHQWSSYPWTFGGGTKLEIK
             |||||||||||||| |  ||||   |  ||  | ||| || | ||| || | |
1AD0         ASGVPSRFSGSGSGTDYTFTISSLQPEDIATYYCQHWSSKPPTFGQGTKVEVK
Hum MNAC13   ASGVPSRFSGSGSGTDYTLTISSLQPEDVATYYCHQWSSYPWTFGGGTKVEIK
```

FIG. 6A
*Fv fragment of heavy chain*

```
                        20                    40
αD11       QVQLKESGPGLVQPSQTLSLTCTVSGFSLTNNNVNWVRQATGRGLEWMGGVWAG-G
           ||| ||| ||||||   | | |  |||        ||||| | |||| |          |
1JPS       EVQLVESGGGLVQPGGSLRLSCAASGFNIKEYYMHWVRQAPGKGLEWVGLIDPEQG
Hum αD11   EVQLVESGGGLVQPGGSLRLSCAASGFSLTNNNVNWVRQAPGKGLEWVGVWAG-G 60                    80                   100
αD11       ATDYNSALKSRLTITRDTSKSQVFLKMHSLQSEDTATYYCARDGGYSSSTLYAMD
           ||     ||  ||  | ||    || ||  |||| ||||||
1JPS       NTIYDPKFQDRATISADNSKNTAYLQMNSLRAEDTAVYYCARDTAA------YFD
Hum αD11   ATDYNSALKSRFTISRDNSKNTAYLQMNSLRAEDTAVYYCARDGGYSSSTLYAMD

αD11       AWGQGTTVTVSA
           |||||  ||||
1JPS       YWGQGTLVTVSS
Hum αD11   AWGQGTLVTVSS
```

FIG. 6B
*Fv fragment of light chain*

```
                        20                    40
αD11       DIQMTQSPASLSASLGETVTIECRASEDIYNALAWYQQKPGKSPQLLIYNTDTL
           ||||||||| ||||| |   || |||| ||     |||||||||  |  ||||||  ||| |
1JPS       DIQMTQSPSSLSASVGDRVTITCRASRDIKSYLNWYQQKPGKAPKVLIYYATSL
Hum αD11   DIQMTQSPSSLSASVGDRVTITCRASEDIYNALAWYQQKPGKAPKLLIYNTDTL 60                    80                   100
αD11       HTGVPSRFSGSGSGTQYSLKINSLQSEDVASYFCQHYFHYPRTFGGGTKLELK
           ||||||||||||| |    ||  | |||  |||  | | ||| |||  |
1JPS       AEGVPSRFSGSGSGTDYTLTISSLQPEDFATYYCLQHGESPWTFGQGTKVEIK
Hum αD11   HTGVPSRFSGSGSGTDYTLTISSLQPEDFATYFCQHYFHYPRTFGQGTKVEIK
```

FIG. 7A  *MNAC13 VL*

GAC ATT GTT CTC TCC CAG TCT CCA GCA ATC ATG TCT GCA TCT CTA GGG GAG GAG ATC ACC CTA ACC TGC AGT GCC AGC
TTG AGT GTA AGT TAC ATG CAC TGG TAC CAG AAG TCA CAG ACT TCT CCC AAG CTC TTG ATT TAT ACT ACA TCC AAC
CTG GCT TCT GGA GTC CCT TCT CGC TTC AGT GGC AGT GGG TCT GGG ACC TTT TAT CTC ACA ATC AGT AGT GTG GAG
GCT GAA GAT GCT GCC GAT TAT TAC TGC CAT CAG TGG AGT AGT TAT CCA ACG TTC GGT GGA GGC ACC AAG CTG GAA
ATC AAA

FIG. 7B  *MNAC13 VH*

GAG GTG AAG CTG GTG GAG TCT GGG GGA GGT TTA GTG CAG CCT GGA GGG TCC CTG AAA CTC TCC TGT GCA GCC TCT GGA
TTC ACT TTC AGT ACC TAT GCT ATG TCT TGG GCT CGC CAG ACT CCA GAG AAG AGG CTG GAG TGG GTC GCA TAC ATT AGT
AAA GGT GGT AGT ACC TAC TAT CCA GAC AGT GTA AAG GGC CGA TTC ACC ATC TCC AGG GAC AAT GCG AAG AAC ACC
CTG TAC CTG CAA ATG AGC AGT CTG AAG TCT GAG GAC ACG GCC TTG TAT TAC TGT GCA AGA GGG GCT ATG TAT GGT AAC
GAT TTT TTC TAT CCT ATG GAC TAC TGG GGT CAA GGA ACC TCA GTC ACC GTC TCC TCA

FIG. 7C  *MNAC13 GRAFTED VL*

```
        D   I   V   L   T   Q   S   P   S   S   L   S   A   S   V   G   D   R   V   T   I   T   C   S
5'                                OLIGO L1S
ACA GGC GTG CAC TCC GAC ATT GTT CTC ACC CAG TCT CCA AGC TCC CTG TCT GCG TCT GTC GGG GAC CGG GTC ACC ATT
                                                                            CAG CCC GCC CAG TGG TAA TGG ACG TCG
3'                                                                                                          5'

A   S   S   V   S   Y   M   H   W   Y   Q   Q   K   P   G   K   A   P   K   L   L   I   Y   T   L
5'                                        OLIGO L3S
                                          TGG TAC CAG CAG AAG CCA GGC AAG GCT CCC AAG CTC CTG ATT TAT ACA TCC AAC CTG
CGG TCG AGA TCA CAC TCA ATG TAC GTG ACC ATG GTC GTC TTC GGT CCG                                                     GAC
                    OLIGO L2AS
3'                                                                                                                      5'

A   S   G   V   P   S   R   F   S   G   S   G   S   G   T   D   Y   T   L   T   I   S   S   L   Q   P   E   D   F
5'                                                                              ACC CTC ACA ATC AGT AGT CTG CAG CCT GAA GAT TTC
GCT TCT GGA GTC CCT TCT                                                         TGG GAG TGT TAG TCA TCA GAC
CGA AGA CCT CAG GGA AGA GCG AAG TCG CCA TCA CCC AGA CCC TGG CTA ATA
                                   OLIGO L4AS
3'                                                                                                                              5'

A   T   Y   Y   C   H   Q   W   S   S   Y   P   W   T   F   G   G   G   T   K   V   E   I   K
5'                                          OLIGO L5S
                                            AGT AGT TAT CCA TGG ACG
                                            ACC TCA ATA GGT ACC TGC AAG CCA CCT CCG TGG TTC CAC CTT TAT TTT GCA CTC ATC TTA TCT
GCC ACC TAT TAC TGC CAT CAG
                              OLIGO L6AS
3'                                                                                                                              5'

AGA TTG AAT
3'         5'
```

FIG. 7D  *MNAC13 GRAFTED VH*

```
      E   V   Q   L   L   E   S   G   G   G   L   V   Q   P   G   G   S   L   R   L   S   C   A   A
5'
ACA GGC GCG CAC TCC GAG GTG CAG CTG CTG GAG TCT GGG GGA GGT TTA GTG CAG CCT GGA GGG TCC CTG CGC CTC TCC TGT GCA
                                                      OLIGO H1S
                                                                                  CCC AGG GAC GCG GAG AGG ACA CGT CGG
3'                                                                                                                    5'

S   G   F   T   F   S   T   Y   T   M   S   W                   A   R   Q   A   P   G   K   G
5'
                                                  TGG GCT CGC CAG GCC CCA GGG AAG GGG
                                                              OLIGO H3S
AGA CCT AAG AAG TCA AAG TGG TAC TCG ACC CGA GCG GTC CGG GGT CCC                                              ATT AGT AAA
                                                      OLIGO H2AS
3'                                                                                                                    5'

G   G   L   E   W   V   A   Y   I   S
5'
                          CTG GAG TGG GTC GCA TAC ATT AGT AAA
      G   G   S   T   Y   Y   P   D   T   V   K   G   R   F   T   I   S   R   D   N   S   K   N   T   L   Y   L   Q
GGT GGT AGT ACC TAC TAT CCA GAC ACT GTG AAG GGC CGA TTC ACC ATC TCC AGA GAC AAT TCC AAG AAC ACC TTG TAC CTG CAA
          CCA TCA TGG ATG ATA GGT CTG TGA CAC TTC CCG GCT AAG TGG TAG AGG TCT CTG TTG AGC TTC TTG TGG GAT ATG GAC GTT
                                                                        OLIGO H4AS
3'                                                                                                                    5'

M   N   S   L   R   A   E   D   S   A   V   Y   Y   C   A   R   G   A   M   F   G   N   D   F   F   P   M   D
5'
ATG AAC AGT CTG CGG GCT GAG GAC AGC GCC GTC TAT TAC TGT GCA AGA GGG GCT ATG TTT
                                              OLIGO H5S
                                                              ACA CGT TCT CCC CGA TAC AAA CCA TTG CTA AAA AAG GGA TAC CTG
                                                                              OLIGO H6AS
3'                                                                                                                    5'

R   W   G   Q   G   T   L   V   T   V   S
GCG ACC CCA GTT CCT TGG GAC CAG TGG CAG AGG
3'                                              5'
```

FIG. 7E  OLIGOs TO SYNTHESIZE MNAC13 VL

OLIGO L1S
ACA GGC GTG CAC TCC GAC ATT GTT CTC ACC CAG TCT CCA TCC AGC CTG TCT GCG TCT GTG GGG GAC CGG GTC ACC ATT

OLIGO L2AS
GCC TGG CTT CTG CTG GTA CCA GTG CAT ACT CAC GTA ACT GGC GCT GCA GGT AAT GGT GAC CCG GTC CCC GAC

OLIGO L3S
TGG TAC CAG CAG AAG CCA GGC AAG GCT CCC AAG CTC CTG ATT TAT ACT ACA TCC AAC CTG GCT TCT GGA GTC CCT TCT

OLIGO L4AS
CAG ACT ACT GAT TGT GAG GGT ATA ATC GGT CCC AGA CCC ACT GCC GAA GCG AGA AGG GAC TCC AGA AGC CAG

OLIGO L5S
ACC CTC ACA ATC AGT AGT CTG CAG CCT GAA GAT TTC GCC ACC TAT TAC TGC CAT CAG TGG AGT TAT CCA TGG ACG

OLIGO L6AS
TAA GTT AGA TCT ATT CTA CTC ACG TTT TAT TTC CAC CGT CCA TGG ATA ACT ACT CCA

FIG. 7F  OLIGOs TO SYNTHESIZE MNAC13 VH

OLIGO H1S
ACA GGC GCG CAC TCC GAG GTG CAG CTG GAG TCT GGG GGA GGT TTA GTG CAG CCT GGA GGG TCC CTG CGC CTC TCC TGT

OLIGO H2AS
CCC TGG GGC CTG GCG AGC CCA GCT CAT GGT ATA GGT ACT GAA AGT GAA TCC AGA GGC ACA GGA GAG GCG CAG GGA CCC

OLIGO H3S
TGG GCT CGC CAG GCC CCA GGG AAG GGG CTG GAG TGG GTT CTT CGA GAT GTT CCT GAT GGT GAA TCG CTT TAC AGT GTC TGG ATA GTA ACT ACC

OLIGO H4AS
TTG CAG GTA CAG GGT GTT CTT CGA AAC AGT CGG GCT GCT GAG GAC AGC GCC TAT TAC TGT GCA AGA GGG GCT ATG TTT

OLIGO H5S
AAG AAC ACC CTG TAC CTG CAA ATG AGT CGG GCT GCT GAG GAC AGC GCC TAT TAC TGT GCA AGA GGG GCT ATG TTT

OLIGO H6AS
GGA GAC GGT GAC CAG GGT TCC TTG ACC CCA GCG GTC CAT AGG AAA GAA AAA ATC GTT ACC AAA CAT AGC CCC TCT TGC ACA

FIG. 8A    αD11 VL

GAC ATC CAG ATG ACC CAG TCT CCA GCT TCC CTG TCT GCA TCT CTG GGA GAA ACT GTC ACC ATC GAA TGT CGA GCA AGT GAG GAC ATT
TAT AAT GCT TTA GCA TGG TAT CAG CAG AAA CCA GGA AAA TCT CCT CTC AAG CTC CTG ATC TAT ACA GAT ACC TTG CAT ACT GGG GTC
CCA TCA CGA TTC AGT GGC AGT GGA TCT GGT ACA CAA TCT CGG AAG ATA AAC AGC CTG CAA TCT GAA GAT GTC GCA AGT TAT TTC
TGT CAG CAC TAT TTC CAT CCT CGG ACG TTC GGT GGA GGG ACC AAG CTG GAG ATC AAA

FIG. 8B    αD11 VH

CAG GTG CAG CTG GTG GAA TCA GGA CCT GGT CTG GTG CAG CCC TCA CAG ACC CTG TCC CTC ACC TGC ACT GTC TCT GGG TTC TCA CTA
ACC AAC AAT TCA GCT CTC CGA TGG AAC TGG GTT CGA CAG GCT CCA GGA AGG GGT CTG GAG TGG GCT GGA GTC ATG GCC ACA GAT
TAC AAT TCA GCT ACA GCC ACT TAC AAC CCA TCC ACT AGC ACC ATC ACT AGG GAC ACA TCC AAG AAC CAA GTT TTC TTA AAA GTT CAC ATG CAA GAC CTG CAA
TCT GAA GAC ACA GCC GTC TAT TAC TGT GCC AGA GAC GGG TAT AGC AGC TCT ACC CTC TAT GCT ATG GAT GCC TGG GGT CAA GGA
ACT TCG GTC ACC GTC TCC TCA

FIG. 8C  αD11 GRAFTED VL

```
            D   I   Q   M   T   Q   S   P   S   S   L   S   A   S   V   G   D   R   V   T   I   T   C   R
                                        OLIGO L1S
5' ACA GGC GTG CAC TCC GAC ATC CAG ATG ACC CAG TCT CCA TCT TCC CTG TCT GCA TCT GTG GGA GAC CGC GTC ACC ATC
3'                                                                              CAC CCT CTG GCG CAG TGG TAG TGT ACA GCT 5'

A   S   E   D   I   Y   N   A   L   A   W   Y   Q   Q   K   P   G   K   A   P   K   L   L   I   Y   N   T   D   T
                                                OLIGO L3S
5'                                      GCA TGG TAT CAG CAG AAG CCA GGG AAA GCT CCT AAG CTC CTG ATC TAT AAT ACA GAT ACC
3' CGT TCA CTC CTG TAA ATA TTA CGA AAT CGT ACC ATA GTC GTC TTC GGT                                                  TGG
                                                        OLIGO L2AS                                                     5'

L   H   T   G   V   P   S   R   F   S   G   S   G   S   G   T   D   Y   T   L   T   I   S   S   L   Q   P   E   D
5' TTG CAT ACA GGG GTC CCA
   AAC GTA TGT CCC CAG GGT CAG AGT GCT AAG TCA CCG TCA CCT AGA CCA TGT CTG ATA TGA GAG TCG TAT TCG GAC
                                                        OLIGO L4AS
3'                                                                  ACT CTC ACG ATA AGC CTG CAA CCT GAA GAT 3'

F   A   T   Y   F   C   Q   H   Y   F   H   Y   P   R   T   F   G   Q   G   T   K   V   E   I   K
                                        OLIGO L5S
5'                              CAC TAT TTC CAT TAT CCT CGG
   TTC GCA ACT TAT TTC TGT CAG GTG ATA AAG GTA ATA GGA GCC TGC AAG CCA GTT CCC TGG TTC CAC CTC TAG TTT GCA CTC ATC TTA
                                                                OLIGO L6AS                                              5'

AGA TCT AAC
3'          5'
```

FIG. 8D  αD11 GRAFTED VH

```
           E   V   Q   L   V   E   S   G   G   G   L   V   Q   P   G   G   S   L   R   L   S   C   A   A
                                           OLIGO H1S
5'
ACA GGC GCG CAC TCC GAG GTG CAG CTG GTG GAA TCA GGA GGT GGT CTG GTG CAG CCC GGA GGG TCC CTG CGC CTC AGC TGC A    3'
                                                                       CCC AGG GAC GCG GAG TCG ACG CGA CGG       5'
3'

S   G   F   S   L   T   N   N   V   N   W   V   R   Q   A   P   G   K   G   L   E   W   V   G   V   W
5'                                              OLIGO H3S
AGA CCG AAG AGT GAT TGG TTT TTA CAC TTG TTA AAC TGG GTT CGA CAG CCA GCT CCA GGA AAA GGT CTG GAG TGG GTG GGA GTC TGG GCT  3'
                                                                OLIGO H2AS
3'

G   A   T   D   Y   N   S   A   L   K   S   R   F   T   I   S   R   D   N   S   K   N   T   A   Y   L   Q   M
5'
GGT GGA GCC ACA GAT TAC AAT TCA GCT TTA AAG TCG AGA TTT ACT ATT TAG TCA GCG CTG TTG AGG TTC TTG TGT CGA ATG GTT TAC    3'
    CCT CGG TGT CTA ATG TTA AGT CGA AAT TCA AGC TCT AAA TGA TAA ATC AGT CGC GAC AAC TCC AAG AAC ACA GCT TAC CAA ATG ATG
                                                OLIGO H4AS
3'

N   S   L   R   A   E   D   T   A   V   Y   Y   C   A   R   D   G   Y   S   S   T   L   Y   A   M   D   A
5'                                                  OLIGO 5S
AAC AGT CTG CGC GCT GAA GAC ACA GCC GTT TAC TAC TGT GCC AGA GAC GGG GGC TAT AGC
                                                    CGG TCT CTG CCC CCG ATA TCG TCG AGA TGG GAG ATA CGA TAC CTA CGG    5'
                                                            OLIGO H6AS
3'

W   G   Q   G   T   L   V   T   V   S   S
ACC CCA GTT CCT TGA GAC CAG TGG CAG AGG AGT   3'
                                                5'
```

FIG. 8E     *OLIGOs TO SYNTHESIZE αD11 VL*

OLIGO L1S
ACA GGC GTG CAC TCC GAC ATC CAG ATG ACC CAG TCT CCA TCT TCC CTG TCT GTG GGA GAC CGC GTC ACC ATC

OLIGO L2AS
TGG CTT CTG CTG ATA CCA TGC TAA AGC ATT ATA AAT GTC CTC ACT TGC TCG ACA TGT GAT GGT GAC GCG GTC TCC CAC

OLIGO L3S
GCA TGG TAT CAG CAG AAG CCA GGG AAA GCT CCT AAG CTC CTG ATC TAT AAT ACA GAT ACC TTG CAT ACA GGG GTC CCA

OLIGO L4AS
CAG GCT GCT TAT CGT GAG AGT ATA GTC TGT ACC AGA TCC ACT GCC ACT GAA TCG TGA TGG GAC CCC TGT ATG CAA GGT

OLIGO L5S
ACT CTC ACG ATA AGC AGC CTG CAA CCT GCA ACT TTC TGT CAG CAC TAT TTC CAT TAT CCT CGG

OLIGO L6AS
CAA TCT AGA ATT CTA CTC ACG TTT GAT CTC CAC CTT GGT CCC TTG ACC GAA CGT CCG AGG ATA ATG GAA ATA GTG

FIG. 8F     *OLIGOs TO SYNTHESIZE αD11 VH*

OLIGO H1S
ACA GGC GCG CAC TCC GAG CTG GTG GAA TCA GGT GGT CTG GTG CAG CCC GGA GGG TCC CTG CGC CTC AGC TGC

OLIGO H2AS
TCC TGG AGC CTG TCG AAC CCA GTT CAC ATT GTT GGT TAG TGA GAA GCC AGA GGC AGC GCA GCT GAG GCG CAG GGA CCC

OLIGO H3S
AAC TGG GTT CGA CAG GCT CCA GGA AAA GGT CTG GAG TGG GTG GGA GTC TGG GCT GGA GCC ACA GAT TAC AAT TCA

OLIGO H4AS
CAT TTG TAA GTA AGC TGT GTT CTT GGA GTT GTC GCG GAT GGT GAA TCG GGA TTT GAG AGC TGA ATT GTA ATC TGT GGC TCC

OLIGO H5S
AAG AAC ACA GCT TAC TTA CAA ATG AAC AGT CTG CGC GCT GAA GAC ACA GCC GTT TAC TAC TGT GCC AGA GAC GGG GGC TAT AGC

OLIGO H6AS
TGA GGA GAC GGT GAC CAG AGT TCC TTG ACC CCA ATC CAT AGC ATA GAG GGT AGA GCT GCT ATA GCC CCC GTC TCT GGC

POLYNUCLEOTIDES ENCODING HUMANIZED ANTI-NGF ANTIBODIES

This application is a divisional of U.S. patent application Ser. No. 10/583,618 filed Sep. 19, 2008, which is a national stage application of PCT/IT04/00722, filed Dec. 23, 2004, which claims benefit of Italian Patent Application No. RM2003000601 filed Dec. 24, 2003. The entire contents of each of the foregoing applications are incorporated herein by this reference.

BACKGROUND

The present invention relates to a method for the humanization of antibodies, by means of determining and comparing three-dimensional structures, humanized antibodies thereby obtained and their uses in therapy and diagnostics in vivo.

The therapeutic and diagnostic application of monoclonal antibodies of animal origins in humans has fundamental contraindications especially for therapeutic regimes which necessitate for repeated administrations. In particular, murine monoclonal antibodies have a relatively short half-life and, when used in humans, lack some fundamental functional characteristics of immunoglobulins, such as complement-dependent cytotoxicity and cell-mediated cytotoxicity.

Moreover, monoclonal antibodies of non-human origin contain immunogenic amino acid sequences if injected into patients. Numerous studies have shown that after the injection of an exogenous antibody, subjects develop a rather strong immune reaction against the antibody itself (known as HAMA—human anti-mouse antibodies—reaction), completely eliminating its therapeutic usefulness, with the formation of immunocomplexes, alteration of pharmacokinetics, production of allergic reactions, etc. Moreover, considering the growing number of different monoclonal antibodies developed in mice or in other mammals (and thus antigenic for humans) for the therapy of different pathologies, treatments, also for non correlated therapies can be ineffective or even dangerous due to cross-reactivity. Although the production of so-called chimeric antibodies (variable murine regions joined to constant regions of human origin) has yielded some positive result, a significant immunogenicity problem still remains.

Humanized antibodies have at least three potential advantages with respect to antibodies of animal origin in the field of therapeutic use in humans. In the first place, the effector region, being human, can better interact with the other parts of the human immune system, destroying target cells more efficiently by means of complement-dependent cytotoxicity, or cell-mediated, antibody dependent cytotoxicity. Moreover, the human immune system does not recognize the framework or the constant region (C) of the humanized antibody as exogenous, and hence the antibody response against the humanized antibody is minimized, both relative to that against a murine antibody (totally extraneous) and relative to the response induced by a chimeric antibody (partially extraneous).

It has been reported that murine antibodies injected into humans have a much shorter half-life time than normal antibodies (Shaw et al., 1987). Humanized antibodies have a very similar half life to that of natural human antibodies, allowing less frequent administration and lower doses.

The basic principle of humanization is configured in transferring the specificity of antigen recognition, i.e. the CDR domains, in the context of a human immunoglobulin ("CDR grafting", Winter and Milstein, 1991). Several examples of humanized antibodies, produced in the attempt to solve the problem of immunogenicity, have been reported (Maeda et al., 1991; Singer et al., 1993; Tempest et al., 1994; Kettleborough et al., 1991; Hsiao et al., 1994; Baca et al., 1997; Leger et al., 1997; Ellis et al., 1995; Sato et al., 1994; Jones et al., 1986; Benhar et al., 1994; Sha and Xiang, 1994; Shearman et al., 1991; Rosok et al., 1996; Gussow & Seemann, 1991; Couto et al., 1994; Kashmiri et al., 1995; Baker et al., 1994; Riechmann et al., 1988; Gorman et al., 1991; Verhoeyen et al., 1988; Foote & Winter, 1992; Lewis & Crowe, 1991; Co et al., 1991; Co et al., 1991; Verhoeyen et al., 1991; Eigenbrot et al., 1994; Hamilton et al., 1997; Tempest et al., 1995; Verhoeyen et al., 1993; Cook et al., 1996; Poul et al., 1995; Co et al., 1992; Graziano et al., 1995; Presta et al., 1993; Hakimi et al., 1993; Roguska et al., 1996; Adair et al., 1994; Sato et al., 1993; Tempest et al., 1991; Sato et al., 1996; Kolbinger et al., 1993; Zhu and Carter, 1995; Sims et al., 1993; Routledge et al., 1991; Roguska et al., 1994; Queen et al., 1989; Carter et al., 1992).

The transcription of an antibody from animal (generally murine) to humanized entails the compromise between opposite requirements, whose solution varies case by case. To minimize immunogenicity, immunoglobulin shall maintain as much of the accepting human sequence as possible. In any case, to preserve the original binding properties, the immunoglobulin framework should contain a sufficient number of mutations in the accepting human sequence to guarantee that the conformation of the CDR regions is as similar as possible to that in the donor murine immunoglobulin. As a consequence of these opposite considerations, for many humanized antibodies a significant loss in binding affinity with respect to the corresponding murine antibodies has been reported (Jones et al., 1986; Shearman et al., 1991; Kettleborough, 1991; Gorman et al., 1991; Riechmann et al., 1988).

Currently, the most common method for the production of humanized immunoglobulin is based on the use of appropriate genomic, synthetic sequences, as well as cDNA (Reichmann et al., 1988).

The patent application EP 592106 discloses a method for the humanization of antibodies from rodents. The method is based on the identification of the amino acid residues exposed at the surface of the three-dimensional structure of the antibody to be humanized, on the identification of the amino acid residues in the same positions on the corresponding human antibody, and on the replacement of the residues identified in the sequence of the rodent antibody with those identified in the human antibody.

SUMMARY OF THE INVENTION

The authors of the present invention set up a method to obtain optimized humanized forms of immunoglobulins which are substantially not immunogenic in humans, with an approach that is consistently based on structural data, obtained experimentally, deriving from crystallographic studies. The method of the invention allows one to obtain antibodies in a form adapted to therapeutic formulation and to other medical and diagnostic applications.

The invention relates to a method fully based on structural data to conduct the first design stages (generally more subject to error) of humanization. Humanized immunoglobulins have two pairs of heterodimers between light and heavy chain, with at least one of the chains bearing one or more CDRs of animal origin, functionally bound to segments of regions of the framework of human origin. For example, CDRs of animal origin, together with amino acid residues, naturally associated, also of animal origins, are introduced in framework regions of human origin, to produce humanized immunoglobulins able to bind the respective antigens, with affinities comparable to the affinities of the original immunoglobulins of animal origin.

The method of the invention led to humanized antibodies suitable for therapeutic and diagnostic applications. In particular, humanized immunoglobulins have been obtained, derived from anti-TrkA antibodies (Patent EP 1181318) and from anti-NGF antibodies able to bind with high specificity respectively TrkA and NGF, neutralizing the interaction between ligand and receptors. Such molecules are useful for the treatment of tumors which depend on NGF/TrkA, of chronic pain and of inflammatory forms, and for diagnostic purposes, for in vivo imaging, e.g. on TrkA positive tumors, or on basal forebrain as a precocious marker of Alzheimer's Disease. In particular, humanized anti-TrkA antibodies find specific therapeutic and diagnostic application in the inflammatory forms of the urinary tract and of the pelvic region. In particular, humanized anti-NGF antibodies find specific therapeutic and diagnostic application in pathologies induced by HIV virus, to induce apoptosis of immune cells, such as HIV infected, NGF dependent macrophages.

Therefore, an object of the present invention is to provide a method for the humanization of the VH and VL variable regions of a animal antibody of known sequence, comprising the steps of:
a) if not available, obtaining the crystallographic structure of the VH and VL regions of the animal antibody;
b) pre-selecting a series of 0 to n possible frameworks acceptors of human origin or humanized antibodies, whose structure was determined experimentally with a resolution of no less than 3 Å, based on the highest level of homology and identity with the primary sequence of the framework of the animal antibody;
c) conducting a structural comparison between the VH and VL variable regions of the animal antibody and the regions VH and VL obtained in b), respectively and calculating for each comparison the RMS, to identify the region VH and the region VL of human origin with the smaller RMS;
d) inserting in appropriate position the sequences of the regions CDR of the animal antibody in the human sequences identified in c);
e) if necessary, retromutate one or more amino acid residues of the human VH and VL regions identified in c).

Preferably, the modifications of the antibody take place with recombining DNA techniques.

In a preferred embodiment, the animal antibody is an anti-NGF antibody, preferably it is the alpha D11 antibody, and the humanized sequences essentially have the following VH sequences: Hum alpha D11

```
                                       (SEQ ID No. 17)
VH, EVQLVESGGGLVQPGGSLRLSCAASGFSLTNNNVNWVRQAPGKGLE

WVGGVWAGGATDYNSALKSRFTISRDNSKNTAYLQMNSLRAEDTAVYYC

ARDGGYSSSTLYAMDAWGQGTLVTVSS,
``` and VL: Hum alpha D11Vk,

```
                                       (SEQ ID No. 18)
DIQMTQSPSSLSASVGDRVTITCRASEDIYNALAWYQQKPGKAPKLLIY

NTDTLHTGVPSRFSGSGSGTDYTLTISSLQPEDFATYFCQHYFHYPRTF

GQ GTKVEIK.
```

In an alternative embodiment, the animal antibody is an anti-TrkA antibody, preferably it is the alpha MNAC13 antibody, and the humanized sequences essentially have the following sequences: VH: HumMNAC13VH,

```
                                       (SEQ ID No. 37)
EVQLLESGGGLVQPGGSLRLSCAASGFTFSTYTMSWARQAPGKGLEWVA

YISKGGGSTYYPDTVKGRFTISRDNSKNTLYLQMNSLRAEDSAVYYCAR

GAMFGNDFFFPMDRWGQGTLVTVSSA,
``` and VL: Hum MNAC13Vk,

```
                                       (SEQ ID No. 38)
DIVLTQSPSSLSASVGDRVTITCSASSSVSYMHWYQQKPGQAPKLLIYT

TSNLASGVPSRFSGSGSGTDYTLTISSLQPEDVATYYCHQWSSYPWTFG

GG TKVEIK.
```

The humanized immunoglobulins of the present invention (or derived fragments which maintain binding activities and other compounds which can be derived) can be produced by means of known recombining DNA techniques. As a function of the subsequent use of the humanized immunoglobulins, transgenic animals or transfected cells can be used for their expression, preferably immortalized eukaryotic cells (such as myeloma or hybridoma cells), but also prokaryotic hosts, insect or vegetable cells. The coding polynucleotides for the resulting sequences of the humanized immunoglobulins can also be obtained by synthesis.

The humanized immunoglobulins of the present invention can be used alone or in combination with other therapeutic agents. In case of use as anti-tumor agents, a chemotherapeutic agent will be preferred, which may vary depending on the pharmacological application (such as anthracyclin, paclitaxel, cisplatin, gemcytabin, non steroidal and corticosteroid anti-inflammatory drugs, or immunosuppressants), as well as with all drugs currently applied in the therapy of each specific pathology. Humanized immunoglobulins or their complexes can be prepared in the form of pharmacologically acceptable dosages, which vary depending on the type of administration.

DEFINITIONS

The term "substantially identical" within the context of two polynucleotides or polypeptides (respectively sequences of coding DNA for humanized immunoglobulins or amino acid sequences of humanized immunoglobulins, or portions thereof) refers to two or more sequences which have a minimum of 80% (preferably 90-95% or more) of identity in the nucleotide or amino acid residues, when compared and aligned with maximum correspondence. Generally, the "substantial identity" is verified in regions that are at least 50 residues long, more preferably on a region of at least 100 residues or, in optimal conditions, on over 150 residues or on the complete sequences. As described below, any two sequences of antibodies can be aligned in only one way, using Kabat's numbering scheme. Consequently, for antibodies the percentage of identity has a unique and well defined meaning. The amino acids of the variable regions of the heavy and light chains of mature immunoglobulins are designated Hx and Lx, with x being the number that designates the position of the amino acid according to Kabat's numbering scheme, Sequences of Proteins of Immunological Interest (National Institutes of Health, Bethesda Md., 1987, 1991). Kabat has determined a list of amino acid sequences of antibodies for each subgroup as well as a list of the most frequent amino acids in each position in each subgroup to generate a consensus sequence. Kabat uses a method to assign a number to each amino acid of each sequence in the list and this method for assigning the number of each residue has become a standard method in the field. Kabat's scheme can be extended to other antibodies not present in his study, aligning the antibody in question with one of the consensus sequences identified by Kabat, basing on the preserved amino acids. Use of Kabat's numbering scheme allows one to easily identify the amino acids in equivalent positions in different antibodies. For example, an amino acid in L10 position in an antibody of human origin occupies the equivalent position of an amino acid in L10 position in an antibody of murine origin.

It is well known that the basic structural unit of an antibody comprises a tetramer. Each tetramer is constituted by two identical pairs of polypeptide chains, each of which is composed by a light chain (25 KDa) and by a heavy chain (50-75 KDa). The amino-terminal region of each chain includes a variable region of about 100-110 or more amino acids, which is involved in antigen recognition. The carboxy-terminal region of each chain comprises the constant region that mediates the effector function. The variable regions of each pair of light and heavy chains form the binding site of the antibody. Therefore, an intact antibody has two binding sites.

Light chains are classified as γ or λ. Heavy chains are classified as γ, μ, α, ε and they define the isotype of the antibody as respectively IgG, IgM, IgA, IgD, or IgE. Inside both the light and the heavy chain, the variable and constant regions are joined by a "J" region of about 12 amino acids or more, whilst only the heavy chains include a "D" region of about 10 amino acids (Paul, 1993).

The variable regions of each pair of light and heavy chains form the binding site of the antibody. They are characterized by the same general structure constituted by relatively preserved regions called frameworks (FR) joined by three hypervariable regions called complementarity determining regions (CDR) (Kabat et al., 1987; Chothia and Lesk, 1987). The CDRs of the two chains of each pair are aligned by the framework regions, acquiring the function of binding a specific epitope. Starting from the amino-terminal region towards the carboxy-terminal region, the variable domains both of the light chain and of the heavy chain comprise and alternation of FR and CDR regions: FR, CDR, FR, CDR, FR, CDR, FR; consequently, both the heavy chain and the light chain are characterized by three CDRs, respectively CDRH1, CDRH2, CDRH3 and CDRL1, CDRL2, CDRL3. Amino acid assignment to each region was conducted according to the definitions by Kabat (1987 and 1991) and/or Chothia & Lesk (1987), Chothia et al. (1989).

Preferably, the analogs of the exemplified humanized immunoglobulins differ from the original immunoglobulins due to conservative amino acid substitutions. In order to classify the amino acid substitutions as conservative or non conservative, amino acids can be grouped as follows:
Group I (hydrophobic lateral chains): M, A, V, L, I;
Group II (neutral hydrophilic lateral chains): C, S, T, N, Q;
Group III (acid lateral chains): D, E;
Group IV (basic lateral chains): K, R;
Group V (residues that influence the orientation of the main chain): G, P;
Group VI (aromatic lateral chains): F, Y, W.

Conservative amino acid substitutions are substitutions between amino acid of the same class, whilst non conservative amino acid substitutions entail an exchange between members of different classes.

The term "epitope" includes every protein determinant able to bind an immunoglobulin in specific fashion. Generally, epitopes are formed by sets of chemically active surfaces of macromolecules, such as lateral chains of amino acid or sugars and they generally have specific chemical-physical and conformational characteristics.

The term "immunoglobulins" refers to proteins which consist of one or more polypeptides coded by genes of the immunoglobulins. Immunoglobulins can exist in a variety of forms, in addition to the tetramer antibody form: for example, they include fragments Fv, Fab e F(ab') as well as bifunctional hybrid antibodies (Lanzavecchia et al., 1987) and single chain Fv fragments (Hood et al., 1984; Harlow and Lane, 1988; Hunkapiller and Hood, 1986).

Chimeric antibodies are antibodies whose genes for the light and heavy chains have been engineering starting from gene regions of immunoglobulins belonging to different species. For example, variable segments (V) of the genes of a monoclonal mouse antibody can be joined to constant segments (C) of an antibody of human origin. A therapeutic chimeric antibody, therefore, is a hybrid protein which consists of the domain V which recognizes the antigen deriving from a mouse antibody and in the effector domain C deriving from a human antibody (although other combinations of mammal species can be used).

The term "framework" refers to those portions of the variable regions of the light and heavy chain of the immunoglobulins that are relatively preserved (not belonging to the CDRs) between different immunoglobulins within a species, according to Kabat's definition. Hence, a human framework is a framework region that is substantially identical (at least 85% or more) to the framework that is naturally found in human antibodies.

The term "humanized immunoglobulin" refers to an immunoglobulin which comprises a human framework and at least one CDR deriving from a non human antibody and in which each constant region present is substantially identical to a region of human immunoglobulin (at least 85%, preferably at least 90-95% identical). Hence, all the parts of a humanized immunoglobulin except the CDR are substantially identical to the corresponding regions of one or more sequences of natural human immunoglobulins. For example, the chimeric antibodies, constituted by variable mouse regions and constant regions of human origin, are not included among the humanized immunoglobulins.

Figure 1D:
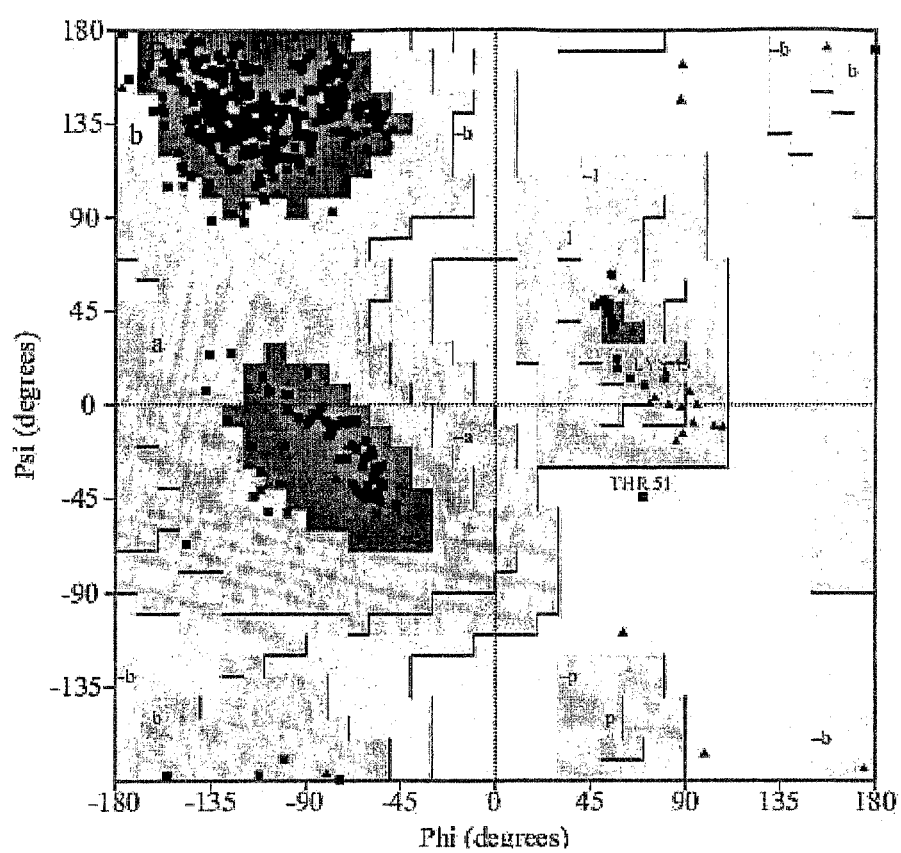
FIG. 1: A) depicts the analysis by means of polyacrylamide in denaturing conditions (SDS-PAGE 12%) and coloring with Coomassie Blue of the result of the purification of the Fab fragment of the MNAC13 antibody (well 1: sample of MNAC13 antibody digested proteolytically with papaine; well 2: fraction bound to the DEAE Sephacell ionic exchange resin and eluted with NaCl 250 mM; well 3: molecular weights; well 4: Fab fragment of the purified and concentrated MNAC13 antibody); B) depicts a typical crystal of the Fab fragment of the MNAC13 antibody C) depicts a high resolution diffraction spectrum obtained with a crystal of the Fab fragment of the MNAC13 antibody; D) is a Ramachandran chart of the torsion angles of the main chain of the heavy and light domains of the Fab fragment of the MNAC13 antibody.

FIG. 3: A) B) C) D) depict distributions of the humanized or human origin antibodies (named using the PDB codes of their crystallographic structures) according to the three analyzed variables; E) F) illustrate deviations of the humanized or human origin antibodies from the hypothetical optimal value of MNAC13 (calculated both considering the degree of overall identity and of homology—in blue—and framework level—in magenta—) G) depicts the structural alignment with the Fv fragment of MNAC13 of the respective regions of the humanized or human origin antibodies, selected according to the degree of identity and homology with the murine antibodies and to the degree of resolution of available structural data; H) I) depict the structural alignment with the Fv fragment of MNAC13 (shown in cyan) of the respective region of the selected humanized antibody 1AD0 (shown in red) in H); and of the model of the antibodies resulting after CDR grafting (shown in yellow at the framework level, in white at the CDR level) in I); L) depicts a model of the Fv fragment of the MNAC13 humanized antibody obtained as a result of the identification of putative retro-mutations in the chosen framework (human origin residues are shown in green and murine origin residues are shown in magenta).

FIG. 4: A) B) C) D) depict distributions of the humanized or human origin antibodies (named using the PDB codes of their crystallographic structures) according to the three analyzed variables; E) F) depict deviations of the humanized or human origin antibodies from the hypothetical optimal value of αD11 (calculated both considering the degree of overall identity and of homology—in blue—and framework level—in magenta—) G) depict the structural alignment with the Fv fragment of αD11 of the respective regions of the humanized or human origin antibodies, selected according to the degree of identity and homology with the murine antibodies and to the degree of resolution of available structural data; H) I) depict the structural alignment with the Fv fragment of αD11 (shown in cyan) of the respective region of the selected humanized antibody 1JPS (shown in red) in H); and of the model of the antibodies resulting after CDR grafting (shown in yellow at the framework level, in white at the CDR level) in I); L) depicts a model of the Fv fragment of the αD11 humanized antibody obtained as a result of the identification of putative retro-mutations in the chosen framework (human origin residues are shown in cyan and murine origin residues are shown in purple).

FIG. 5: depicts the alignment of the primary structures of the variable regions of the heavy chain (A) and of the light chain (B) respectively of MNAC13 (SEQ ID No. 22, SEQ ID No. 24), of the humanized antibody selected for humanization (1AD0; SEQ ID No. 39, SEQ ID No. 40), of the humanized form of MNAC13 after CDR grafting on the framework of 1AD0 and of the described retro-mutations and mutations (Hum MNAC13: SEQ ID No. 37, SEQ ID No. 38). CDRs are highlighted in the sequence of the humanized form of the two chains of MNAC13 by underlined character.

FIG. 6: depicts the alignment of the primary structures of the variable regions of the heavy chain (A) and of the light chain (B) respectively of D11 (SEQ ID No. 2, SEQ ID No. 4), of the humanized antibody selected for humanization (1JPS; SEQ ID No. 19, SEQ ID No. 20), of the humanized form of αD11 after CDR grafting on the framework of 1AD0 and of the described retro-mutations and mutations (Hum αD11; SEQ ID No. 17, SEQ ID No. 18). CDRs are highlighted in the sequence of the humanized form of the two chains of αD11 by underlined character.

FIG. 7: A) depicts the nucleotide sequence of the cDNA of the variable region of the light chain of the murine form of MNAC13 (SEQ ID No. 23); B) depicts the nucleotide sequence of the cDNA of the variable region of the heavy chain of the murine form of MNAC 13 (SEQ ID No. 21); C) and E) depict the sequences of the oligonucleotides designed to obtain the humanized form of the variable region of the light chain of MNAC13 (SEQ ID No. 38): L1S: SEQ ID No. 31; L2AS: SEQ ID No. 32; L3S: SEQ ID No. 33; L4AS: SEQ ID No. 34; L5S: SEQ ID No. 35; L6AS: SEQ ID No. 36, by means of the overlap-assembly PCR technique, shown together with the corresponding translation into amino acid sequence; D and F) depict the sequences of the oligonucleotides designed to obtain the humanized form of the variable region of the heavy chain of MNAC13 (SEQ ID No. 37): H1S: SEQ ID No. 25; H2AS: SEQ ID No. 26; H3S: SEQ ID No. 27; H4AS: SEQ ID No. 28; H5S: SEQ ID No. 29; H6AS: SEQ ID No. 30, by means of the overlap-assembly PCR technique, shown together with the corresponding translation into amino acid sequence.

FIG. 8: A) depicts the nucleotide sequence of the cDNA of the variable region of the light chain of the rat form of αD11 (SEQ ID No. 3); B) depicts the nucleotide sequence of the cDNA of the variable region of the heavy chain of the murine form of αD11 (SEQ ID No.1); C) and E) depict the sequences of the oligonucleotides designed to obtain the humanized form of the variable region of the light chain of αD11 (SEQ ID No. 18): US: SEQ ID No. 11; L2AS: SEQ ID No. 12; L3S: SEQ ID No. 13; L4AS: SEQ ID No. 14; L5S: SEQ ID No. 15; L6AS: SEQ ID No. 16, by means of the overlap-assembly PCR technique, shown together with the corresponding translation into amino acid sequence; D and F) depict the sequences of the oligonucleotides designed to obtain the humanized form of the variable region of the heavy chain of D11 (SEQ ID No. 17): H1S: SEQ ID No. 5; H2AS: SEQ ID No. 6; H3S: SEQ ID No. 7; H4AS: SEQ ID No. 8; H5S: SEQ ID No. 9; H6AS: SEQ ID No. 10, by means of the overlap-assembly PCR technique, shown together with the corresponding translation into amino acid sequence.

FIG. 9: depicts maps of the plasmids used to clone the sequences of the humanized variable regions of both antibodies obtained by overlap-assembly PCR. A) illustrates pVLexpress for the variable domain of the light chain, B) illustrates pVHexpress for the variable domain of the heavy chain, C) illustrates the plasmid resulting from cloning in pVLexpress the variable region of the light chain of each humanized antibody, D) illustrates alternative constructs obtained as a result of cloning in pVHexpress the variable region of the heavy chain of each humanized antibody: 1) for the expression in intact immunoglobulin form IgG1, 2) for expression in Fab fragment form, 3) for expression in immunotoxin form.

Figure 10A:
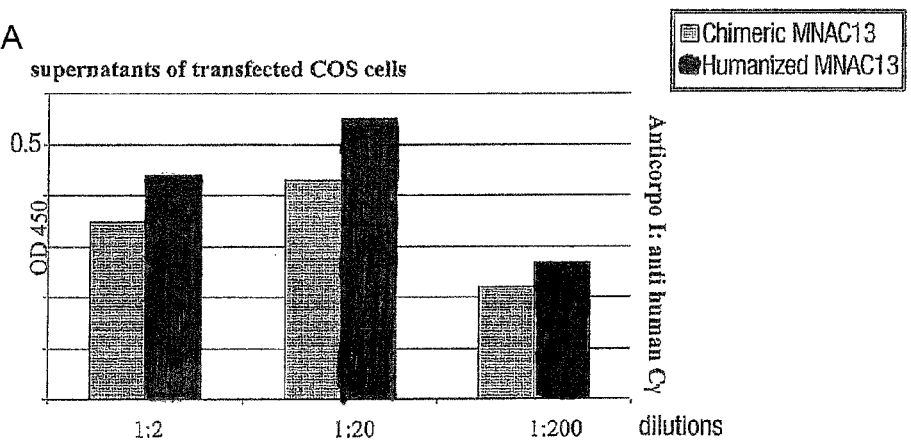

FIG. 10: depicts a comparison of the binding activity of the MNAC13 antibody in chimeric form and in humanized form by means of ELISA assay, conducted immobilizing on plastic TrkA in immunoadhesin form: A) depicts a comparison between serial dilutions of supernatants of transfected COS cells, subsequently concentrated; B) depicts a comparison between serial dilutions of supernatants of transfected COS cells purified by means of G sepharose protein.

Figure 11:
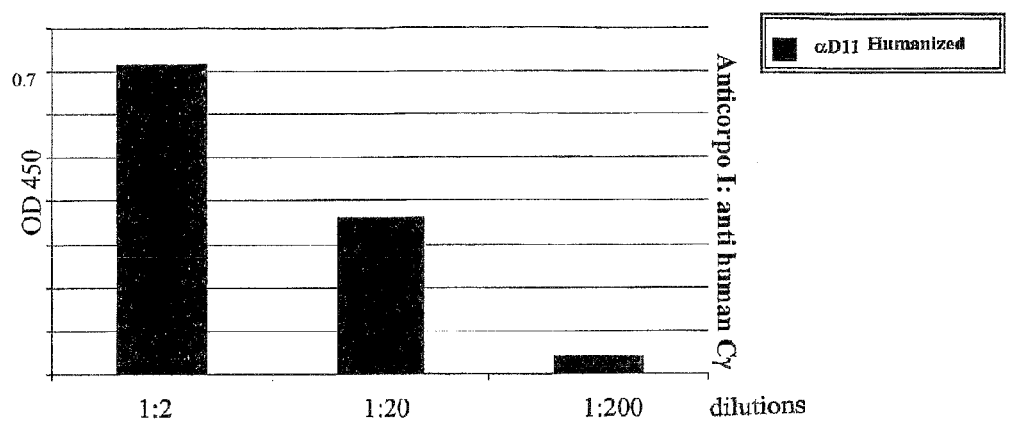

FIG. 11: depicts the results of an assay of the binding activity of the αD11 antibody in humanized form by means of ELISA assay, conducted immobilizing on plastic NGF.

DETAILED DESCRIPTION OF THE INVENTION

The method is based on the high resolution structural comparison for the humanization of antibodies of in vivo therapeutic and diagnostic interest. Moreover, humanized immunoglobulins are provided, able to be reactive specifically against the respective antigens (i.e. NGF neurotrophin and its TrkA receptor). Humanized immunoglobulins have a framework of human origin and they have one or more complementarity determining regions (CDRs) deriving from each original immunoglobulin (i.e. αD11, a rat immunoglobulin, reactive specifically against NGF and MNAC13, a murine immunoglobulin, which specifically recognizes TrkA). Therefore, the immunoglobulins of the present invention, which may be easily produced on a large scale, find therapeutic application not only in the therapy of NGF/TrkA dependent tumor forms, but also in the treatment of chronic pain and inflammatory forms. Moreover, the specific humanized immunoglobulin for the receptor has an additional diagnostic application for in vivo imaging both on TrkA positive tumors and on cells of the basal forebrain (as a precocious marker of Alzheimer's disease).

The present invention uses the recombinant segments of DNA coding the CDR regions of the light and/or heavy chain, able to bind an epitope of interest both on NGF and on TrkA, as in the case of the monoclonal antibodies αD11 and MNAC13 (respectively rat and mouse). The coding DNA segments for these regions are joined to the DNA segments coding appropriate framework regions of human origin. The DNA sequences that code for the polypeptide chains comprising the CDRs of the light and heavy chain of the monoclonal antibodies MNAC13 and αD11 are included in FIGS. 7A, 7B and 8A, 8B respectively. Because of the degeneration of the genetic code and of the substitutions of non critical amino acids, the DNA sequences can easily be modified. Moreover, DNA segments typically include an additional control sequence for the expression, operatively bound to the coding sequences for humanized immunoglobulins and comprising regions of heterologous or naturally associated promoters. Preferably, the expression control sequences are systems with eukaryotic promoters in vectors able to transform or transfect eukaryotic host cells, but prokaryotic control sequences can be used as well. Once the vector is incorporated in the appropriate host, the host is maintained in suitable conditions to assure a high level of expression. A further purification follows of the light and heavy chains individually in the form of dimers, of intact antibodies or of other forms of immunoglobulins.

The sequences of coding DNA for the human constant region can be isolated by means of well known procedures from a variety of human cells, but preferably starting from immortalized B cells. The CDRs in the immunoglobulins of the present invention are similarly derived from the monoclonal antibodies αD11 and MNAC13 able to bind respectively NGF and TrkA and products respectively in rat and mouse. Host cells suitable for the expression and the secretion immunoglobulins can be obtained from many sources such as the American Type Culture Collection (Catalogue of Cell Lines and Hybridomas, Fifth edition (1985) Rockville, Md., USA). Preferably, the CDRs incorporated in humanized antibodies have sequences corresponding to those of the CDRs of αD11 and MNAC13 and can include degenerated nucleotide sequences coding the corresponding amino acid sequences of the antibodies themselves.

Generally, the humanization design procedure is cyclical and iterative and it comprises:

The analysis of the amino acid sequence of the murine antibody;
The modeling of the corresponding Fv region;
The analysis and selection of the amino acid sequence of the acceptor framework of the human antibody;
The identification of putative retro-mutations in the selected framework;
The design and the actual construction of the humanized antibody;
The verification, by means of in vitro and/or in vivo assays, of the maintained affinity and specificity of the binding.

If these activities are negatively influenced by the human framework, it will be necessary to change the selection of the framework of the acceptor human antibodies, or to introduce compensating mutations.

Even if the choice of the human framework is configured as the most critical phase of the cycle, no general rules have been established to date. This depends on the fact that the advantages of the various choices (in terms of immunogenicity in the patient) have not been accurately studied from the clinical viewpoint. Therefore, to operate the correct choice of the framework, only a series of approaches are available, which must be combined with the results obtained previously.

In particular, it is possible to use fixed frameworks (usually NEW for the heavy chain and REI for the light chain, since their structures have been available for a long time). Another approach provides for the use of the frameworks found to be the most homologous in terms of sequence with the antibody to be humanized. There are many databases to search for homologous human antibodies: the choice generally takes into account the length of the CDRs, the identity at the level of canonical residues and of the residues at the interface level, in addition to a higher percentage of identify between the sequences of the donor and of the acceptor. For a comparison between these two methods, see Graziano et al. (1995).

Moreover, according to a variant of the second approach the light chain and the heavy chain can be chosen from two different human antibodies characterized by a higher sequence homology. This approach was proposed by Riechmann et al. (1988) and by Shearman et al. (1991). In this regard, in general, light and heavy chains deriving from the same antibody have a higher probability of associating correctly, forming a functional binding site, with respect to light and heavy chains deriving from different antibodies, although the fact that the interface between the two chains is quite preserved can equally assure a correct interaction. For a comparison between these two methods, see Roguska et al. (1996 and 1996)

Limiting the approach to a framework deriving from a particular human antibody can entail the risk of incurring in somatic mutations which produce immunogenic epitopes even if the frameworks are of human origin. An alternative approach is to use frameworks based on human consensus sequences, where idiosyncratic somatic mutations have been eliminated. The two approaches have been compared: in one case, no difference in binding avidity was noted (Kolbinger et al., 1993), in another one instead the binding proved superior in the case of individual frameworks (Sato et al., 1994).

In any case, the consensus sequences themselves are artificial and therefore, even if they have no idiosyncratic residues, they can create non natural motives which are immunogenic. The alternative (Rosok et al., 1996) is to use germline human sequences collected in the V-BASE database.

The non natural juxtaposition of the murine CDR regions with the variable regions of the framework of human origin can give rise to conformational limits not represented in nature which, unless they are corrected by the substitution of particular amino acid residues, determine the loss of binding affinity. The selection of the amino acid residues to be substituted is partially determined by means of computer modeling. Hardware and software are available to produce three-dimensional images of immunoglobulin molecules. In general, molecular models are produced starting from already resolved crystallographic structures of immunoglobulin domains or chains. The chains to be modeled are compared based on the amino acid resemblance with chains or domains of resolved three-dimensional structures and the chains or the domains, which show the highest resemblance in terms of sequence, are selected as starting points in the construction of the molecular model. However, the prediction of the antibody structure is not always accurate. In particular, the third CDR region is difficult to model and it always represents a point of uncertainty in the structural prediction of an antibody (Chothia et al., 1987). For this reason, as a rule humanized antibodies, as a first approximation, have far less binding affinity and/or specificity towards the antigen than the starting monoclonal antibody. This requires many successive cycles of point mutations in the attempt to reconstitute the properties of the starting antibody, with a trial and error procedure that cannot be completely rationalized.

Considering the growing number of high resolution X-ray structures both of available human and humanized antibodies, the intent was to avoid the uncertainties and ambiguities deriving from use of computer modeling, obtaining high resolution structural data for the Fab fragments of both the antibodies of the invention by means of X-ray crystallography. For this purpose, both antibodies were purified from hybridoma, treated proteolytically with papaine (a protease that cuts at the level of the junction between CH1 and CH2 domain of the heavy chain) which gives origin to the Fab fragments. As a result of the additional purification, both Fab fragments were crystallized and from two databases (low and high resolution), it was possible to solve the structures with the Molecular Substitution method and subsequently to refine them. The approach proposed by the invention, based on structural data obtained experimentally, provides a much more solid and rational starting point, both in the critical phase of the selection of the framework of the acceptor human antibody, and for the identification of putative retro-mutations in the framework selected within the humanization process of both neutralizing antibodies.

Amongst the various reported criteria which can guide the selection of the human antibody framework, the one used was the degree of identity between the antibody of murine and human origin at the primary sequence, to extend and complete its results with an analysis based on structural alignment. A compared analysis of the corresponding structures associated to the original criterion assures a much more accurate comparison and consequently a greater probability that the resulting humanized antibody can preserve the characteristics of affinity and specificity of the original murine antibody. Consequently, the strategy employed combines the information deriving from the analysis and comparison of amino acid sequences, both in terms of degree of identity and of level of homology, with the comparison of the respective three-dimensional structures.

In particular, the information deriving from the optimal alignment of the primary structures has a dual role. In the first place, this analysis allows to reduce the number of possible tertiary structures to be compared, limiting itself to those characterized by a high degree of homology and identity. Among these sequences characterized by an optimal alignment at the primary structure level and for which structural data are available, a further selection was conducted, concentrating only on the resolved structures with high resolution or otherwise with resolution comparable to that of the structures obtained by us (i.e. no greater than 2.5 Å). This approach assures a much more accurate alignment of the tertiary structures and much more significant estimates of the structural differences, expressed in RMS (root mean square deviation: square root of the mean square deviation; Carugo and Pongor, 2001 and 2003). Low resolution data provide rather indicative, and definitely less precise information on the actual relative position of each individual atom in space.

To assess the degree of superposition of each individual structure, of human origin or engineered, the RMS was calculated between atoms of alpha carbon constituting the respective amino acid skeletons, not considering atom pairs with an RMS exceeding 2 Å. From this analysis, an information is obtained which must therefore take into account not only the diversity between the structures (expressed by the value of RMS), but also the percentage of atoms of alpha carbon actually employed in calculating each RMS.

These tertiary structure level resemblance data were associated to the comparative analysis of the primary sequences both in terms of identity and of homology.

It is hence deduced that the selection of the optimal framework for humanization is configured as a three-variable problem, which can thus be represented in space, both when associating the homology level and the degree of identity to the structural alignment. This type of analysis was then conducted also reducing the regions in question in the two types of alignment to the regions of the respective frameworks. Comparing the distributions of the antibodies considered in the space of the three analyzed variables (respectively, value of RMS, percentages of atoms on which RMS was calculated and a similitude index between primary structures, i.e. percentage of overall identity, of overall homology, of identity at the framework level, of homology at the framework level) with the optimal position in the space of the three variables that each antibody would occupy if it were of human origin, it is possibly clearly to identify the human origin antibody that most approaches this ideal position at the level of primary and tertiary structure. To rationalize this result, in each of the four analyses the deviations from the hypothetical optimal position are calculated for each position of the humanized or human origin antibodies considered.

On the basis of this method of selection, it is possible to choose the acceptor framework in the subsequent process of CDR grafting for the humanization of a given antibody. In general, it is necessary to minimize the substitutions of amino acid residues of human origin with residues of murine origin, for the introduction of murine residues increases the risk that the antibody will induce a HAMA response in the human patient. On the other hand, the complementarity determining regions (CDRs) contain the residues with the greater probability of interacting with the antigen and for this reason they must be maintained in the humanized antibody. They are defined by means of the sequence according to Kabat or by means of the structure according to Chothia. The advantage of using the second system to define them is that in general the CDRs are shorter and hence the humanized antibody is constituted by a lesser fraction of xenogenic fragments. In any case it has been demonstrated that generally following Kabat's definitions it is possible drastically to reduce the number of cycles required for humanization. Once the CDRs are defined, it is necessary to identify the canonical classes (defined by Chothia and Lesk) to which they belong and subsequently maintain the canonical residues in the humanized antibodies.

It is also essential to analyze the residues that mediate the interaction between the light chain and the heavy chain of the variable domains (Table 1), maintaining any unusual residues in the humanized antibody (Singer et al., 1993; Daugherty et al.; 1991; De Martino et al., 1991).

Moreover, further amino acids to be maintained are selected based on their possible influence on the conformation of the CDRs and/or on the interaction with the antigen. When the amino acid differs between the framework of animal origin and the equivalent acceptor framework of human original, the amino acid of the acceptor framework should be substituted by the equivalent murine residue, if it is reasonable to expect that the amino acid is in direct non covalent contact with the antigen, or is adjacent to a CDR region, or in any case interacts with a CDR region (it is situated within 4-6 Å from a CDR region).

TABLE 1

Residues that mediate the interaction between the light chain and the heavy chain of the variable domains

| LIGHT VARIABLE CHAIN L | | | HEAVY VARIABLE CHAIN H | | |
|---|---|---|---|---|---|
| Kabat Position | Mouse | Human | Kabat Position | Mouse | Human |
| 34 | H678 N420 A408 Y147 E114 | A531 N147 D66 | 35 | H1001 N636 S402 E184 | S527 H340 G167 A143 |
| 36 | Y1653 F198 L96 | Y748 F80 | 37 | V2336 I200 | V1037 I477 L27 |
| 38 | Q1865 H47 | Q799 H22 | 39 | Q2518 K67 | Q1539 R16 |
| 44 (A) | P1767 V132 I40 | P839 L5 | 45 (A) | L2636 P16 | L1531 P24 |
| 46 | L1381 R374 P97 | L760 V37 | 47 | W2518 L64 Y50 | W1534 Y21 |
| 87 | Y1457 F448 | Y795 F41 | 91 | Y2149 F479 | Y1429 F116 |
| 89 | Q1170 L206 F144 | Q687 M107 | 93 | A2202 T222 V102 | A1346 T90 V71 |
| 91 | W376 S374 G356 Y295 H182 | Y404 R115 S105 A84 | 95 | Y399 G375 S340 D340 R226 | D268 G266 R109 E100 |
| 96 (A) | L537 Y380 W285 | L134 Y215 F78 W73 I71 | 100k (A) | F1285 M450 | F540 M109 L33 |
| 98 (A) | F1724 | F654 | 103 (A) | W1469 | W323 |

In particular, a further analysis involves other residues which define the so-called Vernier zone, a zone that stabilizes the structure of the CDRs; it is important to maintain the characteristics of this region.

Other residues which are candidates for mutation are amino acids of the acceptor framework which are unusual for a human immunoglobulin in that position. These residues can be substituted with amino acids deriving from the equivalent position of more typical human immunoglobulins or alternatively residues originating from the equivalent position of the donor framework can be introduced into the acceptor framework when said amino acids are typical for the human immunoglobulins in those particular positions.

Moreover, again on the basis of the consensus sequences of human immunoglobulins, mutations are introduced in the humanized form which insert residues preserved in the human instead of the unusual residues present both in the donor and in the acceptor framework.

The respective pairs of crystallographic structures are then modified, first effecting the grafting of the CDRs of animal origin in the human frameworks. Then, all the mutations and retro-mutations described above are introduced. The modified structures are then assembled in composite immunoglobulins. The resulting models are refined by minimizing mechanical energy (in terms of torsion angles and binding angles and distances) using the force field.

For all other regions, different from the specific amino acid substitutions discussed above, the framework regions of the humanized immunoglobulins are usually substantially identical to the framework regions of the human antibodies from which they were derived. In any case in these engineered proteins obtained by grafting, the framework regions can vary relative to the native sequence at the primary structure level due to many amino acid substitutions, deletions or insertions, terminal or intermediate, and other changes. Naturally, most of the residues in the framework region brings a very small or even non-existent contribution to the specificity or affinity of an antibody. Therefore, many individual conservative substitutions in the residues of the framework can be tolerated without appreciable variations of the specificity or affinity in the resulting humanized immunoglobulin. In general, nevertheless, such substitutions are not desirable. It is possible to obtain modifications in the nucleotide sequence with a variety of widely employed techniques, such as site-specific mutagenesis (Gillman & Smith, 1979; Roberts et al., 1987).

Alternative, polypeptide fragments can be produced, comprising only a part of the primary structure of the antibody, which fragments retain one or more peculiar activities of the immunoglobulins (e.g., the binding activity). These polypeptide fragments can be produced by means of proteolytic digestion starting from intact antibodies or inserting stop codons in the desired positions in the carriers bearing the coding DNA sequences for the variable regions of the heavy and light chain by means of site specific mutagenesis (in particular after the CH1 region to produce Fab fragments or after the hinge region to produce (Fab')$_2$ fragments. Antibodies in the form of scFv can be obtained by joining the variable regions of the heavy chain and of the light chain by means of a linker (Huston et al., 1988; Bird et al., 1988). The Fv or Fab fragments can be expressed in E. coli (Buchner and Rudolph, 1991; Skerra et al., 1991) or also in eukaryotic cells, preferably mammal derived. Considering that like many other genes, the genes of the immunoglobulin super family contain distinct functional regions, each characterized by one or more specific biological activities, the genes can be fused to functional regions deriving from other genes (e.g. enzymes) to produce fusion proteins (e.g. immunotoxins) provided with new properties.

The expression of humanized immunoglobulin sequences in bacteria can be used to select humanized immunoglobulin sequences, characterized by higher affinity mutagenizing the CDR regions and producing phage libraries for phage display. Using these libraries, it is possible to perform a screening in the search for variants at the level of the CDRs of the humanized immunoglobulins that have a higher affinity and/or binding specificity for the antigens. Methods to obtain phage-display libraries bearing sequences of the variable regions of immunoglobulins have been amply reported (Cesareni, 1992; Swimmer et al., 1992; Gram et al, 1992; Clackson et al., 1991; Scott & Smith, 1990; Garrard et al., 1991). The sequences resulting from the variants of humanized immunoglobulins, whose CDRs were thus remodeled, are subsequently expressed in a host that is suitable to assure a high expression thereof.

As stated above, the DNA sequences are expressed in the host cells after being operatively bound (i.e. positioned in such a way as to assure their functionality) to expression control sequences. These carriers can typically be replicated in the host organism as episomes or as an integral part of the chromosome DNA. Commonly, the expression carriers contain a selectable marker to allow one to identify the cells that have been transformed with the DNA sequences of interest.

For the production of the humanized immunoglobulins of the invention in recombinant form of scFv or in Fab form, prokaryotic systems are preferred. *E. coli* is one of the prokaryotic hosts that is particularly useful for cloning the DNA sequences of the present invention. Moreover, a great number of well characterized promoters is available, e.g. lac or trp operon or β-lactamase or λ phage. Typically, these promoters control expression and bear binding site for the ribosome, for the correct start and finish of transcription and translation. It is possible to increase the half-life of the humanized immunoglobulins of the invention produced in prokaryotic systems by conjugation with polyethylene glycol (PEG).

Other single-cell organisms, such as yeasts, can be used for expression. The host of choice is *Saccharomyces*, using suitable carriers provided with expression control, replication termination and origin sequences.

Insect cell cultures can also be used to produce the humanized immunoglobulins of the invention, typically using cells of S2 *Drosophila* transfected in stable fashion or cells of *Spodoptera frugiperda* with the expression system based on the *Baculovirus* (Putlitz et al., 1990).

Plants and cultures of vegetable cells can be used for the expression of the humanized immunoglobulins of the invention. (Larrick & Fry, 1991; Benvenuto et al., 1991; Durin et al., 1990; Hiatt et al, 1989).

However, in all these cases it is impossible to obtain the correct type of glycosylation necessary to assure the effector function in the activation of the human immune system. For this purpose, it is possible to use tissue cultures of mammal cells to express the polypeptides of the present invention in integral form of IgG1, which have proven to be the most effective isotype among seric immunoglobulins in the induction of the immune response (Winnacker, 1987). It should be stressed that, considering that the isotype determines the lytic potential of an antibody, generally the IgG1 isotype is used for therapeutic purposes (since it induces the immune response, both cell-mediated and mediated by the system of the complement), whilst the IgG4 is used for diagnostic applications (Riechmann et al., 1988). In particular, mammal cell are preferred, considering the great number of host cell lines developed for the secretion of intact immunoglobulins, among them the CHO cell lines, several lines of COS, the HeLa cells, myeloma cell lines (NSO, SP/2, YB/0 e P3X63.Ag8.653), transformed B cells or hybridomas. Expression carriers for these cells can include expression control sequences, such as a replication origin, a promoter, an enhancer (Queen et al., 1986), and the sequences required for ribosome binding, RNA splicing and polyadenylation, and sequences for transcription termination. The expression control sequences of choice are promoters deriving from immunoglobulin genes and from viruses, such as SV40, Adenovirus, Bovine Papilloma Virus, Cytomegalovirus and the like. Generally, the expression vector includes a selectable marker, such as the resistance to neomycin. For the expression of humanized antibodies, it is preferable to cultivate the mammal cell lines with a serum-free medium. For example, the HUDREG-55 cell line can easily be grown in Serum-Free and Protein-Free Hybridoma Medium Cat. No. S-2897 from Sigma (St. Louis, Mo.).

The genes coding the humanized immunoglobulins of the invention can be used to generate non human transgenic animals, which express the humanized immunoglobulins of interest, typically in a retrievable body fluid such as milk or serum. Such transgenes comprise the polynucleotide sequence coding the humanized immunoglobulins operatively bound to a promoter, usually with an enhancer sequence, such as that of the rodent immunoglobulin or the promoter/enhancer of the casein gene (Buhler et al., 1990; Meade et al, 1990). The transgenes can be transferred into the cells or embryos by means of homologous recombination constructs. Among non human animals used: mouse, rat, sheep, bovine and goat (WO91/08216).

Once they are expressed as intact antibodies, their dimers, the individual light and heavy chains, or in other forms the immunoglobulins of the present invention can be purified following standard procedures, such as precipitation with ammonium sulfate, affinity columns, chromatography on column (Scopes, 1982). For pharmaceutical applications, substantially pure immunoglobulins are necessary, with minimum homogeneity between 90 and 95%, but preferably between 98 and 99% or even higher. Once purified, partially or to the desired homogeneity, proteins can be used for therapeutic use (also in extra-body fashion), for diagnostic use (imaging for the diagnostics of tumors or of Alzheimer's Disease) or to develop and perform biochemical assays, immunofluorescent colorings and the like (see, in general, Lefkovits and Pernis, 1979 and 1981).

A pharmaceutical application of the present invention pertains to the use of humanized immunoglobulin MNAC13 in the form of immunotoxin to eliminate TrkA-expressing cells (in the case of pancreas and prostate tumors). The immunotoxins are characterized by two components and are particularly suitable to kill particular cells both in vitro and in vivo. One component of the cytotoxic agent that is generally lethal for a cell is absorbed or if it interacts with the cell surface. The second component provides the means to address the toxic agent to a specific target cell type, such as the cells that express the epitope of the TrkA receptor. The two components are chemically bound to each other by means of any one of the great variety of chemical procedures available. For example, when the cytotoxic agent is a protein and the second component is an intact immunoglobulin the link can be mediated by cross-binding and heterobifunctional agents (SPDP, carbodiimide, glutaraldehyde). Alternatively, the two components can be bound genetically (Chaudhary et al., 1989). The production of various immunotoxins is reported by Thorpe et al. (1982).

A great number of cytotoxic agents are suitable for application as immunotoxins. Cytotoxic agents can include radionuclides such as iodine 131 or other isotopes of iodine, yttrium 90, rhenium 188 and bismuth 212 or other isotopes that emit alpha particles, a great number of chemotherapeutic drugs such as vindesin, methotrexate, adriamycin and cisplatin; and cytotoxic proteins, such as proteins that inhibit and ribosomes (such as the pokeweed antiviral protein, the *Pseudomonas* exotoxin A and the diphteric toxin, ricin A and clavin of vegetable origin) or agents active at the cell surface level (such as phospholipase enzymes such as phospholipase C)—eds. Baldwin and Byers, 1985; U.S. Ser. No. 07/290, 968; Olsnes and Phil, 1982. It should be stressed that the cytoxic region of the immunotoxin can itself be immunogenic and consequently limit the clinical usefulness of the fusion protein in case of chronic or long term therapy. An alternative to avoid the problem of the immunogenicity of the toxin is to express in fusion with the binding domain of the antibody a protein able to interact with the DNA and bind to this fusion protein the expression carrier that contains the toxin expression cassette. The numerous positive charges of protamin, a human protein that binds the DNA, can interact in stable fashion with the negative charges of the DNA, generating a fusion partner for the neutral charge antibody, much more stable and less immunogenic than the toxin itself. After internalization of the antibody-plasmid complex via receptor mediated endocytosis, the expression of the toxin causes the death of the cell. Moreover, selectivity towards the target cell to be eliminated can be further enhanced by inserting inducible or cell-specific promoters into the toxin expression cassette. This approach is aimed at maximizing the selective elimination of tumor cells while minimizing toxicity side effects (Chen et al., 1995).

The component that addresses the immunotoxin to the correct target includes the MNAC13 humanized immunoglobulin of the present invention in the form of intact immunoglobulin or of the binding fragment or as Fab or Fv fragment. Typically, the antibodies in the immunotoxins are of the human isotype IgM or IgG, but other constant regions can be used as well.

The antibodies and the pharmaceutical compositions of this invention are particularly useful for administration, following any effective methodology to address the antibodies at the level of the tissue involved in the pathology. This includes (but is not limited to): intraperitoneal, intramuscular, intravenous, subcutaneous, intratracheal, oral, enteral, parenteral, intranasal or dermal administration. The antibodies of the present invention can typically be administered for local application by injection (intraperitoneal or intracranial—typically in a cerebral ventricle—or intrapericardiac or intrabursal) of liquid formulations or by ingestion of solid formulations (in the form of pills, tablets, capsules) or of liquid formulations (in the form of emulsions and solutions). Compositions for parenteral administration commonly comprise a solution of immunoglobulin dissolved in a compatible, preferably aqueous solution. The concentration of the antibody in these formulations can vary from less than 0.005% to 15-20% and it is selected mainly according to the volumes of the liquid, its viscosity, etc., and according to the particular administration mode selected.

Alternatively, the antibodies can be prepared for administration in solid form. The antibodies can be combined with different inert or excipient substances, which can include ligands such as microcrystalline cellulose, gelatin or Arabic rubber; recipients such lactose or starch; agents such as alginic acid, Primogel or corn starch; lubricants such as magnesium stearate, colloidal silicon dioxide; sweeteners such as saccharose or saccharin; or flavors, such as mint and methyl salicylate. Other pharmaceutical administration systems include hydrogel, hydroxymethylcellulose, liposomes, microcapsules, microemulsions, microspheres, etc. Local injections directly in the tissues affected by illness such as tumors is a preferential method for the administration of the antibodies of the present invention.

The antibodies of the invention can be frozen or lyophilized and reconstituted immediately before use in a suitable buffer. Considering that lyophilization and reconstitution can determine a variable loss in the activity of the antibody (for conventional immunoglobulins, class IgM antibodies tend to have a greater loss of activities than class IgG antibodies), administration levels must be calibrated to compensate for this fact.

Thanks to their high blocking capacity, the compositions containing the antibodies of the present invention can be administered for prophylactic and/or therapeutic treatments to prevent or reduce the inflammatory component associated to pathological situations or chronic pain, in particular chronic visceral pain (associated to physiological disorders, such as dysmenorrhea, dyspepsia, gastrointestinal reflux, pancreatitis, visceralgia or irritable intestine syndrome).

In prophylactic applications, compositions containing antibodies of the present invention are administered to patients who do not yet suffer from a particular pathology to enhance their resistance.

The antibodies of the present invention also provide a method for reducing the volume of prostate or pancreas tumors and for preventing further tumor growth or reduce the rate of growth of the tumor. This effect can be mediated by both the humanized antibodies of the present invention because they are extremely effective in the neutralization of the interaction between NGF and TrkA, necessary to sustain tumor growth and progression in autocrine or paracrine fashion. Moreover the humanized form of MNAC13 interacts with a membrane receptor and hence can also be used for the direct elimination of neoplastic cells because they are able to activate the host's immune response (if administered in the form of IgG1) or to convey a cytotoxic agent localizing it at the level of the cancerous mass (if administered in the form of immunotoxin). Their administration in the tumor site preferably takes place through direct and localized injection into the tissue or near the tumor site. For systemic administration, doses vary from 0.05 mg/kg per day to 500 mg/kg per day, although dosages in the lower region of the range are preferred because they are easier to administer. Dosages can be calibrated for example to guarantee a particular level in the plasma of the antibody (in the range of about 5-30 mg/ml, preferably between 10-15 mg/ml) and maintain this level for a given period of time until the clinical results are achieved. Humanized antibodies should be eliminated much more slowly and require lower dosages to maintain an effective level in the plasma; moreover, considering the high affinity, administration is less frequent and less sizable than with antibodies having lower affinity. The therapeutically effective dosage of each antibody can be determined during the treatment, based on the reduction in the volume of the tumor or on the rate of growth of the tumor or ideally on the total disappearance of the cancerous pathological state. Effective methods for measuring or assessing the stage of pancreatic or prostatic tumors are based on the measurement of the prostate specific antigen (PSA) in blood, on the measurement of the survival time for pancreas tumors, on the measurement of the slowing or inhibition of diffusion for metastases in the case of both tumor.

For direct injection at the level of the tumor site, dosage depends on different factors including the type, stage and volume of the tumor, along with many other variables. Depending on tumor volume, typical therapeutic doses may vary from 0.01 mg/mm and 10 mg/mm injections which can be administered with the necessary frequency. Another method to assess the effectiveness of a particular treatment is to evaluate the inhibition of the TrkA receptor, e.g. by measuring its activity by means of ELISA assay (Angeles et al., 1996).

It is important to stress that, TrkA is configured not only as a therapeutic target but also as a diagnostic target for in vivo imaging, e.g. for imaging of TrkA positive tumors (as a positive or negative marker, depending on tumor type and origin) and imaging on cells of the basal forebrain (as a precocious marker of insurgence of Alzheimer's disease). The MNAC13 humanized antibody of the present invention can also find a wide variety of in vitro applications (ELISA, IRMA, RIA, immunohistochemistry).

For diagnostic purposes, the antibodies can be both marked and unmarked. Unmarked antibodies can be used in combination with other marked antibodies (secondary antibodies), which are reactive against humanized, or human antibodies (e.g. specific antibodies for the constant regions of human immunoglobulins). Alternatively, antibodies can be marked directly. A wide variety of markings can be used, e.g. radionuclides, fluorophores, colorings, enzymes, enzymatic substrates, enzymatic factors, enzymatic inhibitors, ligands (in particular aptenic), etc. Numerous types of immunologic assays are available in the sector.

In particular, for imaging diagnostic applications, to the antibody is conjugated an agent that is detectable or marked in isotopic manner (using radioisotopes of iodine, indium, technetium) or in paramagnetic manner (paramagnetic atoms or ions, such as transition elements, actinides and rare earths; in particular, manganese II, copper II and cobalt II) as described by Goding (1986) and Paik et al. (1982). Imaging procedures entail the intravenous, intraperitoneal or subcutaneous injection (in lymphatic drainage regions to identify lymph node metastases) and they use detectors of radionuclide emissions (such as scintillation .beta. counters) in the case of immunoscintigraphy; if a paramagnetic marking is used instead, an NMR (Nuclear Magnetic Resonance) spectrometer is used. The invention shall now be described in its non limiting embodiments, with reference to the following figures:

RESULTS

X-Ray Structures of the Fab Fragment of the MNAC13 and αD11 Monoclonal Antibodies Both monoclonal antibodies were obtained and purified according to standard procedures. The MNAC13 IgG1 and αD11 IgG2a immunoglobulins were expressed in the supernatant by means of culture of hybridoma cells and concentrated by precipitation with 29% ammonium sulfate followed by dialysis in PBS. Both immunoglobulins were purified by affinity chromatography using a column of Protein G Sepharose (Pharmacia).

Following dialysis in phosphate buffer 10 mM pH 7, EDTA 20 mM using Spectra-Por 12/14K membranes (Spectrum) at 4° C., each sample was concentrated by means of Centricon 50 KDa ultrafiltration units (Amicon) and incubated with 13 mM Cys and treated with immobilized papaine (Pierce) (with an enzyme:substrate ratio of 1:15) for 5 h at 37° C. The procedure for purifying the respective Fab fragments is diversified, although it is always based on ionic exchange chromatography.

In the case of MNAC13, after dialysis against Tris HCl 100 mM pH 8.0, it was possible to eliminate the Fc fragments through a DEAE-Sephacel column (Pharmacia) balanced with the same buffer. FabMNAC13 was collected in the excluded volume whilst the Fc fragments and a fraction of undigested IgG1 were eluted with 250 mM NaCl. The Fab fragment was separated from undigested IgG1 by gel filtration on a Superdex G75 (Pharmacia) column balanced with Tris HCl 100 mM pH 8.0, NaCl 150 mM. The homogeneity and purity of the fractions was controlled by electrophoretic separation on 12% polyacrylamide gel followed by coloring with Coomassie (FIG. 1A). The concentration of the purified protein was determined by means of Lowry assay (Bio-Rad). From 1l of hybridoma surnatant, it was possible to obtain up to 3 mg of MNAC13 Fab (with purity exceeding 99%).

Figure 2A:
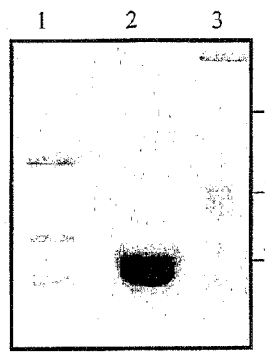
FIG. 2: A) depicts the analysis by means of polyacrylamide in denaturing conditions (SDS-PAGE 12%) and coloring with Coomassie Blue of the result of the purification of the Fab fragment of the αD11 antibody (well 1: sample of αD11 antibody digested proteolytically with papaine; well 2: Fab fragment of the purified and concentrated αD11 antibody; well 3: molecular weights); B) depicts a typical crystal of the Fab fragment of the αD11 antibody C) depicts a high resolution diffraction spectrum obtained with a crystal of the Fab fragment of the αD11 antibody; D) is a Ramachandran chart of the torsion angles of the main chain of the heavy and light domains of the Fab fragment of the αD11 antibody.

In terms of the purification of the Fab fragment of the αD11 antibody, the sample treated with papaine was dialyzed against 10 mM pH 7.8 phosphate buffer: the Fc fragments were eliminated through a DEAE-Sephacel column (Pharmacia) balanced with this same buffer. The Fab fragment of αD11 was collected in the excluded volume, whilst the Fc fragments and a fraction of undigested IgG2a were eluted with 250 mM pH 6.8 phosphate buffer. The Fab fragment was separated from the undigested IgG2a by means of filtration gel on a Superdex G75 column (Pharmacia) balanced with 10 mM pH 7.8 phosphate buffer, NaCl 150 mM. The homogeneity and purity of the fractions was controlled by electrophoretic separation on 12% polyacrylamide gel followed by coloring with Coomassie (FIG. 2A). The concentration of the purified protein was determined by means of Lowry assay (Bio-Rad). From 1l of hybridoma surnatant, it was possible to obtain up to 6 mg of αD11 Fab (with purity exceeding 99%). Both the Fab fragment of the MNAC13 antibody purified in 10 mM Tris pH 8.0, 50 mM NaCl, and the Fab fragment of the αD11 antibody purified in 10 mM Na phosphate pH 7.8 and 50 mM NaCl were concentrated to 5-10 mg/ml by means of Centricon 30 KDa ultrafiltration unit (Amicon). The crystallization experiments were conducted following the hanging-drop method at 16.degree. C. following a factorial combination approach (Jancarik & Kim, 1991) using Crystal Screen I and II (Hampton Research-Laguna Niguel, Calif., USA-) and Screening Kit (Jena BioSciences).

Drops of 2 µl of the concentrated protein sample were added to an equal volume of the solution containing the precipitant agent and balanced by diffusion with a solution in the reservoir (0.7 ml) in 24 well Linbro plates.

In terms of the Fab fragment of the MNAC13 antibody, the most promising initial result, obtained with equal volumes of protein and precipitant containing 2M ammonium sulfate, 5% v/v isopropanol (Crystal Screen II, Reactant #5), was optimized until obtaining crystals that grow in about one week, similar to what is shown in FIG. 1B.

Figure 2B:
Figure 2C:
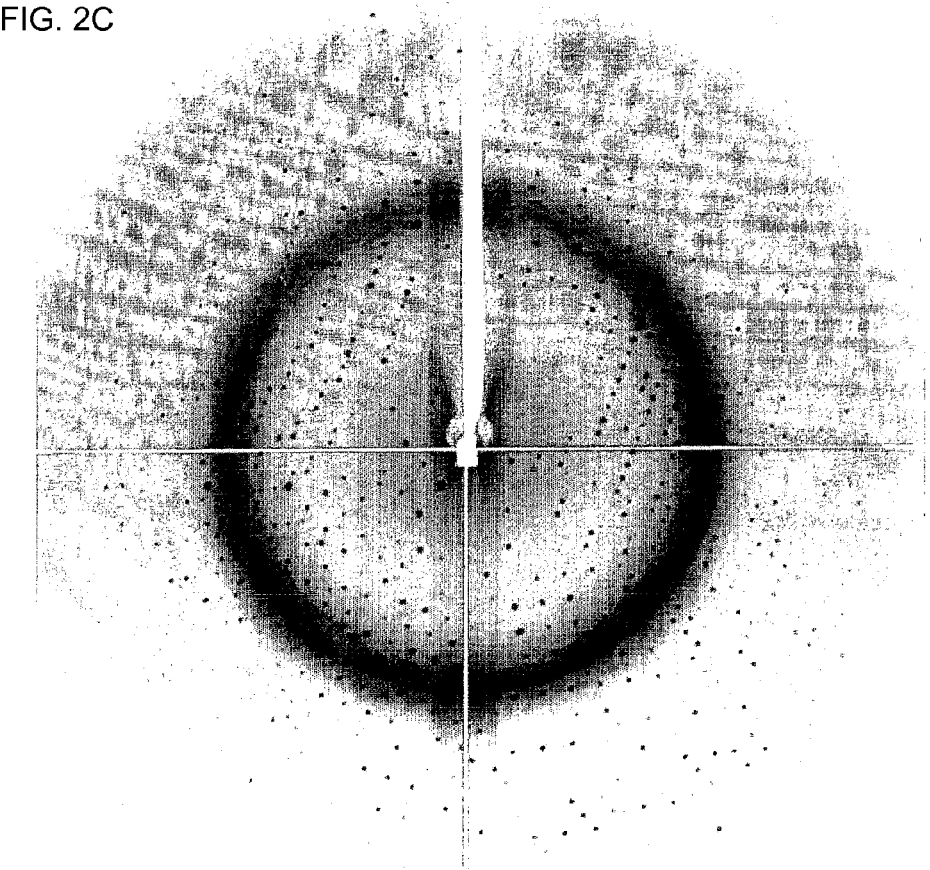

In terms of the Fab fragment of the αD11 antibody, the most promising initial result, obtained using equal volumes of protein and precipitant containing 20% PEG4000, 0.6M NaCl, 100 mM MES pH 6.5 (Kit number 4, solution C2), required a long optimization process, modifying the composition of the precipitant agent to PEG4000, 0.6M NaCl, 100 mM BTP pH 5.5 and the ratios between protein and precipitant solution (1.5:1) until obtaining crystals that grow in about one week, similar to what is shown in FIG. 2B.

In both cases, an initial set of low resolution data was collected on the XRD1 diffraction line of the ELETTRA synchrotron (Trieste, Italy), and then a second, more complete set of data at higher resolution was collected on the ID14-EH1 diffraction line of the ESRF synchrotron (Grenoble, France) The crystals were frozen under liquid nitrogen flow with the cooling system by Oxford Cryosystems (Oxford, UK), using in the case of the Fab fragment of the MNAC13 antibody a solution containing 2.2 M ammonium sulfate, 6% v/v isopropanol and 20% v/v glycerol as cryoprotector. A representative high resolution diffraction spectrum for each protein is shown in FIGS. 1B and 2B. All four sets of X-ray diffraction data were processed, indexed, integrated and subsequently scaled using the DENZO and SCALEPACK programs (Otwinowski & Minor, 1997) respectively, while the CCP4 (Collaborative Computational Project, Number 4, 1994) package was used for data reduction. The statistics for the collection and processing of high and low resolution data of the crystals of the Fab fragment of the MNAC13 antibody are set out in the following table:

| X-ray source | ELETTRA | ESRF |
|---|---|---|
| Wavelength (Å) | 1.000 | 0.934 |
| Detector | mar345 | marCCD |
| Spatial group | P2$_1$2$_1$2$_1$ | P2$_1$2$_1$2$_1$ |
| Parameters of the unitary cell | | |
| a (Å) | 52.78 | 52.73 |
| b (Å) | 67.53 | 67.55 |
| c (Å) | 111.51 | 111.43 |
| Mosaicity (°) | 0.40 | 0.47 |
| Resolution interval (Å) | 12.0-2.50 | 17.0-1.80 |
|  | (2.59-2.50) | (1.83-1.80) |
| No. measures | 98688 | 414115 |
| No. of reflexes observed with I ≥ 0 | 56918 | 227914 |
| No. of unique reflexes with I ≥ 0 | 14203 (1371) | 38392 (1893) |
| Completeness (%) | 99.5 (99.3) | 99.5 (99.6) |
| Redundancy | 4.0 (4.0) | 5.9 (4.9) |
| <Iσ (I)> of the measured data | 9.4 (4.7) | 8.2 (1.1) |
| R$_{sym}$ (%) | 5.7 (15.2) | 6.3 (39.8) |

Similarly, the following table summarizes the statistics for the collection and processing of high and low resolution data of the crystals of the Fab fragment of the αD11 antibody:

| X-ray source | ELETTRA | ESRF |
|---|---|---|
| Wavelength (Å) | 1.000 | 0.934 |
| Detector | marCCD | marCCD |
| Spatial group | P1 | C2 |
| Parameters of the unitary cell | | |
| a (Å) | 42.685 | 114.801 |
| b (Å) | 50.626 | 69.354 |
| c (Å) | 102.697 | 64.104 |
| α (°) | 81.977 | 90 |
| β (°) | 89.116 | 117.02 |
| γ (°) | 85.957 | 90 |
| Mosaicity (°) | 0.44 | 0.40 |
| Resolution interval (Å) | 47.6-2.57 | 17.0-1.70 |
|  | (2.8-2.7) | (1.75-1.70) |
| No. measures | 124456 | 492594 |
| No. of reflexes observed with I ≥ 0 | 74241 | 399184 |
| No. of unique reflexes with I ≥ 0 | 23413 (2162) | 47951 (3198) |
| Completeness (%) | 98.2 (92.4) | 97.2 (78.4) |
| Redundancy | 5.7 (5.2) | 6.7 (7.5) |
| <Iσ (I)> of the measured data | 29.6 (6.7) | 9.5 (2.1) |
| R$_{sym}$ (%) | 11.0 (33.5) | 5.8 (27.8) |

Where the values in parenthesis refer to the shell with the highest resolution. Considering the high number of available structures of Fab fragments, the most convenient method to determine the structure of both proteins was Molecular Substitution. In a research in the Protein Data Bank (Berman et al., 2000) for homologous structures, the selection criteria gave priority to the combination between comparable resolution and highest level of sequence identity. On these bases, respectively, were selected for MNAC13: 1BM3: the structure of the complex between Fab fragment of the Opg2 Fab immunoglobulin and the peptide recognized by it (Kodandapani et al., 1999), resolved at a resolution 2.0 Å and provided with a sequence identity respectively of 70 and 88% for the heavy and light chain.

for αD11: 1CIC: the structure of the complex of idiotype-anti-idiotype Fab fragments FabD1.3-FabE225 (Bentley et al., 1990), resolved at a resolution 2.5 Å and provided with a sequence identity respectively of 82 and 82.65% for the heavy and light chain. The determination of both structures was obtained by the Molecular Substitution method using the AMoRe program (Navaza, 1994), with the respective models using separately the constant domains and variable domains considering the extreme variability of the angle formed by the axis of binary pseudosymmetry between the variable and constant regions. The solution obtained in the determination of the structure, of the Fab fragment of MNAC13 following refined with rigid body is shown in the following table:

| Peak | α | β | γ | x | y | z | C$_f$ | R$_f$ | C$_l$ | C$_p$ |
|---|---|---|---|---|---|---|---|---|---|---|
| V | 106.5 | 20.7 | 143.9 | .1004 | .0757 | .04680 | | | | |
| C | 94.5 | 13.9 | 173.3 | .1684 | .3073 | .7355 | 53.7 | 39.8 | 54.8 | 32.4 |

Similarly, the solution obtained in the determination of the structure of the Fab fragment of αD11 following refinement with rigid body for the spatial group C2 is shown in the following table:

| Peak | α | β | γ | x | y | z | C$_f$ | R$_f$ | C$_l$ | C$_p$ |
|---|---|---|---|---|---|---|---|---|---|---|
| V | 151.0 | 155.4 | 43.0 | .1424 | .0005 | .449 | | | | |
| C | 17.8 | 63.7 | 73.2 | .3625 | .9532 | .1991 | 55.0 | 38.9 | 49.7 | 35.9 |

-continued

| Peak | α | β | γ | x | y | z | $C_f$ | $R_f$ | $C_I$ | $C_p$ |
|------|---|---|---|---|---|---|-------|-------|-------|-------|

Where
V = variable domain
C = constant domain
α, β, γ = Eurelian angles(°).
x, y, z = Translation (fractionary).
$C_f$ = Correlation of the amplitudes (×100)
$R_f$ = Crystallographic R factor.
$C_I$ = Correlation of the intensities (×100).
$C_p$ = Correlation of the truncated Patterson function (×100).

The subsequent refinement of the two structures was obtained by means of a cyclic procedures, comprising two alternated phase: manual construction of the model using the interactive software for computer graphics "O" (Kleywegt and Jones, 1994); positional refinement and refinement of B isotropic thermal factors using automatic protocols of the CNS suite, Crystallography and NMR System (Brunger et al., 1998). The procedure after some phases of refinement with rigid body, contemplated different refinement cycles. Once the insertion of all mutations and deletion is completed to complete the models, the localization of the water molecules and any ions and ligands was conducted. At the end, maintaining the model as close as possible to the ideal values in terms of stereochemical, the positional weight wa and the weight of the thermal factor B r-weight were optimized. The statistics and the final parameters that describe the quality of the model obtained for the Fab fragment of the MNAC13 antibody are summarized in the following table:

| | |
|---|---|
| Number of protein atoms | 3244 |
| Number of solvent atoms | 351 |
| Number of sulfate ions | 4 |
| Number of Tris molecules | 1 |
| Number of isopropanol molecules | 1 |
| Resolution interval (Å) | 39-1.778 |
| Final R factor | 19.35% |
| Final $R_{free}$ factor (calculated on 10% of the data) | 23.22% |
| Rms Deviations | |
| Binding distances (Å) | 0.008 |
| Binding angles (°) | 1.456 |
| Dihedral angles (°) | 27.29 |
| Improper angles (°) | 0.928 |
| Mean Isotrope Thermal Factor (Å$^2$) | |
| Complete protein | 23.55 |
| Light chain | 24.14 |
| Heavy chain | 22.99 |
| Water molecules | 31.95 |
| Ions (sulfate) | 55.94 |
| Tris | 46.06 |
| Isopropanol | 32.60 |

Similarly, the statistics and the final parameters that describe the quality of the model obtained for the Fab fragment of the αD11 antibody are summarized in the following table:

| | |
|---|---|
| Number of protein atoms | 3229 |
| Number of solvent atoms | 403 |
| Number of chloride ions | 1 |
| Resolution interval (Å) | 30-1.70 |
| Final R factor | 19.54% |
| Final $R_{free}$ factor (calculated on 10% of the data) | 24.22% |
| Rms Deviations | |
| Binding distances (Å) | 0.0096 |
| Angoli di legame (°) | 1.6571 |
| Binding Angles (°) | 1.6571 |

-continued

| | |
|---|---|
| Angoli dieDihedral angles (°) | 27.40 |
| Improper angles (°) | 1.048 |
| Mean Isotrope Thermal Factor (Å$^2$) | |
| Complete protein | 25.58 |
| Light chain | 24.14 |
| Heavy chain | 22.99 |
| Water molecules | 38.80 |
| Ions (chloride) | 20.58 |

Figure 2D:
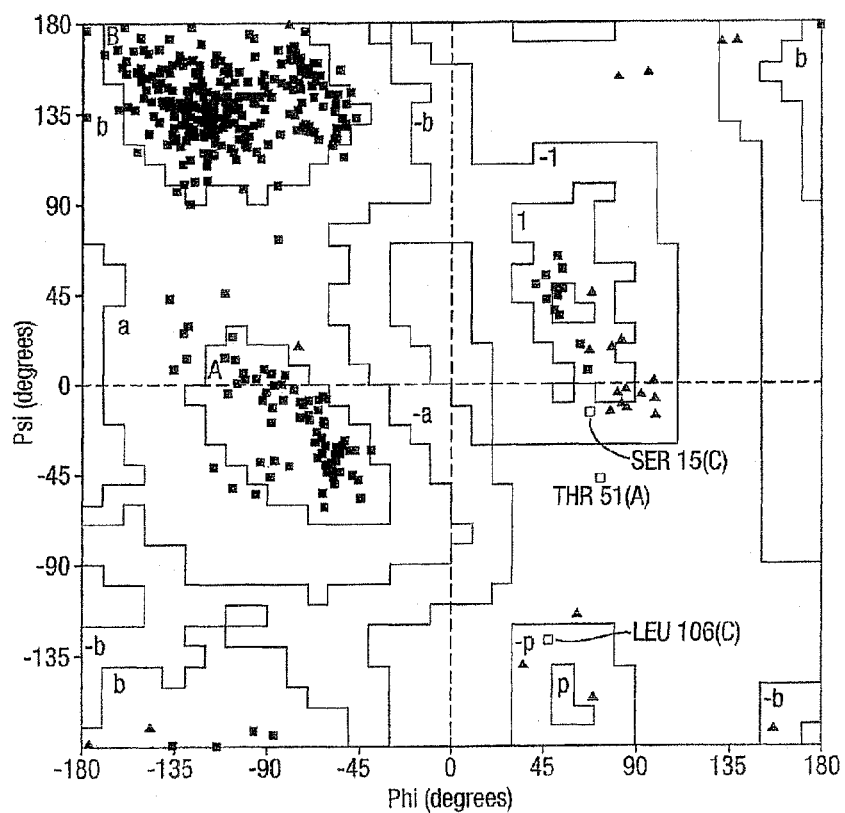

Moreover, both models were examined by final geometry analysis with the PROCHECK suite (Laskowski et al., 1993) as shown in the respective tables and in the respective Ramachandran charts (FIGS. 1D and 2D).

Use of the X-Ray Structures of the Fab Fragment of the MNAC13 and αD11 Monoclonal Antibodies in the Selection of a Framework of Human Origin In the selection of human antibody framework, the approach described above was follows, which combines on the degree of identity between the antibody of murine and human origin at the primary sequence level to the degree of structural similarity of the polypeptide skeletons.

In particular, a series of possible acceptor frameworks of human origin or humanized antibodies was selected on the basis of the highest level both of homology and of identity of the primary structures by a search in the BLAST database. This selection was conducted for both blocking antibodies both considering the entire variable regions of the antibodies and narrowing the search to the framework regions.

Within each group of selected antibodies, only those for which structural data with high resolution or otherwise with resolution comparable to that of the structures obtained by us (i.e. no greater than 2.5 Å are available were considered, conducting a search in PDB (Protein Data Bank). The respective amino acid skeleton were then superimposed using the "superimpose" software (Diederichs, 1995).

Figure 3A:
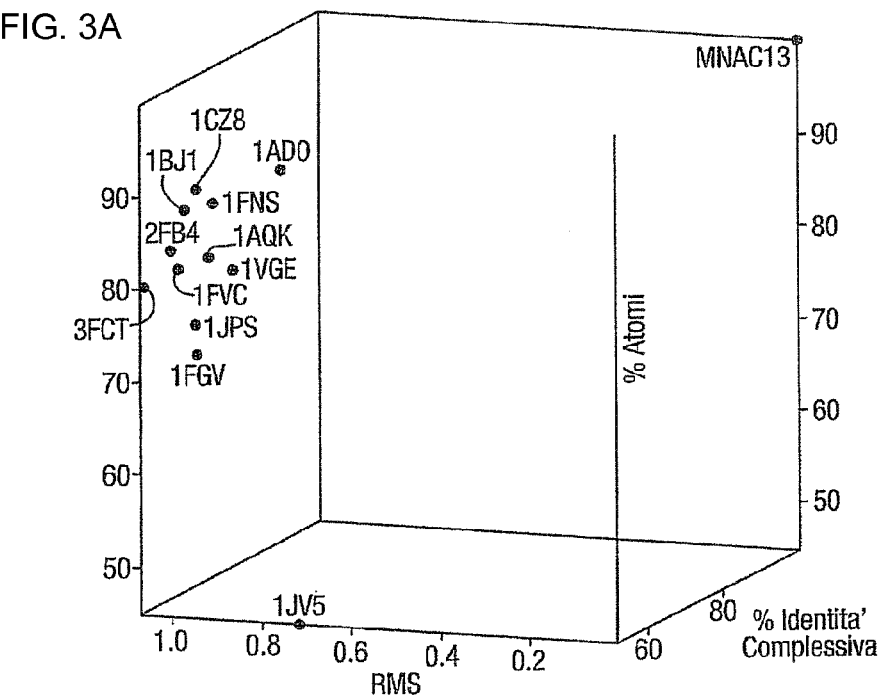
Figure 3B:
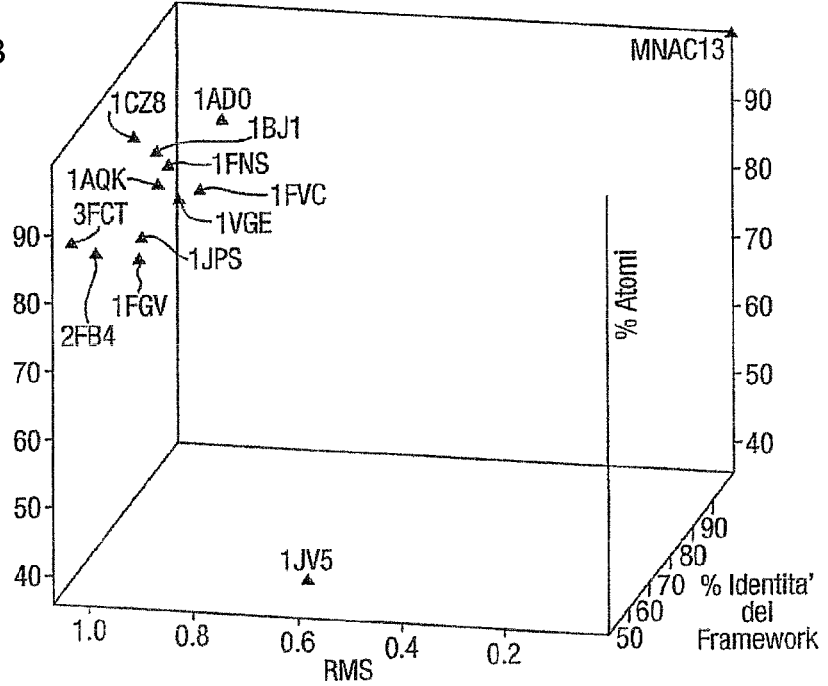
Figure 3C:
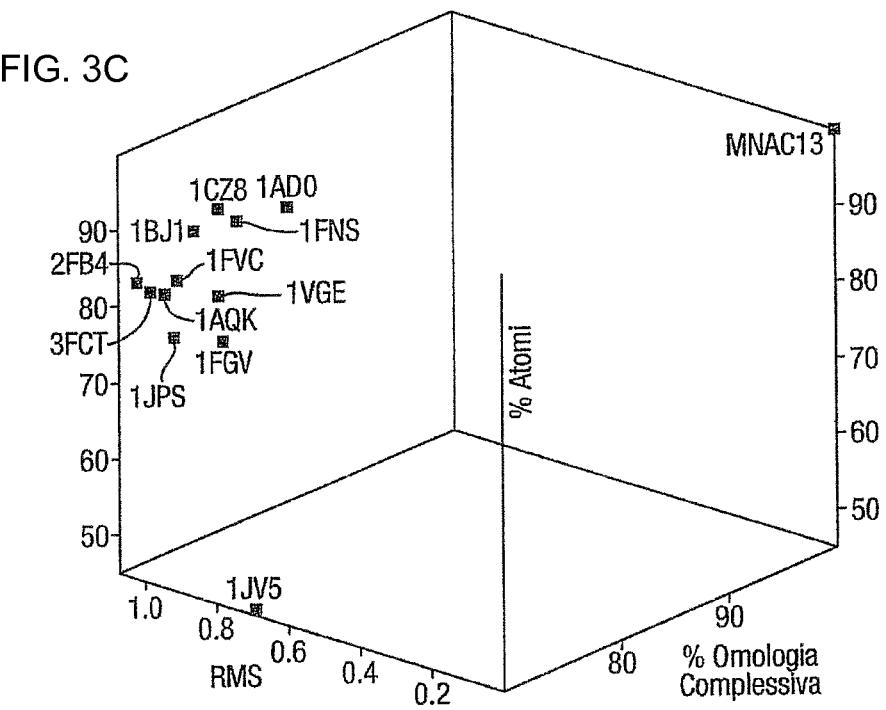
Figure 3D:
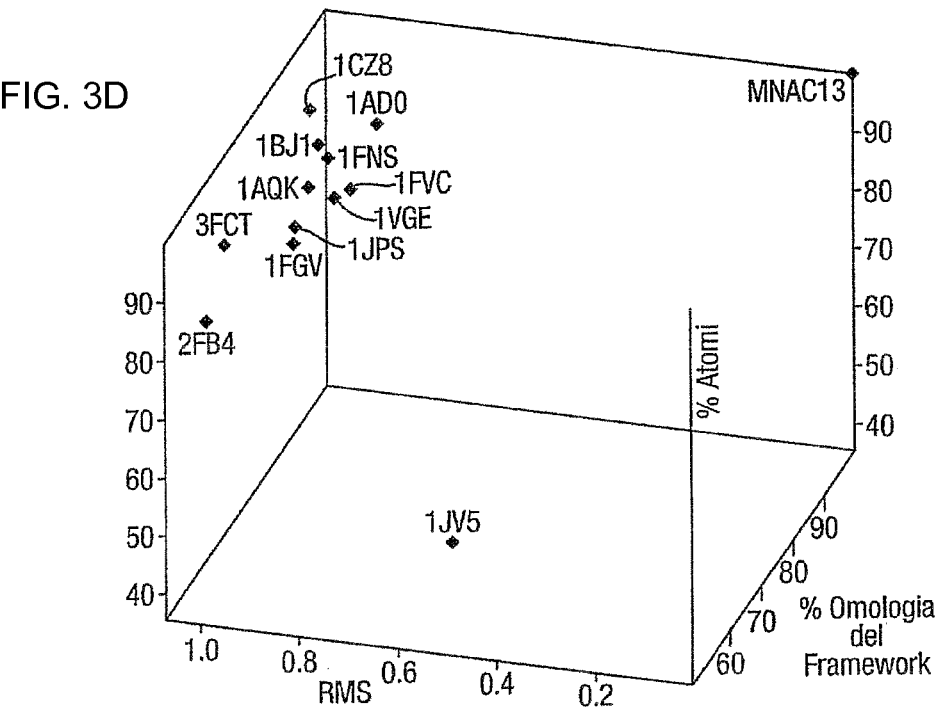
Figure 3E:
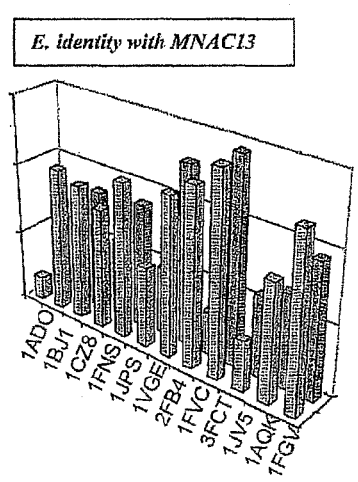
Figure 3F:
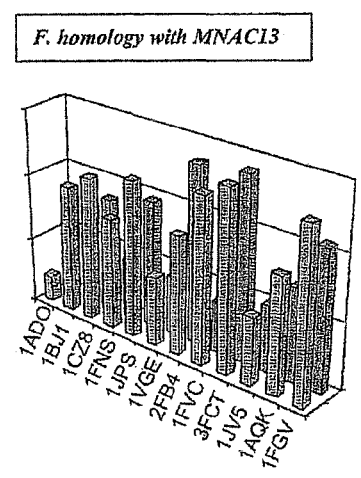
Figure 3G:
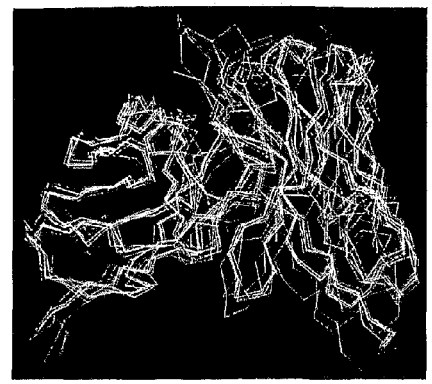
Figure 4A:
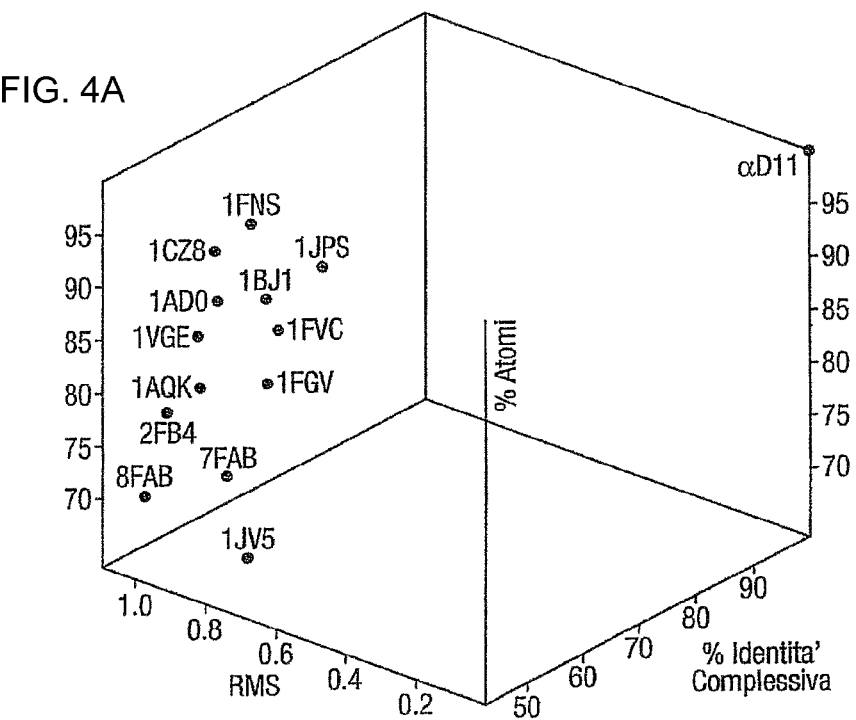
Figure 4B:
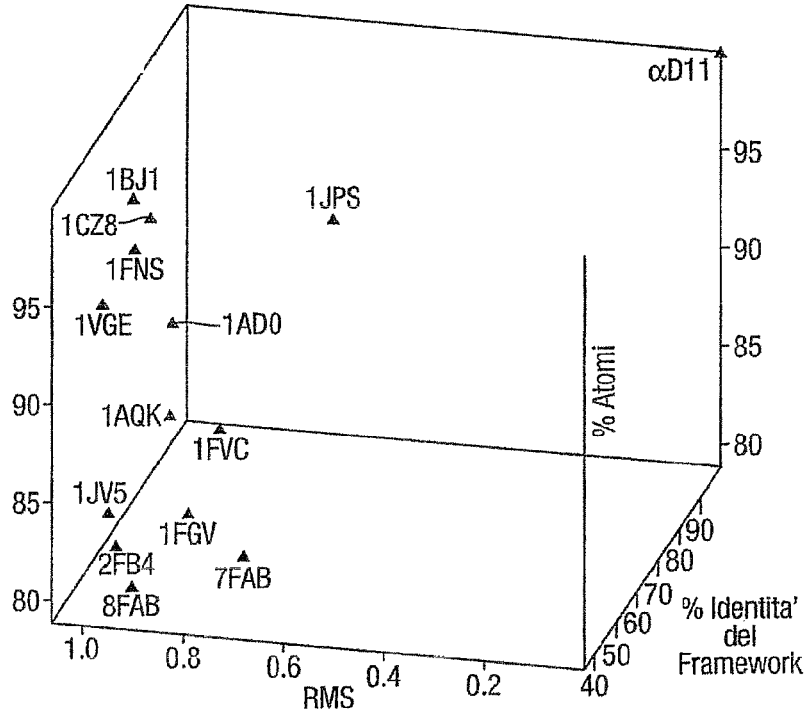
Figure 4C:
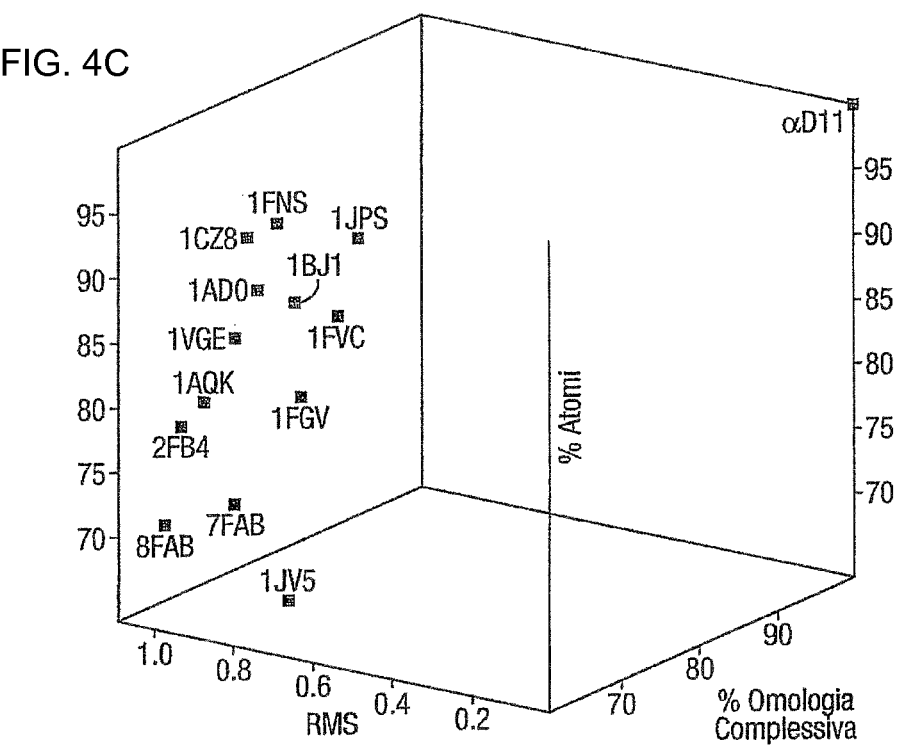
Figure 4D:
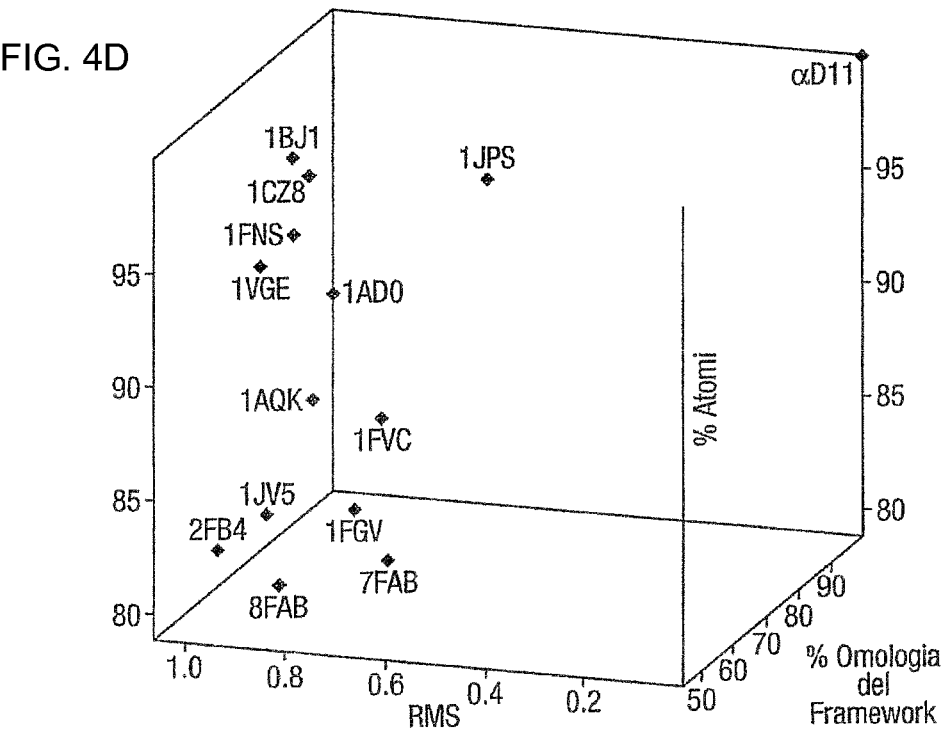
Figure 4E:
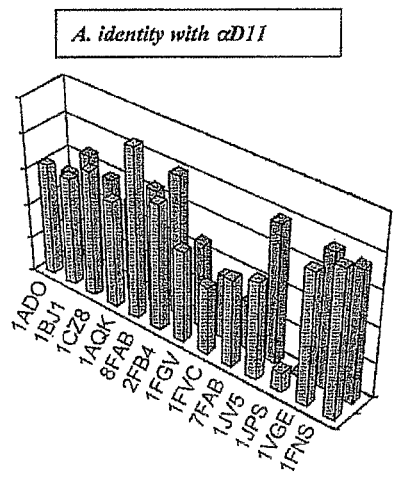
Figure 4F:
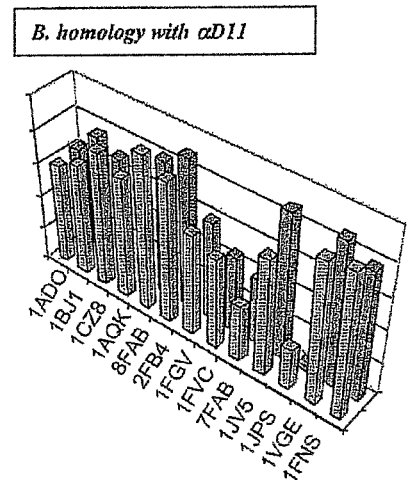
Figure 4G:
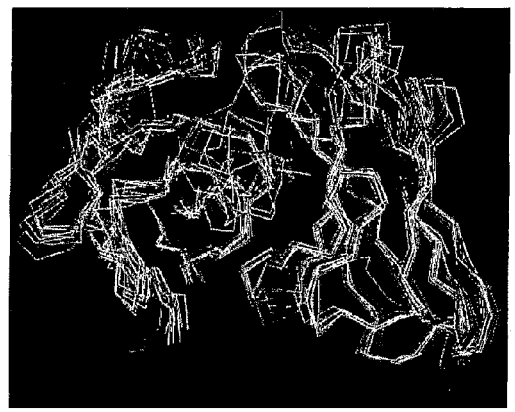

FIGS. 3G and 4G show the result of the alignment between the Fv region (respectively of MNAC13 and αD11) and the tertiary structures of the alpha carbon atom skeletons of the humanized or human origin antibodies, selected on the basis of the optimal alignment of the primary structures with the antibody to be humanized and of the high resolution of the available structural data.

To assess the degree of superposition of each individual structure, of human origin or engineered, both with MNAC13 and with αD11 the RMS was calculated between atoms of alpha carbon constituting the respective amino acid skeletons, not considering atom pairs with an RMS exceeding 2 Å.

The selection of the optimal framework for humanization is configured as a three-variable problem, which can thus be represented in space, both when associating the homology level and the degree of identity to the structural alignment.

This type of analysis was then conducted also reducing the regions in question in the two types of alignment to the regions of the respective frameworks.

As shown in FIGS. 3 and 4, the distributions of the antibodies considered in the space of the three analyzed variables (respectively, value of RMS, percentages of atoms on which RMS was calculated and a similitude index between primary structures, i.e. percentage of overall identity -A-, of overall homology -C-, of identity at the framework level -B-, of homology at the framework level -D-) are mutually coherent and consistent for both cases considered.

Moreover, comparing these distributions with the optimal position in the space of the three variables which each antibody would occupy if it were of human origin, it is possible clearly to identify the human origin antibody that most approximates this ideal position at the primary and tertiary structure level. To rationalize, in the case of both antibodies, this result, in each of the four analyses the deviations from the hypothetical optimal position were calculated for each position of the humanized or human origin antibodies considered (FIGS. 3E and 3F for MNAC13 and FIGS. 4E and 4F for αD11). In this case, too, the results are consistent and confirm the previous indications.

Figures 3H, 3I:
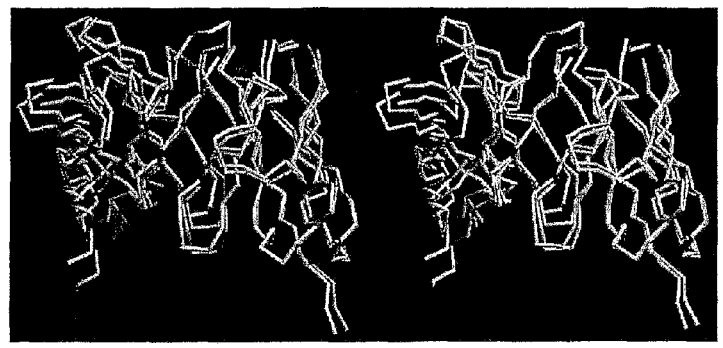
Figure 3J:
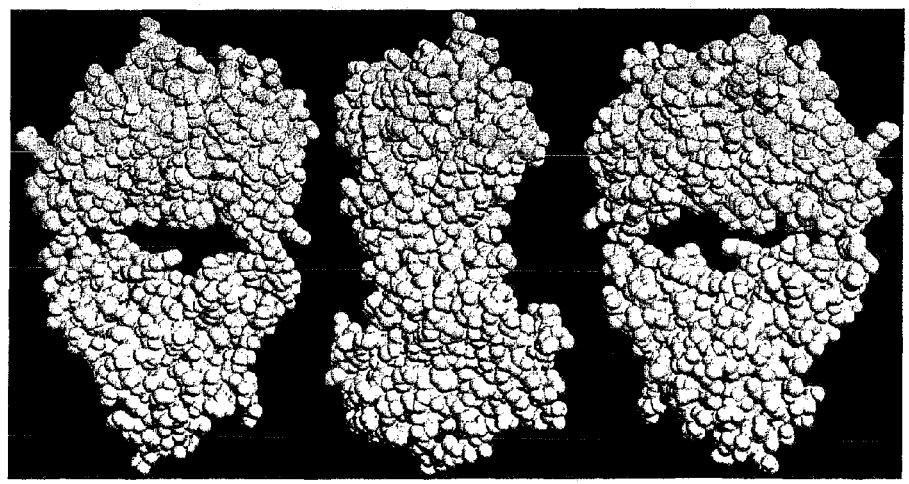
Figure 4H:
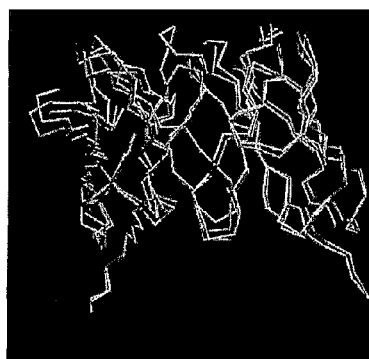
Figure 4I:
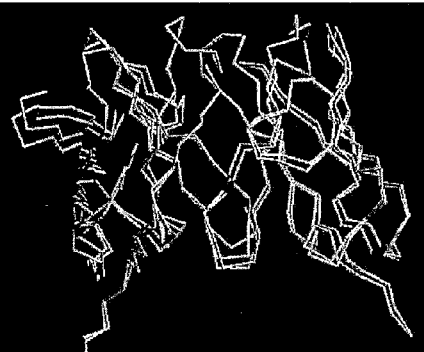
Figure 4J:
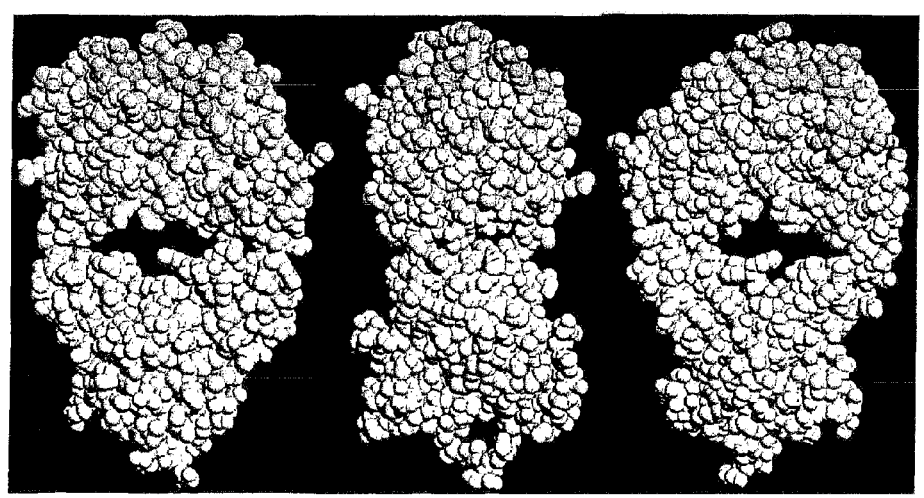

On the basis of this method of selection, two different humanized antibodies were selected as acceptor framework in the subsequent process of CDR grafting for the humanization of the two antibodies neutralizing the NGF/TrkA interaction. In particular, FIGS. 3H and 4H show the structural alignment at the level of the Fv region of the two blocking antibodies with the respective selected humanized antibody, i.e. using the PDB, 1JPS codes for αD11 and 1AD0 codes for MNAC13. FIGS. 3I and 4I compare the same region of the murine antibody with the model of the same antibody following CDR grafting.

Once the CDRs are defined, the canonical classes (defined by Chothia and Lesk) to which they belong were identified and subsequently the canonical residues in the humanized antibody were maintained: for each antibody, they were highlighted with underlined character in FIG. 5 and FIG. 6.

In regard to the subsequent analysis of the retro-mutations to be introduced, to maintain the residues that mediate the interaction between the light chain and the heavy chain of the variable domains, the following retro-mutations were inserted to maintain the interface between the two domains:
L46 and H35, H37 for MNAC13
L34, L46, L92 and H35 for αD11.

Moreover, to maintain the characteristics of the Vernier zone, the following retro-mutations were made:
L98 for MNAC13
H71 for αD11 (which in any case regard substitutions for amino acid residues represented in human consensus sequences).

Subsequently, following the comparison with the main consensus sequences of human immunoglobulins, the following retro-mutations were made:
L1, L2, L13, L50, L73, L104 and H24, H48, H49, H73, H76, H82B, H87, H90, H93 for MNAC13
L56 for αD11

Moreover, again on the basis of the consensus sequences of human immunoglobulins, in the humanized form of MNAC13 the following mutations were introduced which insert residues preserved in the human instead of the unusual residues present both in the donor and in the acceptor framework.
L42 (L→Q), L83 (I→V) and H83 (Q→R), H89 (I→V).

For the same reason, the following mutation was introduced in the humanized form of αD11. H67 (V→F).

The respective pairs of crystallographic structures were modified, first effecting the grafting of the CDRs of animal origin in the humanized frameworks. Then, all the mutations and retro-mutations described above were introduced. The modified structures were then assembled in composite immunoglobulins. The resulting models were refined by minimizing mechanical energy (in terms of torsion angles and binding angles and distances) using the force field.

Humanization of the MNAC13 and αD11 Monoclonal Antibodies

Figure 9A:
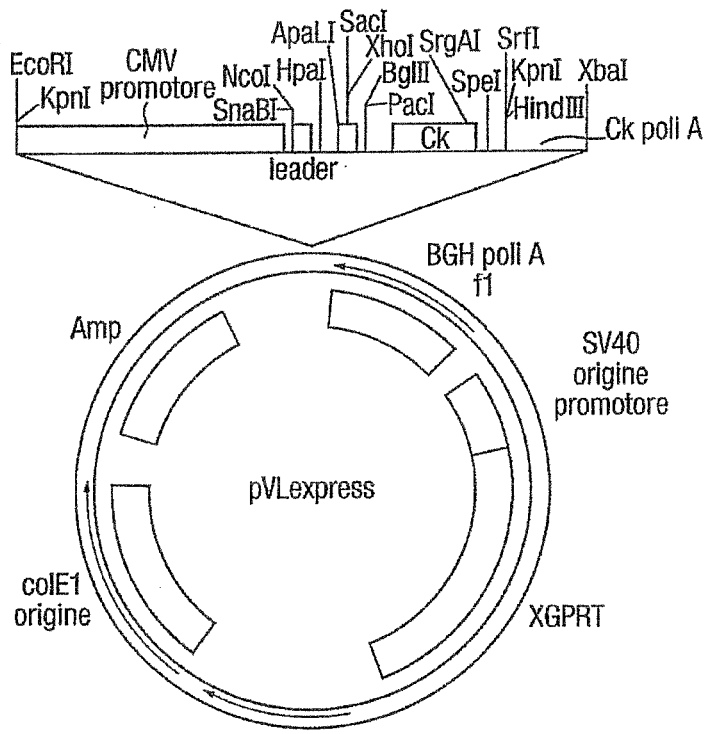
Figure 9B:
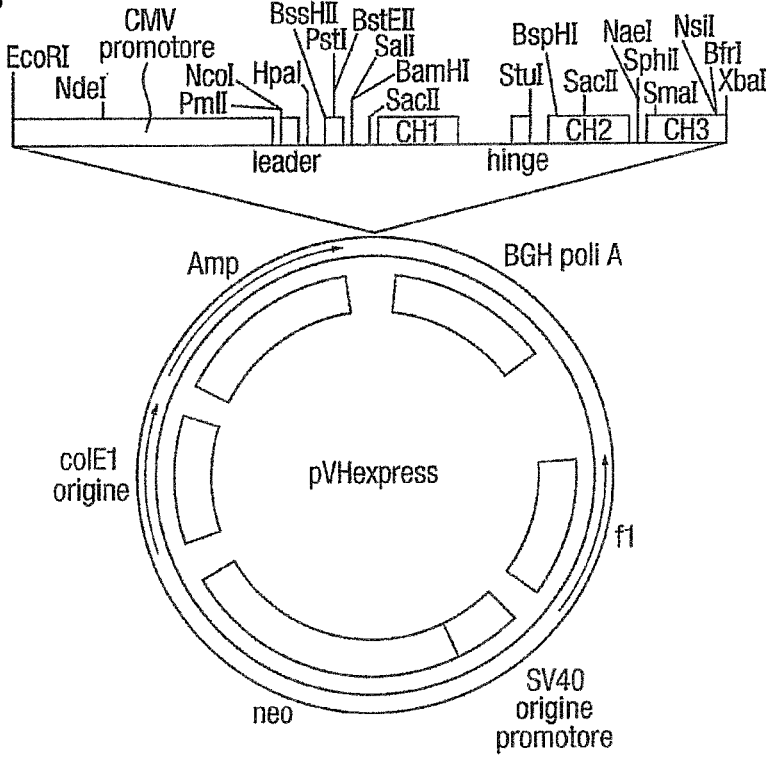
Figure 9C:
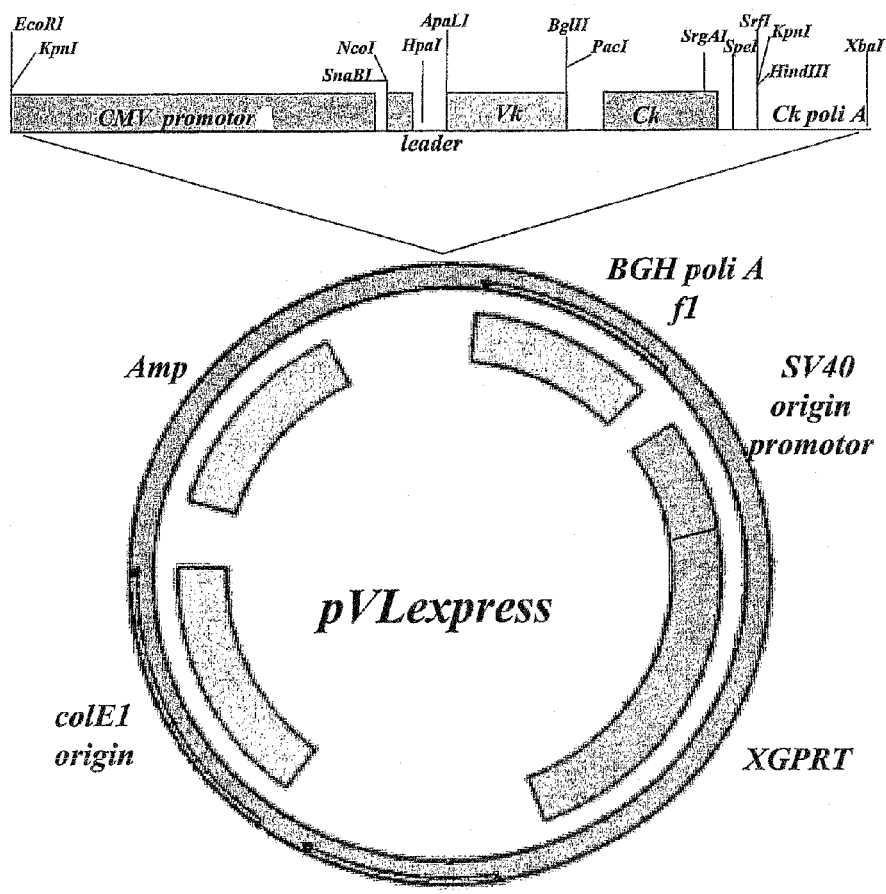

After selecting the donor humanized antibody of the framework to achieve the CDR grafting of MNAC13, the respectively variable regions are designed which combine the murine CDRs of MNAC13 with the framework of the humanized antibody modified according to the mutations set out above. A similar procedure was followed for αD11. Substantially, the two humanized variable regions can be obtained by a procedure based on the overlap assembly PCR method, using oligonucleotides of about 80 bases, which alternate the sense and anti-sense filament with consecutive superposed for a length of 20 bases in such a way as to allow the formation of partially dual filament molecules as a result of hybridation (FIGS. 7B and 8B). After filling discontinuities by means of Vent polymerase, the dual filament is amplified for PCR using as primers two short oligonucleotides bearing the sequences at the 5' of the dual filament itself together with restriction sites suitable for the subsequent directional cloning (respectively ApaLI/BglIII for the cloning of the variable domain of the light chain and BssHII/BstEII for the cloning of the variable domain of the heavy chain), after digestion with respective restriction enzymes, in the pVLexpress plasmid for the variable domain of the light chain (FIG. 9A) and in the pVHexpress plasmid for the variable domain of the heavy chain (FIG. 9B). These carriers allow to express in fusion with the cloned sequences the constant domains of human origin respectively Cκ and CH1, CH2 and CH3. Using these vectors, it is therefore possible to express both antibodies in the form of IgG1 molecules (FIGS. 9C and 9D1) in human cell lines like those listed above. To obtain both humanized antibodies in the form of Fab fragments, it is sufficient to act solely on the carrier in which the heavy chain is cloned. In particular, it is possible to substitute the entire constant part with the sole CH1 domain amplified for PCR using specific primers provided with restriction sites at the extremes for the SacII-XbaI directional cloning (as shown in FIG. 9D2).

Figure 9D:
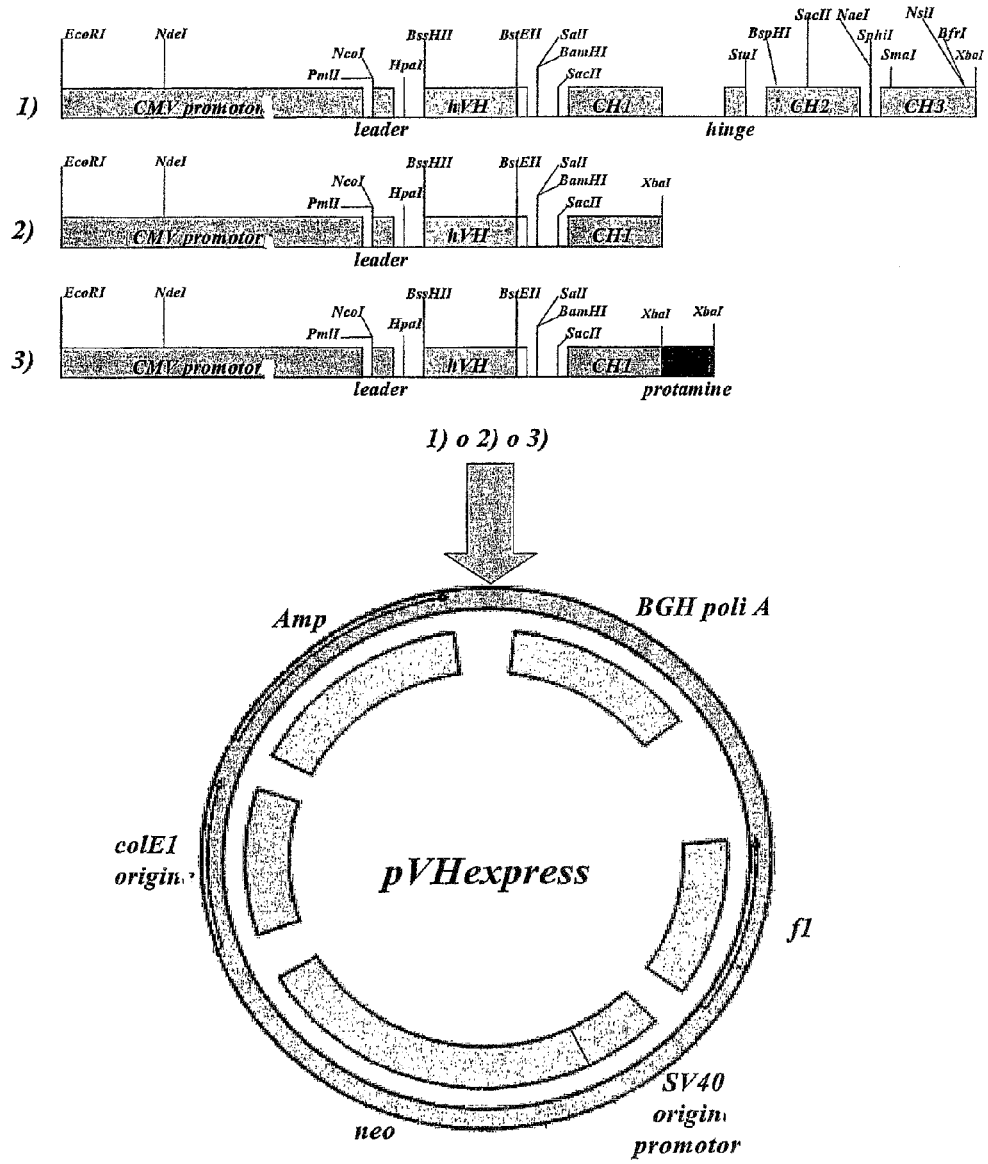

Lastly, to obtain the MNAC13 humanized antibody in the form of immunotoxin, it is possible to express at the carboxy-terminal of the constant domain CH1 the basic protamin protein amplified for PCR using specific primers provided with the restriction site at the extreme for non direction XbaI cloning (as shown in FIG. 9D3).

Expression and Binding Assay of the MNAC and αD11 Humanized Antibodies 250 thousand COS cells were co-transfected with 1.mu.g of coding plasmidic DNA for VH at VK of each humanized antibody (a total of 2 μg) by means of FuGENE according to recommended protocol (Roche). The constructs were used to obtain the humanized antibodies in the form of IgG1.

In parallel to the co-transfections of the constructs described above, the corresponding chimeric forms were co-transfected for each antibody, i.e.:
the murine VH of MNAC13 cloned in CMV pVH express and the murine Vk of MNAC13 cloned in CMV pVk express;in regard to αD11 the rat VH is cloned in fusion with the C.gamma. of human origin in pcDNA1 and the rat Vk is cloned in fusion with the C.gamma. of human origin pcDNA1.

After 72 hours from the transfection, the supernatant containing the immunoglobulins expressed by the host cells was collected, and concentrated using Centriprep 50 (Amicon).

The ability to recognize the respective ligands of the two humanized antibodies was verified by means of ELISA assay and compared with respective chimeric forms. The results are shown in FIGS. 10 and 11.

For immobilization on plastic, 96 well Maxi sorb plates were incubated at 4° C. overnight with a solution containing the respective ligands of the two antibodies (the purified recombinant immunoadhesin TrkA Camel and the murine NGF purified from submandibular glands) at a concentration of 10 µg/ml in 0.1M pH 9.6 sodium carbonate buffer.

After one hour of blocking with PBS containing 3% milk (MPBS) at ambient temperature, concentrated supernatants were incubated with serial dilutions (1:2, 1.20; 1:200) and in parallel also with the supernatant of non transfected COS cells (negative control).

After incubation with the primary antibody (which recognizes the constant C.gamma. region of human origin) and with the secondary antibody (anti-rabbit conjugated with peroxidase), it is possible to detect the binding activity as optical density at 450 nm (OD450) by means of incubation with the TMB substrate (TECNA). The respective monoclonal antibodies at a concentration of 500 ng/ml were included as positive controls.

Figure 10B:
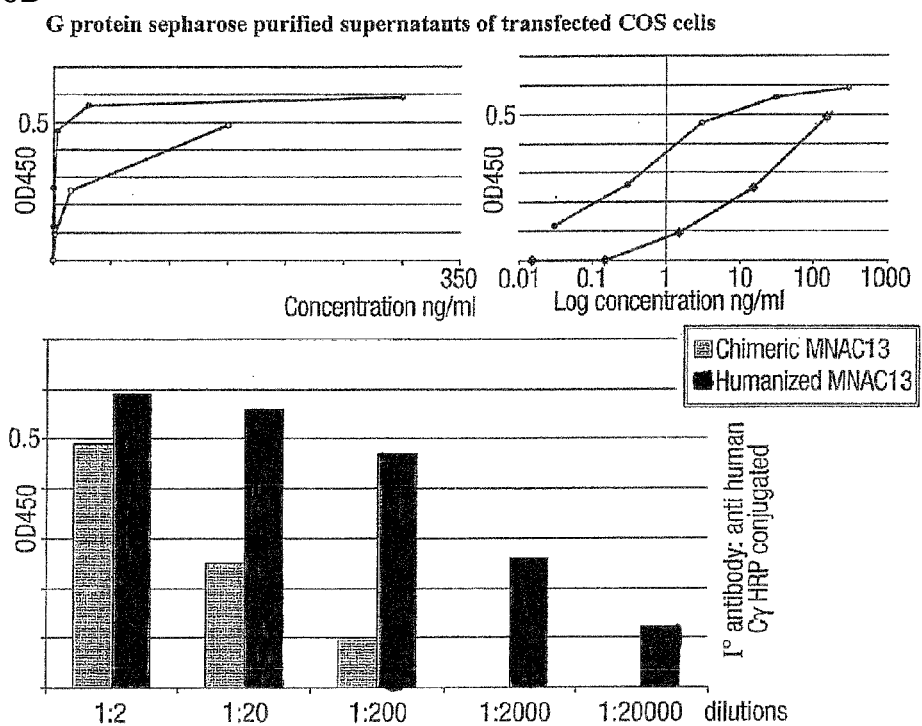

FIG. 10B shows the results of a similar ELISA assay conducted after purification by means of affinity chromatography of the expressed immunoglobulins.

In detail, the supernatants of the transfected cells were collected and, after removing cellular detritus by centrifuging, they were incubated with 100.mu.l of Protein G Sepharose and after extensive washings with PBS each protein was eluted with 1 mM HCl and the pH was neutralized immediately after elution with 1 M Tris pH 8.8. The respective concentrations were estimated with Lowry assay.

BIBLIOGRAPHY

Adair et al. Hum. Antibod. Hybridomas 5:41 (1994)
Angeles et al. Anal Biochem; 236, 49 (1996)
Baca et al. J. Biol. Chem. 272:10678 (1997)
Baker et al. "Antigen and Antibody Molecular Engineering": 61 (1994)
Barinaga, Science; 264, 272 (1994)
Benhar et al. P.N.A.S. 91:12051 (1994)
Bentley et al. Nature; 348, 254 (1990)
Benvenuto et al. Plant Mol. Biol; 17 865 (1991)
Berardi et al. PNAS; 91, 684 (1994)
Berman et al. Nucleic Acids Res.; 28, 235 (2000).
Bird et al. Science; 242, 423 (1988)
Bold et al. J. Neurochem.; 64, 2622 (1995)
Buhler et al. Bio/Technology; 8, 140 (1990)
Buchner and Rudolph, Bio/Technology; 9, 157 (1991)
Brunger, Acta Cryst.; D54, 905 (1998)
Carter et al. P.N.A.S. 89:4285 (1992)
Carugo and Pongor Protein Science 10, 1470 (2001)
Carugo, J. Appl. Cryst.; 36, 125 (2003)
Cattaneo et al. J. Neurosci.; 19, 9687 (1999)
Cesareni, FEBS Lett; 307, 66 (1992)
Clackson et al. Nature; 352, 624 (1991)
Chaudhary et al., Nature; 339, 394 (1989)
Chen et al., Gene Ther; 2, 116 (1995)
Chothia & Lesk, J. Mol. Biol.; 196, 901 (1987)
Chothia et al. Nature; 342, 878 (1989).
Co et al. PNAS; 88, 2869 (1991)
Co et al. J. Immunol. 148:1149-1154 (1992)
Cook et al. Prot. Engng. 9:623-628 (1996)
Couto et al. "Antigen and Antibody Molecular Engineering" 55 (1994)
Daugherty et al. Nucleic Acid Res. 19:2471 (1991)
De Martino et al. Antibod. Immunoconj. Radiopharmaceut. 4:829 (1991).
Delsite et al. J. Androl.; 17, 481 (1996)
De Schryver-Kecskemeti et al. Arch. Pathol.; 111, 833 (1987)
Diederichs, Proteins: 23 187 (1995)
Djakiew et al. Cancer Res.; 51, 3304 (1991)
Domenici et al. Vis Neurosci.; 11, 1093 (1994)
Durin et al. Plant Mol. Biol.; 15, 281 (1990)
Eigenbrot et al. Proteins 18: 49 (1994)
Ellis et al. J. Immunol. 155:925 (1995)
Foote & Winter J. Mol. Biol. 224:487 (1992)
Garrard et al. Bio/Techniques; 9, 1373 (1991)
Gillman & Smith, Gene; 8, 81 (1979)
Goretzki et al. Surgery; 102, 1035 (1987)
Gorman et al. PNAS; 88, 4181 (1991)
Graziano et al. J. Immunol. 155:4996 (1995)
Gram et al. PNAS; 89, 3576 (1992)
Geldof et al. J. Cancer Res. Clin. Oncol.; 123, 107 (1997)
George et al. The Prostrate; 36, 172 (1998)
Goding, Monoclonal antibodies: Principle and practise, 2nd edition, Academic Press (1986)
Gussow & Seemann Meth. Enzymol. 203:99 (1991)
Hakimi et al. J. Immunol. 151:1075 (1993)
Hamilton et al. J. Infect. Diseases 176:59 (1997)
Harlow and Lane, Antibodies. A Laboratory Manual, Cold Spring Harbor Laboratory (1988)
Hiatt et al. Nature; 342, 76 (1989)
Hood et al. Immunology, Benjamin, N.Y., 2nj ed. (1984)
Hsiao et al. Prot. Engng. 7:815 (1994)
Hunkapiller and Hood, Nature; 323, 15 (1986)
Huston et al. PNAS; 85, 5879 (1988)
Jancarik & Kim, Appl. Cryst.; 24, 409 (1991)
Jones et al. Nature; 321, 522 (1986)
Kashmiri et al. Hybridoma 14:461 (1995)
Kettleborough, Protein Engineering; 4, 773 (1991)
Kabat, Sequences of Proteins of Immunological Interest (National Institutes of Health, Bethesda Md., 1987 e 1991) [0196]Kleywegt & Jones, Structure; 2, 1241 (1994).
Kolbinger et al. Prot. Engng. 6:971-980 (1993)
Kodandapani et al. Biochem. Biophys., Res. Comm.; 251, 61 (1998)
Koizumi et al. Pathol. Int.; 48, 93 (1998)
Lachyankar et al. Cancer Res; 57, 532 (1997)
Lanzavecchia et al. Eur. J. Immunol.; 17, 105 (1987)
Larrick & Fry, Hum. Antibodies Hybridomas; 2, 172 (1991)
Laskowski et al. J. Appl. Cryst.; 26, 283 (1993)
Lefkovits e Pernis, Immunological Methods, Vols. I and II (Academic Press, NY, 1979 and 1981).
Leger et al. Hum. Antibod. 8:3-16 (1997)
Lewin & Mendell, Trends Neurosci; 16, 353 (1993)
Lewis & Crowe Gene 101:297 (1991)
Lindsay, Ciba Foundation Symposium; 196, 39, (1996)
MacGrogan et al., J. Neurochem.; 59, 1381 (1992)
Maeda et al. Hum. Antibod. Hybridomas 2:124 (1991)
Maffei et al. J Neurosci; 12, 4651 (1992)
Marchetti et al. Cancer Res.; 56, 2856 (1996)
Matsushima & Bogenmann, Mol Cell Biol.; 13, 7447 (1993)
Meade et al. Bio/Technology; 8, 443 (1990)
McGregor et al. PNAS; 96, 4540 (1999)
Miknyoczki et al. Int. J. Cancer; 81, 417 (1999)
Miknyoczki et al. Crit. Rev. Oncogenesis; 7, 89 (1996).
Miralles et al. J. Endocrinology; 156, 431 (1998)

Molnar et al. Eur J Neurosci; 10, 3127 (1998)
Molnar et al. Neuroreport; 8, 575 (1997)
Monoclonal Antibodies for Cancer Detection and Therapy (eds. Baldwin and Byers, Academic Press, 1985), 159, 224
Muragaki et al. J Neurosci; 17, 530 (1997)
Nakagawara et al. N Engl J Med.; 328, 847 (1993)
Navaza Acta Cryst.; A50, 157 (1994).
Oelmann et al. Cancer Res.; 55, 2212 (1995)
Ohta et al. J. Pathol.; 181, 405 (1997)
Oikawa, et al. Int. J. Pancreat.; 18, 15, (1995)
Olsnes and Phil, Pharmac. There; 25, 355 (1982)
Otwinowski & Minor, Methods Enzymol.; 276, 307 (1997)
Paik et al. J. Nucl. Med.; 23, 37 (1982)
Passaniti et al. Int. J. Cancer; 51, 318 (1992)
Paul, Fundamental Immunology, 3rd ed. Raven Press, N.Y., (1993)
Pflug et al. Mol. Carcin.; 12, 106 (1998)
Pflug et al. Endocrinology; 136, 262 (1995)
Pflug et al. Cancer Res.; 52, 5403 (1992)
Poul et al. Mol. Immunol. 32:101 (1995)
Presta et al. J. Immunol. 151:2623 (1993)
Putlitz et al. Bio/Technology; 8, 651 (1990)
Queen et al. P.N.A.S. 86:10029 (1989)
Remington's Pharmaceutical Science (15th ed., Mack Publishing Company, Easton, Pa., 1980)
Revoltella & Butler, J. Cell. Physiol.; 104, 27 (1980)
Riechmann et al., Nature; 332, 323 (1988)
Roberts et al., Nature; 328, 731 (1987)
Roguska et al. Prot. Engng. 9:895 (1996)
Roguska et al. Prot. Engng. 9:895 (1996)
Roguska et al. PNAS, 91:969 (1994)
Rosok et al. J. Biol. Chem. 271:22611 (1996)
Routledge et al. Eur. J. Immunol. 21:2717 (1991)
Ruberti et al. J Neurosci.; 20, 2589 (2000)
Ruggeri et al. Current Medicinal Chemistry; 6, 845 (1999)
Sato et al. Canc. Res. 53:851 (1993)
Sato et al. Mol. Immunol. 31:371 (1994)
Sato et al. Hum. Antibod. Hybridomas 7:175 (1996)
Scopes, Protein Purification (Springer-Verlag, N.Y., 1982).
Scott & Smith, Science; 249, 386 (1990)
Sha and Xiang Canc. Biother. 9:341 (1994)
Shearman et al. J. Immunol.; 147, 4366 (1991)
Skerra et al. Bio/Technology; 9, 273 (1991)
Sijmons et al. Bio/Technology; 8, 217 (1990)
Sims et al. J. Immunol. 151:2296 (1993)
Singer et al. J. Immunol. 150:2844 (1993)
Swimmer et al. PNAS; 89, 3756 (1992)
Tagliabue et al. J. Biol. Chem.; 275, 5388 (2000)
Tempest et al. Prot. Engng. 7:1501 (1994)
Tempest et al. Int. J. Biol. Macromol. 17:37 (1995)
Tempest et al. Biotechnology; 9, 266 (1991)
Thorpe et al. Monoclonal Antibodies in Clinical Medicine, Academic Press, 168 (1982) U.S. Ser. No. 07/290,968
Verhoeyen et al. Science 239:1534 (1988)
Verhoeyen et al. "Monoclonal Antibodies": 37 (1991)
Verhoeyen et al. Immunol. 78:364 (1993)
Winnacker, From Genes to Clones (VCH Publishers, NY, 1987)
Winter and Milstein, Nature; 349, 293 (1991)
Woolf et al., Neuroscience; 62, 327 (1994).
WO91/08216, 1991
Zhu et al., J. Clin. Oncol., 17, 2419 (1999)
Zhu and Carter J. Immunol. 155:1903 (1995)

The invention claimed is:

1. A polynucleotide encoding:
   (1) a humanized anti-NGF antibody that comprises:
      (a) a VH region having the amino acid sequence set forth in SEQ ID NO:17 and
      (b) a VL region having the amino acid sequence set forth in SEQ ID NO:18, or
   (2) a fragment of the humanized anti-NGF antibody wherein said fragment binds NGF.

2. The polynucleotide of claim 1, wherein the isotype of the humanized anti-NGF antibody encoded by the polynucleotide is IgG, IgM, IgA, IgD or IgE.

3. The polynucleotide of 2, wherein the isotype of the humanized anti-NGF antibody encoded by the polynucleotide is IgG.

4. The polynucleotide of claim 1, wherein the fragment of the humanized anti-NGF antibody encoded by the polynucleotide an Fab fragment, an (Fab')$_2$, an Fv fragment or an single chain Fv fragment (scFv).

5. The polynucleotide of claim 1, wherein said antibody binds murine NGF.

6. An isolated cell comprising the polynucleotide of claim 1.

* * * * *

UNITED STATES PATENT AND TRADEMARK OFFICE
CERTIFICATE OF CORRECTION

PATENT NO. : 8,877,491 B2
APPLICATION NO. : 12/838062
DATED : November 4, 2014
INVENTOR(S) : Cattaneo et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 92 days.

Signed and Sealed this
Sixth Day of June, 2017

Michelle K. Lee
*Director of the United States Patent and Trademark Office*

SEQUENCE LISTING

<160> NUMBER OF SEQ ID NOS: 40

<210> SEQ ID NO 1
<211> LENGTH: 369
<212> TYPE: DNA
<213> ORGANISM: Mus musculus

<400> SEQUENCE: 1

```
caggtgcagc tggtggaatc aggacctggt ctggtgcagc cctcacagac cctgtccctc    60
acctgcactg tctctgggtt ctcactaacc aacaacaatg tgaactgggt tgacaggct    120 acaggaagag gtctggagtg gagtggagga gtctgggctg gtggagccac agattacaat    180
tcagctctca aatcccgact gctgaccatc actagggaca cctccaagag ccaagttttc    240
ttaaaaatgc acatgctgca atctgaagac acagccactt actactgtgc cagagacggg    300
ggctatagca gctctaccct ctatgctatg gatgcctggg gtcaaggaac ttcggtcacc    360
gtctcctca                                                           369
```

<210> SEQ ID NO 2
<211> LENGTH: 122
<212> TYPE: PRT
<213> ORGANISM: Mus musculus

<400> SEQUENCE: 2

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30
```

```
Asn Val Asn Trp Val Arg Gln Ala Thr Gly Arg Gly Leu Glu Trp Met
            35                  40                  45

Gly Gly Val Trp Ala Gly Ala Thr Asp Tyr Asn Ser Ala Leu Lys
 50                  55                  60

Ser Arg Leu Thr Ile Thr Arg Asp Thr Ser Lys Ser Gln Val Phe Leu
 65                  70                  75                  80

Lys Met His Ser Leu Gln Ser Glu Asp Thr Ala Thr Tyr Tyr Cys Ala
                85                  90                  95

Arg Asp Gly Gly Tyr Ser Ser Thr Leu Tyr Ala Met Asp Ala Trp
                100                 105                 110

Gly Gln Gly Thr Thr Val Thr Val Ser Ala
            115                 120
```

<210> SEQ ID NO 3
<211> LENGTH: 321
<212> TYPE: DNA
<213> ORGANISM: Rattus sp.

<400> SEQUENCE: 3

```
gacatccaga tgacccagtc tccagcttcc ctgtctgcat ctctgggaga aactgtcacc     60
atcgaatgtc gagcaagtga ggacatttat aatgctttag catggtatca gcagaagcca    120
gggaaatctc ctcagctcct gatctataat acagatacct tgcatactgg ggtcccatca    180
cgattcagtg gcagtggatc tggtacacaa tattctctca agataaacag cctgcaatct    240
gaagatgtcg caagttattt ctgtcagcac tatttccatt atcctcggac gttcggtgga    300
gggaccaagc tggagatcaa a                                              321
```

<210> SEQ ID NO 4
<211> LENGTH: 107
<212> TYPE: PRT
<213> ORGANISM: Rattus sp.

<400> SEQUENCE: 4

```
Asp Ile Gln Met Thr Gln Ser Pro Ala Ser Leu Ser Ala Ser Leu Gly
 1               5                  10                  15

Glu Thr Val Thr Ile Glu Cys Arg Ala Ser Glu Asp Ile Tyr Asn Ala
            20                  25                  30

Leu Ala Trp Tyr Gln Gln Lys Pro Gly Lys Ser Pro Gln Leu Leu Ile
            35                  40                  45

Tyr Asn Thr Asp Thr Leu His Thr Gly Val Pro Ser Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Val Ala Ser Tyr Phe Cys Gln His Tyr Phe His Tyr Pro Arg
                85                  90                  95

Thr Phe Gly Gly Gly Thr Lys Leu Glu Leu Lys
                100                 105
```

<210> SEQ ID NO 5
<211> LENGTH: 81
<212> TYPE: DNA
<213> ORGANISM: Homo sapiens

<400> SEQUENCE: 5

```
acaggcgcgc actccgaggt gcagctggtg gaatcaggag gtggtctggt cagcccgga     60
gggtccctgc gcctcagctg c                                              81
```

<210> SEQ ID NO 6
<211> LENGTH: 81
<212> TYPE: DNA
<213> ORGANISM: Homo sapiens

<400> SEQUENCE: 6
tcctggagcc tgtcgaaccc agttcacatt gttgttggtt agtgagaagc cagaggcagc    60
gcagctgagg cgcagggacc c                                              81

<210> SEQ ID NO 7
<211> LENGTH: 81
<212> TYPE: DNA
<213> ORGANISM: Homo sapiens

<400> SEQUENCE: 7
aactgggttc gacaggctcc aggaaaaggt ctggagtggg tgggaggagt ctgggctggt    60
ggagccacag attacaattc a                                              81

<210> SEQ ID NO 8
<211> LENGTH: 84
<212> TYPE: DNA
<213> ORGANISM: Homo sapiens

<400> SEQUENCE: 8
catttgtaag taagctgtgt tcttggagtt gtcgcgactg atggtgaatc gggatttgag    60
agctgaattg taatctgtgg ctcc                                           84

<210> SEQ ID NO 9
<211> LENGTH: 84
<212> TYPE: DNA
<213> ORGANISM: Homo sapiens

<400> SEQUENCE: 9
aagaacacag cttacttaca aatgaacagt ctgcgcgctg aagacacagc cgtttactac    60
tgtgccagag acgggggcta tagc                                           84

<210> SEQ ID NO 10
<211> LENGTH: 81
<212> TYPE: DNA
<213> ORGANISM: Homo sapiens

<400> SEQUENCE: 10
tgaggagacg gtgaccagag ttccttgacc ccaggcatcc atagcataga gggtagagct    60
gctatagccc ccgtctctgg c                                              81

<210> SEQ ID NO 11
<211> LENGTH: 78
<212> TYPE: DNA
<213> ORGANISM: Homo sapiens

<400> SEQUENCE: 11
acaggcgtgc actccgacat ccagatgacc cagtctccat cttccctgtc tgcatctgtg    60
ggagaccgcg tcaccatc                                                  78

<210> SEQ ID NO 12
<211> LENGTH: 78
<212> TYPE: DNA
<213> ORGANISM: Homo sapiens

<400> SEQUENCE: 12

```
tggcttctgc tgataccatg ctaaagcatt ataaatgtcc tcacttgctc gacatgtgat    60
ggtgacgcgg tctcccac                                                 78
```

<210> SEQ ID NO 13
<211> LENGTH: 78
<212> TYPE: DNA
<213> ORGANISM: Homo sapiens

<400> SEQUENCE: 13

```
gcatggtatc agcagaagcc agggaaagct cctaagctcc tgatctataa tacagatacc    60
ttgcatacag gggtccca                                                 78
```

<210> SEQ ID NO 14
<211> LENGTH: 78
<212> TYPE: DNA
<213> ORGANISM: Homo sapiens

<400> SEQUENCE: 14

```
caggctgctt atcgtgagag tatagtctgt accagatcca ctgccactga atcgtgatgg    60
gacccctgta tgcaaggt                                                 78
```

<210> SEQ ID NO 15
<211> LENGTH: 75
<212> TYPE: DNA
<213> ORGANISM: Homo sapiens

<400> SEQUENCE: 15

```
actctcacga taagcagcct gcaacctgaa gatttcgcaa cttatttctg tcagcactat    60
ttccattatc ctcgg                                                    75
```

<210> SEQ ID NO 16
<211> LENGTH: 75
<212> TYPE: DNA
<213> ORGANISM: Homo sapiens

<400> SEQUENCE: 16

```
caatctagaa ttctactcac gtttgatctc caccttggtc ccttgaccga acgtccgagg    60
ataatggaaa tagtg                                                    75
```

<210> SEQ ID NO 17
<211> LENGTH: 122
<212> TYPE: PRT
<213> ORGANISM: Homo sapiens

<400> SEQUENCE: 17

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Asn Asn
             20                  25                  30

Asn Val Asn Trp Val Arg Gln Ala Pro Gly Lys Gly Leu Glu Trp Val
         35                  40                  45

Gly Gly Val Trp Ala Gly Gly Ala Thr Asp Tyr Asn Ser Ala Leu Lys
     50                  55                  60

Ser Arg Phe Thr Ile Ser Arg Asp Asn Ser Lys Asn Thr Ala Tyr Leu
 65                  70                  75                  80

Gln Met Asn Ser Leu Arg Ala Glu Asp Thr Ala Val Tyr Tyr Cys Ala
                 85                  90                  95
```

```
Arg Asp Gly Gly Tyr Ser Ser Thr Leu Tyr Ala Met Asp Ala Trp
            100                 105                 110
Gly Gln Gly Thr Leu Val Thr Val Ser Ser
        115                 120

<210> SEQ ID NO 18
<211> LENGTH: 107
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15
Asp Arg Val Thr Ile Thr Cys Arg Ala Ser Glu Asp Ile Tyr Asn Ala
            20                  25                  30
Leu Ala Trp Tyr Gln Gln Lys Pro Gly Lys Ala Pro Lys Leu Leu Ile
        35                  40                  45
Tyr Asn Thr Asp Thr Leu His Thr Gly Val Pro Ser Arg Phe Ser Gly
    50                  55                  60
Ser Gly Ser Gly Thr Asp Tyr Thr Leu Thr Ile Ser Ser Leu Gln Pro
65                  70                  75                  80
Glu Asp Phe Ala Thr Tyr Phe Cys Gln His Tyr Phe His Tyr Pro Arg
                85                  90                  95
Thr Phe Gly Gln Gly Thr Lys Val Glu Ile Lys
            100                 105

<210> SEQ ID NO 19
<211> LENGTH: 117
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Glu Tyr
            20                  25                  30
Tyr Met His Trp Val Arg Gln Ala Pro Gly Lys Gly Leu Glu Trp Val
        35                  40                  45
Gly Leu Ile Asp Pro Glu Gln Gly Asn Thr Ile Tyr Asp Pro Lys Phe
    50                  55                  60
Gln Asp Arg Ala Thr Ile Ser Ala Asp Asn Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ala Arg Asp Thr Ala Ala Tyr Phe Asp Tyr Trp Gly Gln Gly Thr Leu
            100                 105                 110
Val Thr Val Ser Ser
        115

<210> SEQ ID NO 20
<211> LENGTH: 107
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15
Asp Arg Val Thr Ile Thr Cys Arg Ala Ser Arg Asp Ile Lys Ser Tyr
```

```
                    20                  25                  30
Leu Asn Trp Tyr Gln Gln Lys Pro Gly Lys Ala Pro Lys Val Leu Ile
            35                  40                  45

Tyr Tyr Ala Thr Ser Leu Ala Glu Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln His Gly Glu Ser Pro Trp
                85                  90                  95

Thr Phe Gly Gln Gly Thr Lys Val Glu Ile Lys
            100                 105

<210> SEQ ID NO 21
<211> LENGTH: 369
<212> TYPE: DNA
<213> ORGANISM: Mus musculus

<400> SEQUENCE: 21
gaggtgaagc tggtggagtc tgggggaggt ttagtgcagc ctggagggtc cctgaaactc      60
tcctgtgcag cctctggatt cactttcagt acctatacca tgtcttgggc tcgccagaca     120
ccagagaaga ggctggagtg ggtcgcatac attagtaaag gtggtggtag tacctactat     180
ccagacactg taaagggccg attcaccatc tccagggaca tgcgaagaa cacccctgtac    240 ctgcaaatga gcagtctgaa gtctgaggac acggccttgt attactgtgc aagaggggct     300
atgtatggta acgattttt ctatcctatg gactactggg gtcaaggaac ctcagtcacc     360
gtctcctca                                                            369

<210> SEQ ID NO 22
<211> LENGTH: 124
<212> TYPE: PRT
<213> ORGANISM: Mus musculus

<400> SEQUENCE: 22

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Thr Met Ser Trp Ala Arg Gln Thr Pro Glu Lys Arg Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Leu Tyr Tyr Cys
                85                  90                  95

Ala Arg Gly Ala Met Phe Gly Asn Asp Phe Phe Phe Pro Met Asp Arg
            100                 105                 110

Trp Gly Gln Gly Thr Ser Val Thr Val Ser Ser Ala
            115                 120

<210> SEQ ID NO 23
<211> LENGTH: 318
<212> TYPE: DNA
<213> ORGANISM: Mus musculus

<400> SEQUENCE: 23
```

```
gacattgttc tctcccagtc tccagcaatc atgtctgcat ctctagggga ggagatcacc    60
ctaacctgca gtgccagctt gagtgtaagt tacatgcact ggtaccagca gaagtcaggc   120
acttctccca agctcttgat ttatactaca tccaacctgg cttctggagt cccttctcgc   180
ttcagtggca gtgggtctgg gaccttttat tctctcacaa tcagtagtgt ggaggctgaa   240
gatgctgccg attattactg ccatcagtgg agtagttatc catggacgtt cggtggaggc   300
accaagctgg aaatcaaa                                                 318
```

<210> SEQ ID NO 24
<211> LENGTH: 106
<212> TYPE: PRT
<213> ORGANISM: Mus musculus

<400> SEQUENCE: 24

```
Asp Ile Val Leu Thr Gln Ser Pro Ala Ile Met Ser Ala Ser Leu Gly
1               5                   10                  15

Glu Glu Val Thr Leu Thr Cys Ser Ala Ser Ser Ser Val Ser Tyr Met
                20                  25                  30

His Trp Tyr Gln Gln Lys Ser Gly Thr Ser Pro Lys Leu Leu Ile Tyr
            35                  40                  45

Thr Thr Ser Asn Leu Ala Ser Gly Val Pro Ser Arg Phe Ser Gly Ser
        50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys
            100                 105
```

<210> SEQ ID NO 25
<211> LENGTH: 81
<212> TYPE: DNA
<213> ORGANISM: Homo sapiens

<400> SEQUENCE: 25

```
acaggcgcgc actccgaggt gcagctgctg gagtctgggg gaggtttagt gcagcctgga    60
gggtccctgc gcctctcctg t                                              81
```

<210> SEQ ID NO 26
<211> LENGTH: 81
<212> TYPE: DNA
<213> ORGANISM: Homo sapiens

<400> SEQUENCE: 26

```
ccctggggcc tggcgagccc agctcatggt ataggtactg aaagtgaatc cagaggctgc    60
acaggagagg cgcagggacc c                                              81
```

<210> SEQ ID NO 27
<211> LENGTH: 81
<212> TYPE: DNA
<213> ORGANISM: Homo sapiens

<400> SEQUENCE: 27

```
tgggctcgcc aggccccagg gaaggggctg gagtgggtcg catacattag taaaggtggt    60
ggtagtacct actatccaga c                                              81
```

<210> SEQ ID NO 28

```
<211> LENGTH: 81
<212> TYPE: DNA
<213> ORGANISM: Homo sapiens

<400> SEQUENCE: 28
ttgcaggtac agggtgttct tcgagttgtc cctggagatg gtgaatcggc cctttacagt      60
gtctggatag taggtactac c                                                81

<210> SEQ ID NO 29
<211> LENGTH: 81
<212> TYPE: DNA
<213> ORGANISM: Homo sapiens

<400> SEQUENCE: 29
aagaacaccc tgtacctgca aatgaacagt ctgcgggctg aggacagcgc cgtctattac      60
tgtgcaagag gggctatgtt t                                                81

<210> SEQ ID NO 30
<211> LENGTH: 81
<212> TYPE: DNA
<213> ORGANISM: Homo sapiens

<400> SEQUENCE: 30
ggagacggtg accagggttc cttgacccca gcggtccata ggaaagaaaa aatcgttacc      60
aaacatagcc cctcttgcac a                                                81

<210> SEQ ID NO 31
<211> LENGTH: 78
<212> TYPE: DNA
<213> ORGANISM: Homo sapiens

<400> SEQUENCE: 31
acaggcgtgc actccgacat tgttctcacc cagtctccat ccagcctgtc tgcgtctgtc      60
ggggaccggg tcaccatt                                                    78

<210> SEQ ID NO 32
<211> LENGTH: 78
<212> TYPE: DNA
<213> ORGANISM: Homo sapiens

<400> SEQUENCE: 32
gcctggcttc tgctggtacc agtgcatgta actcacacta gagctggcgc tgcaggtaat      60
ggtgacccgg tccccgac                                                    78

<210> SEQ ID NO 33
<211> LENGTH: 78
<212> TYPE: DNA
<213> ORGANISM: Homo sapiens

<400> SEQUENCE: 33
tggtaccagc agaagccagg caaggctccc aagctcctga tttatactac atccaacctg      60
gcttctggag tcccttct                                                    78

<210> SEQ ID NO 34
<211> LENGTH: 75
<212> TYPE: DNA
<213> ORGANISM: Homo sapiens

<400> SEQUENCE: 34
cagactactg attgtgaggg tataatcggt cccagaccca ctgccgctga agcgagaagg      60
```

```
gactccagaa gccag                                                  75
```

<210> SEQ ID NO 35
<211> LENGTH: 78
<212> TYPE: DNA
<213> ORGANISM: Homo sapiens

<400> SEQUENCE: 35

```
accctcacaa tcagtagtct gcagcctgaa gatttcgcca cctattactg ccatcagtgg   60
agtagttatc catggacg                                                 78
```

<210> SEQ ID NO 36
<211> LENGTH: 75
<212> TYPE: DNA
<213> ORGANISM: Homo sapiens

<400> SEQUENCE: 36

```
taagttagat ctattctact cacgttttat ttccaccttg gtgcctccac cgaacgtcca   60
tggataacta ctcca                                                    75
```

<210> SEQ ID NO 37
<211> LENGTH: 124
<212> TYPE: PRT
<213> ORGANISM: Homo sapiens

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Thr Met Ser Trp Ala Arg Gln Ala Pro Gly Lys Gly Leu Glu Trp Val
        35                  40                  45

Ala Tyr Ile Ser Lys Gly Gly Gly Ser Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Gly Ala Met Phe Gly Asn Asp Phe Phe Phe Pro Met Asp Arg
            100                 105                 110

Trp Gly Gln Gly Thr Leu Val Thr Val Ser Ser Ala
        115                 120

<210> SEQ ID NO 38
<211> LENGTH: 106
<212> TYPE: PRT
<213> ORGANISM: Homo sapiens

<400> SEQUENCE: 38

Asp Ile Val Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Gln Ala Pro Lys Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Val Ala Thr Tyr Tyr Cys His Gln Trp Ser Ser Tyr Pro Trp Thr
                85                  90                  95

Phe Gly Gly Gly Thr Lys Val Glu Ile Lys
            100                 105

<210> SEQ ID NO 39
<211> LENGTH: 122
<212> TYPE: PRT
<213> ORGANISM: Homo sapiens

<400> SEQUENCE: 39

Glu Val Gln Leu Leu Glu Ser Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Ala Pro Gly Lys Gly Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Lys Ser Thr
65                  70                  75                  80

Leu Tyr Leu Gln Met Asn Thr Leu Gln Ala Glu Asp Ser Ala Ile Tyr
                85                  90                  95

Tyr Cys Thr Arg Asp Arg Gly Leu Arg Phe Tyr Phe Asp Tyr Trp Gly
            100                 105                 110

Gln Gly Thr Leu Val Thr Val Ser Ser Ala
        115                 120

<210> SEQ ID NO 40
<211> LENGTH: 106
<212> TYPE: PRT
<213> ORGANISM: Homo sapiens

<400> SEQUENCE: 40

Gln Thr Val Leu Thr Gln Ser Pro Ser Ser Leu Ser Val Ser Val Gly
1               5                   10                  15

Asp Arg Val Thr Ile Thr Cys Arg Ala Ser Ser Ser Val Thr Tyr Ile
            20                  25                  30

His Trp Tyr Gln Gln Lys Pro Gly Leu Ala Pro Lys Ser Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln His Trp Ser Ser Lys Pro Pro Thr
                85                  90                  95

Phe Gly Gln Gly Thr Lys Val Glu Val Lys
            100                 105